US011379637B2

(12) United States Patent
Collins et al.

(10) Patent No.: US 11,379,637 B2
(45) Date of Patent: Jul. 5, 2022

(54) INTERSTITIAL CONTROL DURING ADDITIVE MANUFACTURING

(71) Applicant: Iowa State University Research Foundation, Inc., Ames, IA (US)

(72) Inventors: Peter C. Collins, Ames, IA (US); Martin Thuo, Ames, IA (US); Thomas Ales, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 208 days.

(21) Appl. No.: 16/787,973

(22) Filed: Feb. 11, 2020

(65) Prior Publication Data

US 2020/0327267 A1    Oct. 15, 2020

Related U.S. Application Data

(60) Provisional application No. 62/833,405, filed on Apr. 12, 2019.

(51) Int. Cl.
*G06F 30/23* (2020.01)
*B29C 64/393* (2017.01)
(Continued)

(52) U.S. Cl.
CPC ............ *G06F 30/23* (2020.01); *B29C 64/153* (2017.08); *B29C 64/393* (2017.08); *B33Y 10/00* (2014.12);
(Continued)

(58) Field of Classification Search
CPC .. G06F 30/23; G06F 2113/10; G06F 2119/08; B29C 64/153; B29C 64/393;
(Continued)

(56) References Cited

U.S. PATENT DOCUMENTS 8,546,717 B2    10/2013  Stecker
2013/0136868 A1*    5/2013  Bruck .................. B23K 26/144
427/554
(Continued)

OTHER PUBLICATIONS

P.C. Collins et al., "Microstructural Control of Additively Manufactured Metallic Materials", Annu. Rev. Mater. Res. 2016.46:63-91 (Year: 2016).*
(Continued)

*Primary Examiner* — Thomas C Lee
*Assistant Examiner* — Michael Tang
(74) *Attorney, Agent, or Firm* — Schwegman Lundberg & Woessner, P.A.

(57) ABSTRACT

Various embodiments relate to additive manufacturing in which the Langmuir equation can be used to predict composition in the processing. This equation can be integrated into a model with knowledge of elemental solubility and relative reactivity of relevant elements in the additive manufacturing processing. Use of thermodynamic principles can be programmed into a finite element modeling strategy integrating the Langmuir equation, coupling the thermal fields of additive manufacturing and the surrounding environments with the rules and/or equations to predict solute pickup and/or solute loss. The modeling strategy can be implemented to identify the elements in relative concentrations to be used in the additive manufacturing processing to provide for the controlled loss of certain elements to prevent absorption of unwanted elements into molten material, formed by additive manufacturing, from the atmosphere around the molten material. Additional systems and methods are disclosed.

20 Claims, 26 Drawing Sheets

(51) Int. Cl.
| | |
|---|---|
| *B29C 64/153* | (2017.01) |
| *B33Y 10/00* | (2015.01) |
| *G06F 113/10* | (2020.01) |
| *G06F 119/08* | (2020.01) |
| *B33Y 50/02* | (2015.01) |

(52) U.S. Cl.
CPC ........... *B33Y 50/02* (2014.12); *G06F 2113/10* (2020.01); *G06F 2119/08* (2020.01)

(58) Field of Classification Search
CPC ......... B33Y 10/00; B33Y 50/02; B33Y 40/20; B33Y 50/00; B22F 10/20; B22F 10/32; B22F 2003/248; B22F 2203/00; B22F 2207/00; B22F 2999/00; B22F 3/24; G05B 19/4099; G05B 2219/49023; Y02P 10/25; G16C 60/00
See application file for complete search history.

(56) References Cited

U.S. PATENT DOCUMENTS

| | | | | |
|---|---|---|---|---|
| 2015/0165554 | A1* | 6/2015 | Voice | B23K 26/34 |
| | | | | 219/74 |
| 2015/0275332 | A1* | 10/2015 | Haidar | B22F 9/20 |
| | | | | 75/351 |
| 2016/0228991 | A1* | 8/2016 | Ryan | C22C 29/12 |
| 2018/0311757 | A1* | 11/2018 | Bucknell | B29C 64/264 |
| 2019/0022725 | A1* | 1/2019 | Bauer | B22F 1/0059 |
| 2019/0193160 | A1* | 6/2019 | Brunhuber | C22C 27/04 |
| 2020/0089826 | A1* | 3/2020 | Liu | B33Y 50/00 |
| 2020/0131661 | A1* | 4/2020 | Copic | C25D 13/02 |
| 2020/0373226 | A1* | 11/2020 | Oda | H01L 24/45 |
| 2021/0178688 | A1* | 6/2021 | Otis, Jr. | B65G 53/60 |

OTHER PUBLICATIONS

Christine Hillier, "Powder-Cored Tubular Wire Development for Electron Beam Freeform Fabrication", thesis, Department of Metallurgical and Materials Engineering, Colorado School of Mines, 2010 (Year: 2010).*

S.L. Semiatin, et al., "Diffusion Models for Evaporation Losses during Electron-Beam Melting of Alpha/Beta-Titanium Alloys", Metallurgical and Materials Transactions B, vol. 35B, Apr. 2004— 235. (Year: 2004).*

Alcock, C. B., et al., "Vapour Pressure of the Metallic Elements", Canadian Metallurgical Quarterly, 23(3), (1984), 309-313.

Ales, Thomas K., "An integrated model for the probabilistic prediction of yield strength in electron-beam additively manufactured Ti—6Al—4V", Graduate Thesis and Dissertations, 16306, Iowa State University, (2018), 77 pgs.

Baker, Andrew H., "New Nomenclatures for Heat Treatments of Additively Manufactured Titanium Alloys", JOM, 69, (2017), 1221-1227.

Bensaude-Vincent, Bernadette, et al., "Materials science: A field about to explode?", Nature Materials, 3(6), (2004), 345-347.

Boivineau, M., et al., "Thermophysical Properties of Solid and Liquid Ti—6Al—4V (TA6V) Alloy", International Journal of Thermophysics, 27(2), (Mar. 2006), 507-528.

Collins, P. C., et al., "Development of methods for the quantification of microstructural features in a + ß-processed a/ß titanium alloys", Materials Science and Engineering: A, vol. 508, Nos. 1-2, Welk, (2009), 174-182.

Collins, P. C., et al., "Microstructural Control of Additively Manufactured Metallic Materials", Annual Review of Material Research, vol. 46, (2016), 63-91.

Collins, Peter C., et al., "Progress Toward an Integration of Process—Structure—Property—Performance Models for "Three-Dimensional (3-D) Printing" of Titanium Alloys", JOM: The Journal of the Minerals, Metals & Materials Society, 66(7), (Jun. 2014), 1299-1309.

Denlinger, Erik R., "Thermomechanical Modeling of Additive Manufacturing Large Parts", Journal of Manufacturing Science and Engineering, 136(6): 061007, (Dec. 2014), 8 pgs.

Goldak, J., et al., "A New Finite Element Model for Welding Heat Sources", Metallurgical Transactions B, vol. 15B, (Jun. 1984), 299-306.

Gorsse, Stephane, et al., "Additive manufacturing of metals: a brief review of the characteristic microstructures and properties of steels, Ti—6Al—4V and high-entropy alloys", Science and Technology of Advanced Materials, 18(1), (2017), 584-610.

Hayes, Brian J., et al., "Predicting tensile properties of Ti—6Al—4V produced via directed energy deposition", Acta Materialia, vol. 133, (2017), 120-123.

Kobryn, P. A., et al., "Microstructure and texture evolution during solidification processing of Ti—6Al—4V", Journal of Materials Processing Technology, 135(2), (2003), 330-339.

Langmuir, Irving, et al., "The Vapor Pressure of Metallic Tungsten", The Physical Review, vol. II, No. 5, (Nov. 1913), 329-342.

Lecoanet, A., et al., "Simulation of the Temperature Profile During Welding with COMSOL Multiphyics(r) Software Using Rosenthal's Approach", Proceedings of the 2014 COMSOL Conference, Boston, MA, (2014), 7 pgs.

Michaleris, P., et al., "Modeling metal deposition in heat transfer analyses of additive manufacturing processes", Finite Elements in Analysis and Design, vol. 86, (2014), 51-60.

Murgau, C. Charles, et al., "A model for Ti—6Al—4V microstructure evolution for arbitrary temperature changes", Modeling Simul. Mater. Sci. Eng., vol. 20,055006, (2012), 1-23.

Quinn, T. J., et al., "A radiometric determination of the Stefan-Boltzmann constant and thermodynamic temperatures between -40C and +100C", Philos. Trans. R. Soc. London Ser. A, 316(1536), (1985), 85-189.

Sosa, John, et al., "Development and application of MIPAR™: a novel software package for two- and three-dimensional microstructural characterization", Integrating Materials and Manufacturing Innovation, No. 3:10, (Dec. 20142014), 18 pgs.

Stecker, S., et al., "Advanced Electron Beam Free Form Fabrication Methods & Technology", American Welding Society Conference, vol. 17, (Nov. 2006), 35-46.

Wohlers, Terry, et al., "History of Additive Manufacturing", Wohlers Associates, (2016), 1-38.

* cited by examiner

INTERSTITIAL CONTROL DURING ADDITIVE MANUFACTURING

PRIORITY APPLICATION

This application claims priority under 35 U.S.C. 119(e) from U.S. Provisional Application Ser. No. 62/833,405 filed on 12 Apr. 2019, which application is incorporated herein by reference in its entirety.

STATEMENT OF GOVERNMENT SUPPORT

This invention was made with government support under Contract No. HR0011-12-C-0035 awarded by the Defense Advanced Research Projects Agency (DARPA)). The government has certain rights in the invention.

FIELD OF THE INVENTION

The invention relates generally to manufacturing, in particular to technologies related to additive manufacturing.

BACKGROUND

Additive manufacturing (AM) relates to manufacturing technologies that construct three dimensional (3D) objects by adding material in a layer-upon-layer format. Different AM technologies include the use of a computer, 3D modeling software such as computer aided design (CAD), machine equipment, and material that can be layered. Typically, AM equipment reads in data from a CAD file and forms successive layers of liquid, powder, sheet material, or other material, in a layer-upon-layer fashion, to fabricate a 3D object. AM encompasses many technologies including such techniques as 3D printing, rapid prototyping (RP), direct digital manufacturing (DDM), layered manufacturing, and additive fabrication.

Mass transport of selective atomic species from one phase to another phase occurs at the liquid surface in metal-based AM processes. Yet, the processes that control the deposited chemical compositions are rarely described qualitatively, let alone quantitatively, and there does not exist a widely accepted method or approach to predict the composition of as-deposited materials. Complicating the effort to develop a hypothesis to explain and predict the final composition given certain process conditions is the fact that the energy sources vary, and the environments of AM platforms range from vacuums to positive pressure, with varying degrees of purity of "inert atmospheres."

BRIEF DESCRIPTION OF THE FIGURES

The drawings illustrate generally, by way of example, but not by way of limitation, various embodiments of the invention in which.

DETAILED DESCRIPTION

Figure 1:
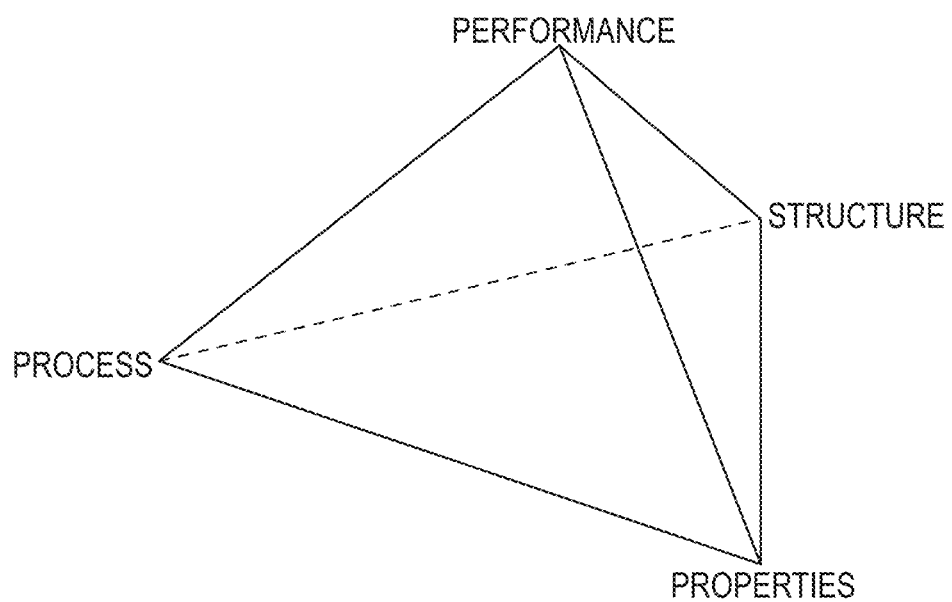
FIG. 1 shows the materials tetrahedron.

The following detailed description refers to the accompanying drawings that show, by way of illustration, various embodiments of the invention. These embodiments are described in sufficient detail to enable those of ordinary skill in the art to practice these and other embodiments. Other embodiments may be utilized, and structural, logical, mechanical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

The inventors have used the Langmuir equation to quantitatively predict elemental volatilization under vacuum conditions. Under atmosphere, even inert, trace elements, for example oxygen (O) and nitrogen (N), can be gettered by absorption by the molten material. To getter is to remove gas from the atmosphere by sorption, which includes processes of absorption and adsorption. The application of the Langmuir equation seems to apply reasonably well to this case. However, the inventors have also observed that the application of the Langmuir equation to the prediction of interstitial pickup in large-scale electron beam additive manufacturing (EBAM) systems fails, where the EBAM systems operate under vacuum. The theory is that certain species preferentially volatilize and react with trace elements in the vacuum to form a gaseous compound molecule that preferentially consumes all of the available trace elements at the local molten pool. The controlled loss of certain elements can establish a protective vapor plume around molten material formed in an AM process. If this plume has a strong affinity for the species of the surrounding atmosphere, for example oxygen or nitrogen, it can react with those species, preventing their absorption into the liquid metal and controlling impurity contents. For example, aluminum (Al) can preferentially volatilize and react with trace elements of oxygen in vacuum to form a gaseous compound molecule of $Al_xO_y$.

The composition of a material has a significant influence on the mechanical behavior of the material. The composition of a material is set by its final molten form or composition from final extractive metallurgy steps. Additive manufacturing is often a fusion process, taking the material into a molten state prior to solidification and subsequent layered material such as 3D printing layers. Since additive manufacturing distributes final molten product across a much wider cross-section of the supply chain, and since that supply chain is not accustomed to certifying chemical composition for every machine, there is a need for a tool that can predict and simulate composition in the final form. Such tools will permit companies to engineer their product composition, permitting them to engineer the performance of their material.

In various embodiments, the Langmuir equation can be used to predict composition in AM processing, in which this equation can be applied with knowledge of elemental solubility and relative reactivity of materials involved in the process. Use of the Langmuir equation, for elements that are typically solid or liquid at room temperature, can be valid for elemental species loss under both inert (positive pressure) and vacuum. This equation can be valid for certain gaseous elemental species pickup under inert atmosphere, and for certain gaseous species under vacuum. Use of the Langmuir equation can be invalid for certain gaseous elemental species A that are barred from being absorbed by the molten metal because there is an excess of elemental species B loss, when element B would form a more stable compound with A than A being absorbed into the liquid metal. With this knowledge of the applicability of the Langmuir equation, sacrificial solutes that would volatilize under vacuum or other atmospheres, and getter the other elements that may be present in the atmosphere, preventing them from being consumed by the liquid metal, can be engineered. These thermodynamic principles can be programmed into a finite element modeling strategy, coupling the thermal fields of additive manufacturing and the surrounding environments with the rules and/or equations to predict solute pickup and/or solute loss.

As noted in B. Bensaude-Vincent and A. Hessenbruch. "Materials science: a field about to explode?" *Nature Materials*, vol. 3, pp. 345-347, 2004, materials achieve their highest performance when the mutual influences of "structure, properties, performance and process," are well understood not only in their individual, isolated contributions but also their interrelationships. FIG. 1 shows the materials tetrahedron. This material science engineering (MSE) paradigm can also be expressed linearly as the processing-chemistry-microstructure properties-performance paradigm.

Presently, these interactions are not well understood with regard to AM materials, although there have been efforts in individual areas, especially when compared to more traditional thermophysical processing routes which have matured over the span of decades. In B. J. Hayes, B. W. Martin. B. Welk. S. J. Kuhr. T. K. Ales, D. A. Brice. I. Ghamarian, A. H. Baker, C. V. Haden, D. G. Harlow, H. L. Fraser and P. C. Collins, "Predicting tensile properties of Ti-6Al-4V produced via directed energy deposition." *Acta Materialia*, vol. 133, pp. 120-133, 31 Jul. 2017, a phenomenological model was developed for the prediction of yield strength ($\sigma_y$) in additively manufactured Ti-6Al-4V as a function of chemistry, and microstructure. By solving for the properties using the available chemical and microstructural information, the performance can be predicted. Performance, in the context of the teachings herein, is used in the same manner that a design engineer would use the term. That is, it is a statistically significant representation of samples that gives rise to "design allowable" curves. Ideally, these design allowable curves would either be predicted either completely or in part, reducing the number of required test specimens to develop an aerospace allowable curve from the 897 samples presently required.

Figure 2:
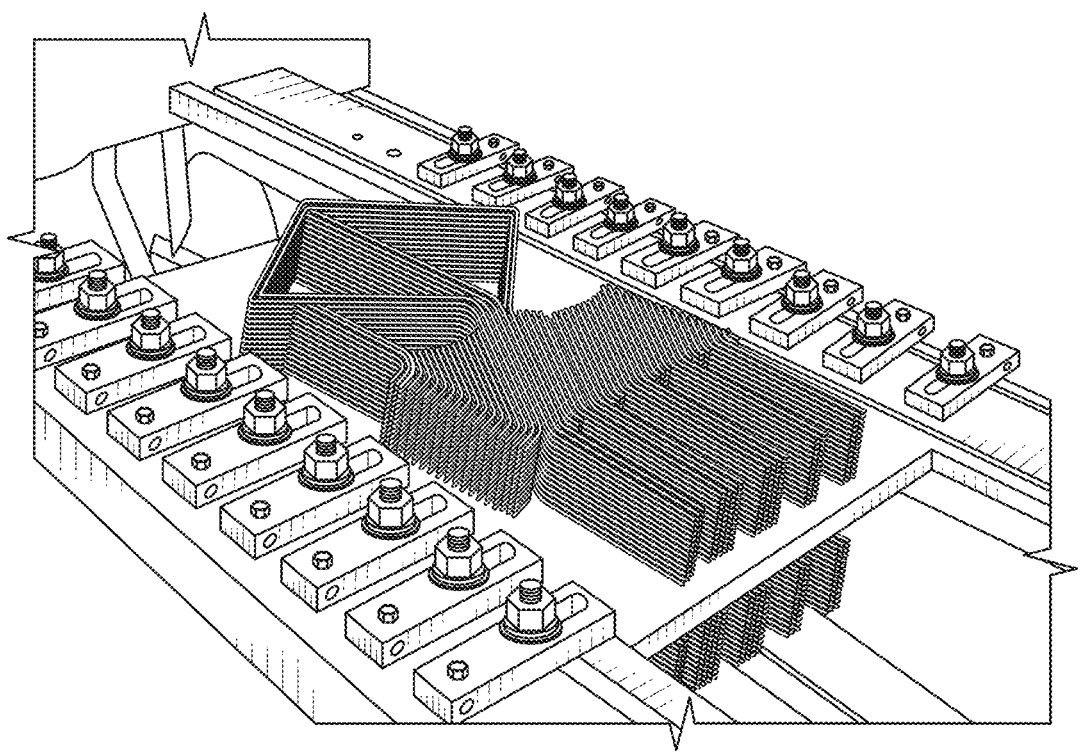
FIG. 2 shows a small electron beam additive manufacturing component.

Various AM processes exist, such as Selective Laser Sintering (SLS). Selective Laser Melting (SLM). Laser Engineered Net Shape (LENS), and EBAM. The first three methods are characterized by the use of a laser as the point source, and can be performed either in an inert atmosphere, or vacuum. From S. Gorsse, C. Hutchingson, M. Gound and R. Banerjee, "Additive manufacturing of metals: a brief review of the characteristic microstructures and properties of steels, Ti-6Al-4V and high-entropy alloys," *Science and Technology of Advanced Materials*, vol. 18, no. 1, pp. 584-610, 2017: "Most laser-based systems have a maximum build rate of about 70 cm³/h." In stark contrast, the EBAM process operates on a much larger scale with deposition rates up to 40 lb/h. See S. Stecker. K. W. Lachenberg. H. Wang and R. C. Salo, "Advanced electron beam free form fabrication methods & technology," *American Welding Society Conference*, vol. 17. pp. 35-46. November 2006. Assuming a material density of 0.00976 lb/cm³ (converted from P. C. Collins, C. V. Haden, I. Ghamarian, B. J. Hayes, T. Ales. G. Penso, V. Dixit and G. Harlow, "Progress Toward an Integration of Process-Structure-Property-Performance Models for "Three-Dimensional (3-D) Printing" of Titanium Alloys," *JOM*, vol. 66, no. 7, pp. 1299-1309, July 2014, for Ti-6Al-4V), this gives a volumetric build rate of approximately 4100 cm³/h, several orders of magnitude greater than the more common laser-based processes. For the EBAM process, there is the problem of operating under a vacuum compared to an inert atmosphere when using alloys that have elements with large differences in boiling point, such as Ti-6Al-4V. FIG. 2 shows a small EBAM component, weighing approximately 180 pounds, where the substrate is 1" thick. However, builds in excess of 1000 pounds have been achieved using EBAM processes, with part build envelopes of up to "19 ft.×4 ft.×4 ft. (5.79 m×1.22 m×1.22 m) or round parts up to 8 ft. (2.44 m) in diameter," according to Sciaky. Inc., "Sciaky Inc.," available online at www.sciaky.com, as of 23 Mar. 2018.

A thermal process model is taught herein for EBAM, providing the needed process linkage in the MSE paradigm, as it provides element-specific temperature-time histories, allowing the structure and chemistry properties to be predicted, followed by the resulting properties, and thus performance. Although the particular framework is presented specifically for the commercial engineering alloy Ti-6Al-4V, it is based upon fundamental physics that are alloy agnostic. Thus, this framework should be able to be adapted for each alloy family or process of interest. Within this disclosure, the models and attending theory are presented as a specific example of an integrated approach and engineering philosophy.

For calibration and verification of the model, a rich database consisting of more than 300 samples was developed and leveraged (See B. J. Hayes. B. W. Martin, B. Welk, S. J. Kuhr, T. K. Ales, D. A. Brice, I. Ghamarian, A. H. Baker. C. V. Haden. D. G. Harlow, H. L. Fraser and P. C. Collins. "Predicting tensile properties of Ti-6Al-4V produced via directed energy deposition." *Acta Materialia*, vol. 133, pp. 120-133, 31 Jul. 2017), along with a novel statistical method to allow the generation of a cumulated probability distribution function (CDF). These approaches permit multiple heat treatments for Ti-6Al-4V to be explored, and the results of three such heat treatments are discussed later.

Figure 3:
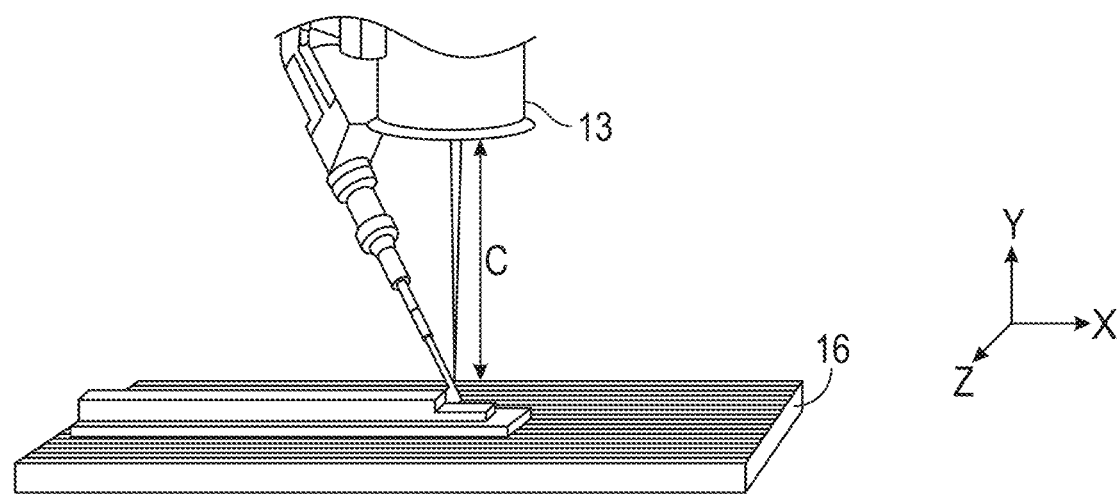
FIG. 3 shows a typical electron beam additive manufacturing head and chamber.

Consider EBAM. While there are detailed histories available for powder-based electron beam systems, like those developed by Arcam in T. Wohlers and T. Gornet, "History of Additive Manufacturing," Wohler Associates, 2016, there is relatively little about wire-fed systems such as those supplied by Sciaky, Inc. A first explicit mention of a wire-fed EBAM process was made in U.S. Pat. No. 8,546,717 having application Ser. No. 12/883,340, "Electron Beam Layer Manufacturing." This patent described the use of an electron beam source and wire feed to manufacture a three-dimensional part via layers shown in FIG. 3, taken from FIG. 1B of U.S. Pat. No. 8,546,717, showing a typical EBAM head and chamber. A motion controlled stage 16 moves in the X/Z direction, while the deposition head 13 moves in the Y direction. Deposition can occur either in a single direction, or use both X/Z directions for deposition. The relatively large input wire diameters of approximately 0.125" limits the resolution of the components that the EBAM process can produce, but results in very high deposition rates, making the EBAM process suitable for very large parts. These EBAM preforms are near net shape and can then become equivalent input to a forging or billet for use traditional machining processes, but with the advantages of less waste and a higher fly-to-buy ratio in the finished component.

There are several significant differences in the EBAM approach, relative to the smaller scale processes of Selective Laser Melting (SLM) or Laser Engineered Net Shape (LENS). Two of these differences have a direct influence on the resulting metallurgy of the deposited material. First, there is the issue of energies, a typical LENS system may be powered by a 450-500 W laser, whereas the EBAM beam power is set around 8 kW for most Ti-6Al-4V builds.

Secondly, there is the issue of aluminum vaporization. From R. Honig and D. Kramer, Vapor pressure data for the solid and liquid elements, RCA Rev., 1969, p. 285, aluminum's boiling point is given as 2973K at atmosphere. With thermal models showing the melt pool reaching temperatures in excess of 3600K, the loss of aluminum through vaporization is significant, and compounded by the free-expansion effect provided by the vacuum as compared to the build occurring in an inert atmosphere.

Currently the vaporization issue is dealt with by using input wire that is in excess of the target chemistry, and relying on the vaporization process itself to bring the melt into acceptable limits for chemistry: usually between 5.5%-6.5% by weight if one is trying to use ASTM B348 or F2924 equivalent chemistries in the final build. The current approach lacks rules to predict the chemistry differential and is typically Edisonian. An Edisonian approach employs trial and error discovery rather than a systematic theoretical approach.

Consider a thermal problem. In the literature, there are abundant solutions for solving the thermal problem. A well-known collection of information regarding the thermal problem comes from the seminal work of Pan Michaleris, "Thermomechanical Modeling of Additive Manufacturing Large Parts," in ASTM International, "Standard Test Methods for Tension Testing of Metallic Materials," ASTM International, West Conshohocken, 2014, which presents an efficient solution to the thermal and mechanical problem. This article presents several techniques including, but not limited to, "hybrid quiet inactive element activation," and "adaptive coarsening," of the element mesh to allow for solving of the thermal problem. Unfortunately. ABAQUS, which is a software suite for finite element analysis and computer-aided engineering, cannot feasibly implement the adaptive coarsening algorithm presented at this time, but it has incorporated some of the ideas in the "hybrid quiet inactive element" technique through the UEPACTIVATIONVOL (Anything appearing in a monospaced font refers to an actual software object, command, subroutine or function within a software package or programming language) subroutine present in ABAQUS/2017 and later releases.

The simulations presented in this disclosure do not make use of the adaptive coarsening method, so they are not computationally efficient, and thus make use of cluster computing. The aim of such simulations though is to demonstrate the feasibility of integrating the multiple legs of Fleming's tetrahedron of FIG. 1.

Figure 4:
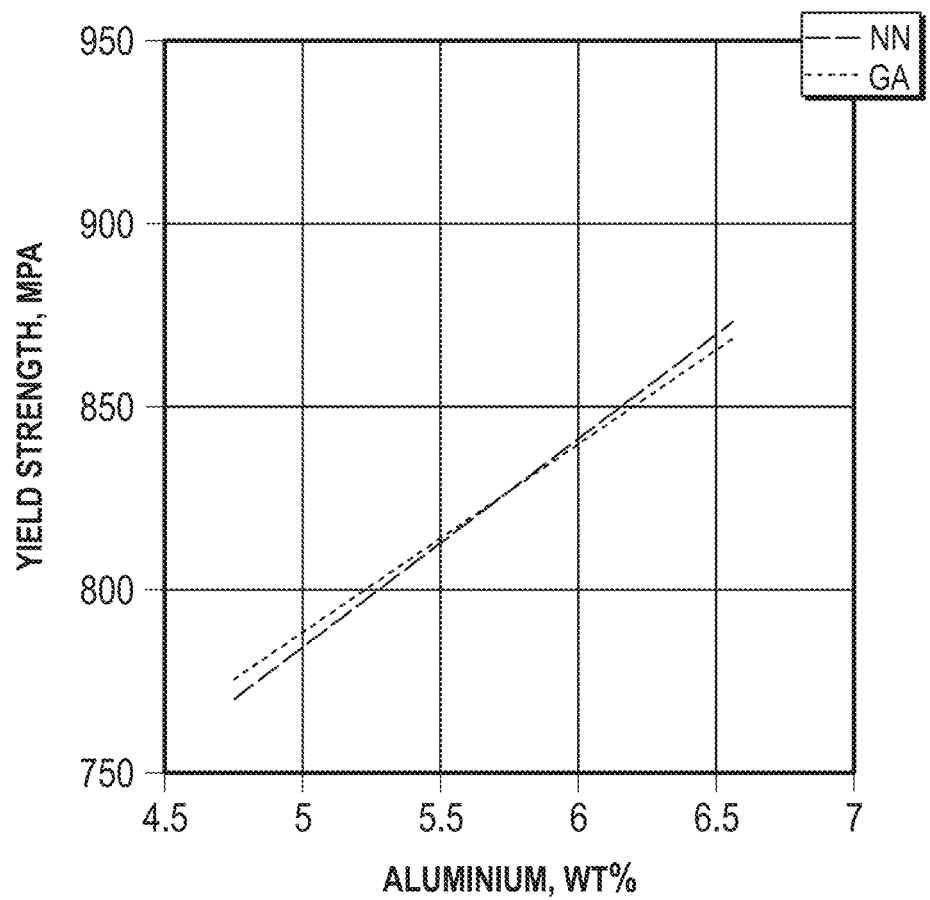
FIG. 4 shows a virtual experiment varying aluminum content and its effect on yield strength.

Consider the role of aluminum in Ti-6Al-4V. Aluminum is the most widely used alpha stabilizer in titanium, including Ti-6Al-4V. and is capable of influencing the yield strength in excess of 70 MPa by only varying the aluminum content by 1 wt %, as shown in FIG. 4 from P. C. Collins. C. V. Haden, I. Ghamarian, B. J. Hayes. T. Ales, G. Penso, V. Dixit and G. Harlow, "Progress Toward an Integration of Process-Structure-Property-Performance Models for "Three-Dimensional (3-D) Printing" of Titanium Alloys." *JOM*, vol. 66, no. 7, pp. 1299-1309, July 2014. FIG. 4 shows a virtual experiment varying Al-content and its effect on yield strength $\sigma_y$. Owing to the formation of the $\alpha_2$ ($Ti_3Al$) phase, the aluminum content is capped at 6.5 wt %, and details of acceptable chemistries is given in ASTM B348, one of the widely used standards. It must be kept in mind that the 70 MPa value above is given by a virtual experiment performed in previous work, and does not take aluminum's effect on the morphology of the alpha-laths, which may influence the yield strength through Hall-Petch effects due to the lath size. Virtual experiments permit the assessment of a single variable, for example Al content, on the resulting material property. Such experiments would not be possible in actuality due to the interrelated effects that chemistry has on structure and, by extension properties and performance.

A lath is a morphology (shape) of a particular microstructure feature. A lath can, in its simplest form, be considered to approximate a pancake or a deck of playing cards, where two of the geometric descriptors, for example along the x-axis and y-axis, are larger (sometimes significantly larger) than the third geometric descriptor, for example along the z-axis. The description of laths is slightly more complex as laths branch and interconnect, but the concept of a lath provides the materials science community a simple term that can be quantitatively measured. A alpha ($\alpha$) lath in titanium alloys is one of two primary crystal structures in titanium alloys, where the alpha phase in titanium alloys is a hexagonally close packed structure. A crystal structure describes how the atoms sit in their crystal lattice. The alpha phase is stabilized by aluminum, oxygen, and nitrogen among other elements. This crystal structure is exceptionally well known to the titanium community. It forms upon cooling in many or most titanium alloys from the parent (high temperature) phase, which is the beta structure. The alpha lath is the geometry of the hexagonally close packed (hcp) structure. The beta ($\beta$) phase is the other primary crystal structure in most titanium alloys. The beta phase is a body centered cubic structure, where this structure is stabilized by V, Fe, Mo, Ta, Nb, Cr, Ni, and Mn, among many other elements. This phase is also equally well known to the titanium community. The beta phase is less "lath like" and more of a thin network of interfaces enveloping the laths. One can measure the thickness of the beta "ribs" in the same way that one can measure the alpha laths.

Figure 5:
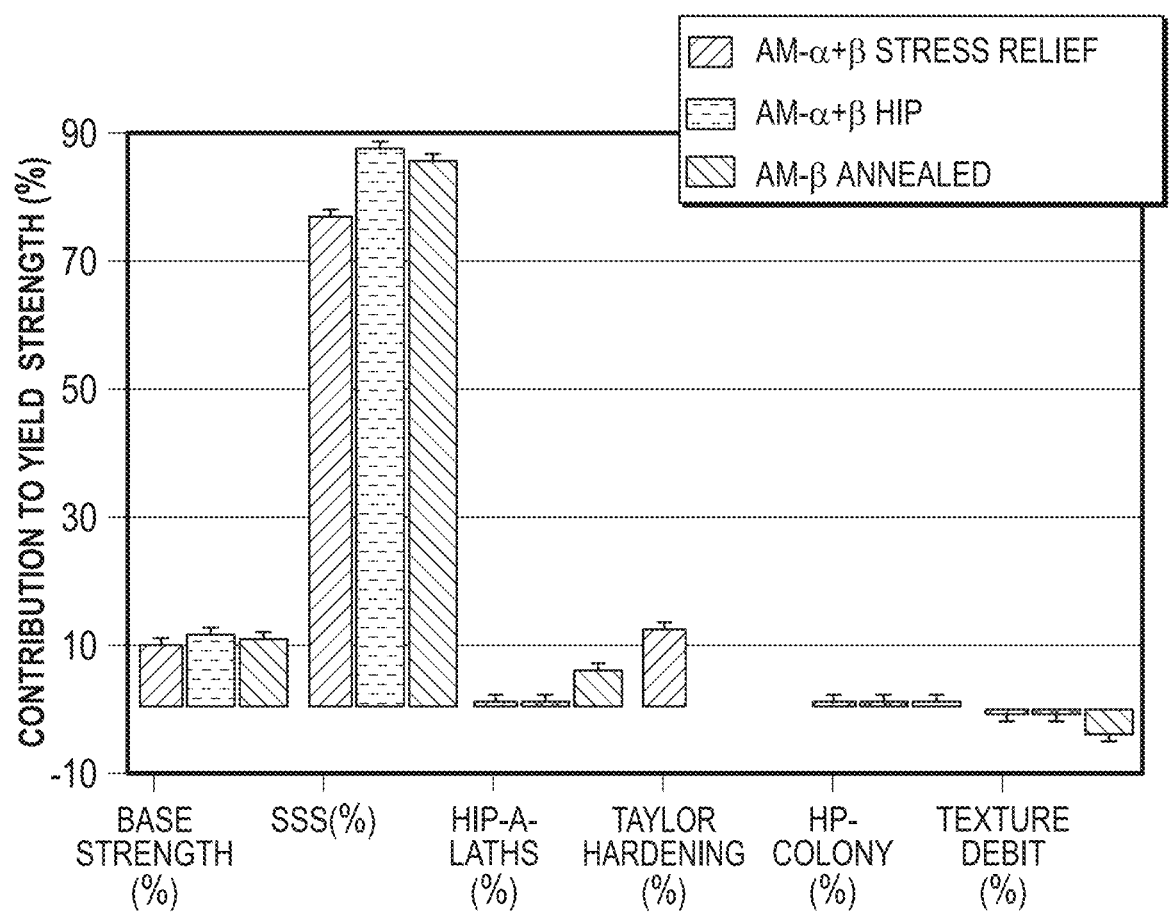
FIG. 5 shows the roles of various strengthening mechanisms of Ti-6Al-4V and their percent contribution to overall yield strength of the material.

FIG. 5, taken from FIG. 17 of B. J. Hayes, B. W. Martin, B. Welk, S. J. Kuhr. T. K. Ales, D. A. Brice, I. Ghamarian, A. H. Baker, C. V. Haden, D. G. Harlow, H. L. Fraser and P. C. Collins, "Predicting tensile properties of Ti-6Al-4V produced via directed energy deposition," *Acta Materialia*, vol. 133. pp. 120-133, 31 Jul. 2017, shows the roles of the various strengthening mechanisms of Ti-6Al-4V and their percent contribution to overall yield strength $\sigma_{ys}$ of the material. High melt pool temperatures, vacuum conditions and the relatively large melt pool (12 mm versus 50 µm) compared to other additive processes, make the loss of aluminum a significant problem, when depositing Ti-6Al-4V with EBAM. Given that the yield strength changes significantly with the change in aluminum content, this presents a problem for adoption of EBAM as a large scale process that can be used in high performance, low safety-margin applications, such as aerospace turbofan compressor rotors, high-performance turbocharger rotating assemblies, and liquid fuel turbopump rotating assemblies.

Being able to intelligently predict, understand, and compensate for possible solute loss during the EBAM build process is one of the key objectives highlighting the need for an integrated approach to understanding the material state in order to properly predict the properties and thus performance, and in so doing to provide designers and engineers with design allowables that exceed the minimum requirements imposed by a given application. The provision of such predicted design allowables will notably accelerate the qualification of unique processing routes that additively manufactured parts present, but also presents a new paradigm for the qualification of other processes that include both additive and more traditional manufacturing processes and procedures.

In the following is a discussion of experimental and computational techniques, beginning with metallographic sample preparation for the experimental techniques. The sample database used in this work was built initially for the research conducted on adapting a previously developed phenomenological model for wrought products for use with additively manufactured products. See B. J. Hayes, B. W. Martin, B. Welk, S. J. Kuhr, T. K. Ales, D. A. Brice, I. Ghamarian, A. H. Baker, C. V. Haden, D. G. Harlow. H. L. Fraser and P. C. Collins, "Predicting tensile properties of Ti-6Al-4V produced via directed energy deposition," *Acta Materialia*, vol. 133, pp. 120-133, 31 Jul. 2017. As mentioned earlier, the database includes a large number of samples spanning three post-deposition heat-treatments. The proposed nomenclature from A. H. Baker, P. C. Collins and J. C. Williams, "New nomenclatures for additively manufactured titanium alloys," *JOM*, vol. 69, no. 7. pp. 1221-1227, 1 Jul. 2017, will be referred to as in Table 1. Table 1 provides applicable proposed nomenclatures for additively-manufactured Ti-6Al-4V from this article.

TABLE 1

| | |
|---|---|
| AM-Stress-Relieved | A fully lamellar microstructure. The features present in the as-deposited condition remain, but may be coarsened. Spatial variation in the size and variants of $\alpha$ laths will remain. |
| AM-$\beta$ annealed | A fully lamellar microstructure, typically consisting of elongated prior $\beta$ grains with continuous grain boundary $\alpha$, and with $\alpha$-laths, existing as either colonies or basketweave. The spatial variation in the size and variants of $\alpha$-laths will likely be eliminated (assuming constant composition and grain size). |
| AM-$\alpha$ + $\beta$ Hot Isostatic Press (HIP) | Owing to the time and temperature details, these will be microstructurally similar to the AM-$\alpha$ + $\beta$ high-temperature anneal. The important difference is that internal pores will be closed during the HIP cycle and the secondary alpha will be coarser due to slower cooling rate from HIP temperature. |

Figure 6B:
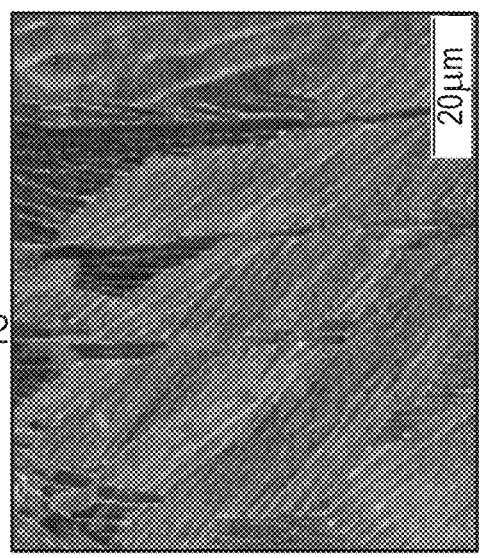
FIGS. 6A-C are back-scattered electrons images of the three microstructures in order of decreasing yield-strength from FIG. 6A to FIG. 6C.
Figure 6C:
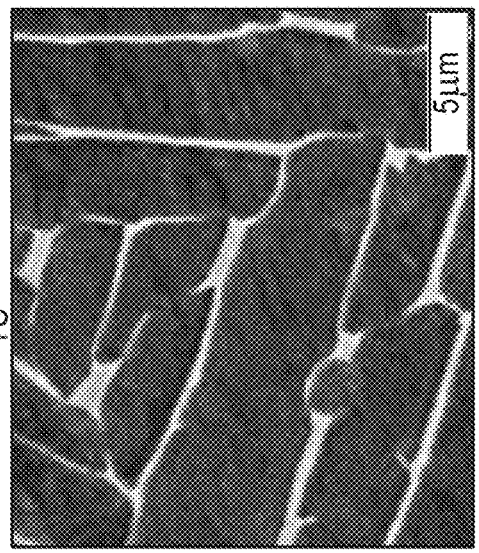
Figure 6A:
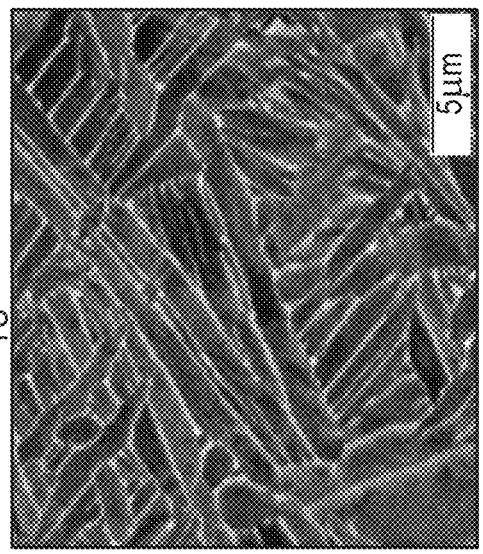

These terms in Table 1 better reflect the actual processing that is encountered during a workflow involving an additively manufactured component compared to the typical labels. "as-received," "mill anneal," and "$\beta$-annealed" that are encountered in traditional thermomechanical processing routes. Representative micrographs along with their associated average $\sigma_{ys}$ are given in FIGS. 6A-C. FIGS. 6A-C are back-scattered electrons (BSE) images of the three microstructures discussed in Table 1, in order of decreasing yield-strength left to right (6A to 6C). Note the scale of the center image is 20 microns as compared to the left and right image's scale of 5 microns.

The samples come from three different heat treatments, given below roughly in order of decreasing yield strength ($\sigma_y$). First, shown in FIG. 6A is the AM-stress-relieved treatment condition, in which a part is exposed to elevated temperatures, but well below any microstructurally active region in order to lower stress gradients induced by the build process. Notably, the dislocation density is still high for the AM-stress-relieved condition. See B. J. Hayes, B. W. Martin. B. Welk, S. J. Kuhr. T. K. Ales, D. A. Brice, I. Ghamarian, A. H. Baker. C. V. Haden. D. G. Harlow. H. L. Fraser and P. C. Collins, "Predicting tensile properties of Ti-6Al-4V produced via directed energy deposition." *Acta Materialia*, vol. 133, pp. 120-133, 31 Jul. 2017. Second, shown in FIG. 6B is the AM-β-annealed treatment, where the part is held at a high-temperature, allowing the growth of large α-colonies. Finally, in FIG. 6C, AM-α+β hot isostatic press (HIP) is shown, in which the part is subjected to high-pressures and temperatures in the α+β phase field after the build in order to remove defects and stresses accumulated during build process. This high temperature and pressure eliminates the high dislocation densities when compared to the AM-Stress-Relieved condition, with reported densities on the order of $10^{15}$ m$^2$.

Sample preparation workflow includes the samples contained within the database were prepared using standard metallographic practices. Samples were taken from precisely located positions of the build in the form of substandard ASTM round tensile blanks, described in ASTM E8/E8M of ASTM International, "Standard Test Methods for Tension Testing of Metallic Materials," ASTM International, West Conshohocken, 2014, with a gage diameter of 0.250".

Following the tensile tests, which were performed by Westmoreland Mechanical Testing & Research (WMT&R), the longer half of the tested sample was selected for examination, and sectioned on a low-speed diamond saw, with a minimum thickness of 0.200" and at least 0.100" away from any visible necked region in order to minimize the influence of material plasticity on the microstructure. If this was not possible in the gage section, the sample was taken from the thread section and then the samples were mounted in conductive phenol (Buehler Konductomet) using a 1.25" diameter hot-press in groups of three, with unique geometric keys cut into each sample to identify it within the metallurgical puck.

Between four and ten images were taken in backscatter mode with locations chosen at random, until the figures of merit described in, P. C. Collins, B. Welk, T. Searles, J. Tiley and H. L. Fraser, "Development of methods for the quantification of microstructural features in α+β-processed α/β titanium alloys," *Materials Science and Engineering*: A, vol. 508, no. 1-2. pp. 174-182, 20 May 2009, were met. These merit figures were set at a coefficient of variation (CoV) of $\overline{X}_{VF\alpha} \leq 3.0\%$ for the α-phase volume fraction, and $\overline{X}_{\alpha\text{-}lath} \leq 10.0\%$ for the α-lath width variation and were then processed using the commercially available Materials Image Processing And Reconstruction (MIPAR™) package (See J. Sosa, D. E. Huber. B. Welk and H. L. Hamish, "Development and application of MIPAR™: a novel software package for two- and three-dimensional microstructural characterization," *Integrating Materials and Manufacturing Innovation*, no. 3:10, December 2014).

To determine the volume fraction of the alpha phase, the properties of backscatter images were utilized. In Ti-6Al-4V, the α phase is darker than the β phase due to the difference in average atomic number Z within the two phases, as α stabilizers tend to be atomically lighter than β stabilizers for titanium, with tin being the notable exception to the rule. See, R. Boyer. G. Welsch and E. W. Collings. Materials Properties Handbook: Titanium Alloys, ASM International, 1994. MIPAR™ is able to threshold and identify these regions in a batch manner once an appropriate recipe has been designed for the typical imaging condition.

Figures 7A, 7B:
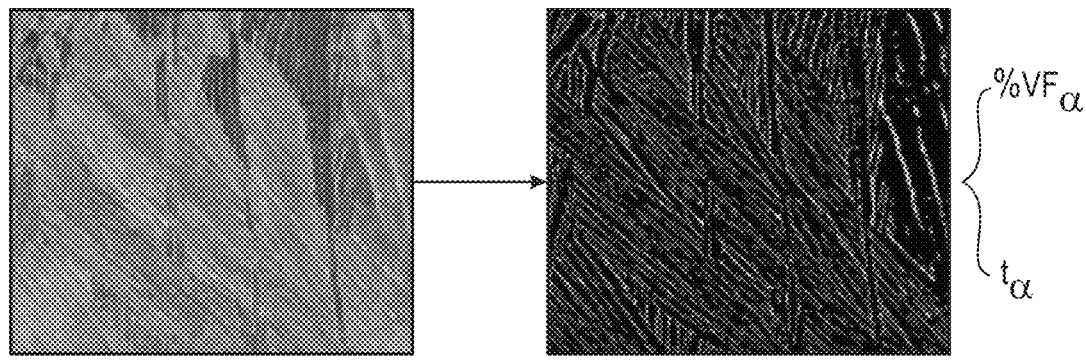
FIG. 7A provides a backscatter image acquired showing typical β-anneal morphology.
FIG. 7B shows a thresholded version of the same image of FIG. 7A.

FIG. 7A shows a backscatter image acquired showing typical β-anneal morphology. FIG. 7B shows a thresholded version of the same image of FIG. 7A. Light colored pixels are the β phase, and black pixels are the α phase.

EDS spectra were also acquired during the imaging of each sample. These spectra were deconvoluted against the default standards native to the Oxford AZtec software package. Each run was allowed to acquire 5M counts at the standard 'Process Time' setting of 4 with Pulse Pile-Up Correction enabled. This information was used in conjunction with chemical testing provided by Luvak Laboratories to provide location-specific chemistry for each sample. Table 2 provides a summary of the imaging and EDS conditions.

TABLE 2

| Parameter | Setting |
| --- | --- |
| Accelerating Voltage | 15 kV |
| Spot Size (FEI) | 4.0 |
| Dwell | 30 microseconds per pixel |
| Resolution | 2048 px FET × T preset |
| Working Distance (EDS + BSE) | 10.0 mm |
| Final Aperture | 30 microns |
| EDS Process Time | 4 |

The BSE images then were processed in MIPAR™. From these images, the volume fraction of the α-phase present, along with the α-lath thickness was extracted from each image and used to compile statistical information for each sample.

Morphology was examined using optical microscopy. Once the samples were satisfactorily examined and characterized in the electron microscope, they were etched in a bath of Kroll's Reagent for 10 to 15 seconds. This etching allowed for optical imaging of each sample. For the prior-beta grain factor (PBGF), one large overview mosaic was taken using an Olympus GX20 in brightfield mode at 5× magnification. Several more images were taken at 200× magnification to establish the percentage of α-colony present, and the colony scale factor (CSF) for the sample using stereographic techniques suitable for the task. The stereological analysis of optical images was completed in the commercially available software package, Adobe Photoshop CC, using a set of plugins known as Fovea Pro. The Fovea Pro plugins have now been superseded by QIA-64, but provide similar functionality. QIA-64 is available from Reindeer Graphics, Inc.

Computational techniques can include finite-element analysis (FEA) of the thermal problem discussed herein. Due to the complex nature of the thermal history of an additively manufactured part compared its traditionally-processed counterpart, numerical simulation is invoked. This is due to the unique and complex thermal nature of the build itself, the part-dependent thermal profile and the relatively complex geometries as compared to a traditional forging model, which may just involve a cylinder of a specified geometry, at an isothermal hold and a known, or desired reduction in area.

To get the part-dependent thermal solution, the ABAQUS FEA package can be used, which is commercially available from D'assault Systemes. The ABAQUS package is known for its user-extensibility through FORTRAN and C subroutines and general-purpose design.

Figure 8:
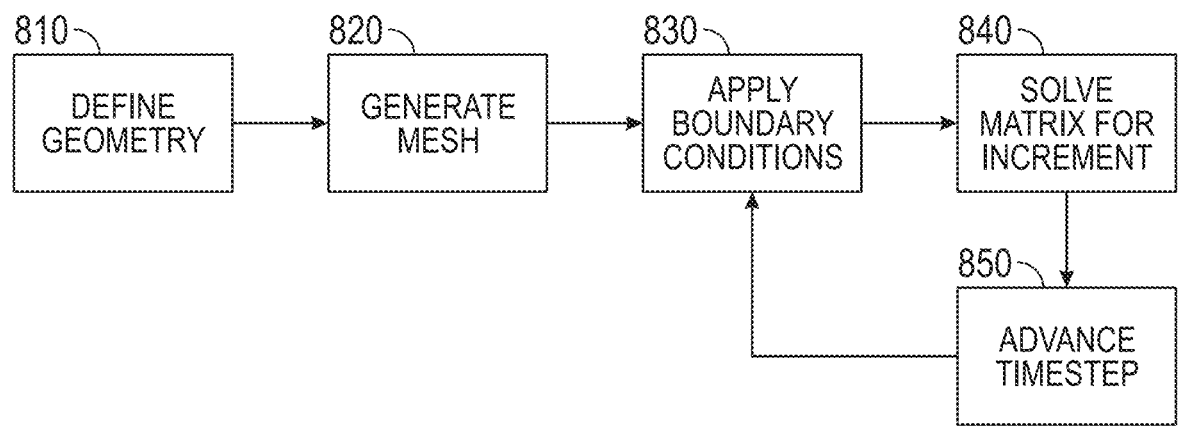
FIG. 8 is a simplified overview of a finite-element method workflow.

The finite-element method can be summarized as follows: a geometry of interest is modeled, either internally to the finite element package or externally in another CAD program, such as CATIA, SolidWorks, or Inventor. This serves as a basis for the meshing software to create a discretized mesh to operate on. Boundary conditions are specified either through direct specification in the case of constant temperatures, fluxes, etc., or they are prescribed through the use of user subroutines. FIG. 8 is a simplified overview of a finite-element method workflow. At 810, geometry is defined. At 820, a mesh is generated. At 830, boundary conditions are applied. At 840, a matrix is solved for increment. At 850, a time step is advanced with return to 830.

For the process model, a direct symmetric solver is invoked within ABAQUS, which uses Newton's method to handle the non-linear portion of the simulation, with a Gaussian elimination method for the linear portion to solve the basic energy balance equation given below in Equation 1. See D'assault Systemes, Abaqus Theory Guide. D'assault Systems, 2017, p. 2.11.1. The left hand side of equation 1 represents the internal energy of the system, $$\int_V \rho \dot{U} dV = \int_S q dS + \int_V r dV \qquad \text{Eq. 1}$$

where the density, $\rho$, is multiplied by the change in internal energy ($\dot{U}$) of the control volume (dV). In this equation, V is a volume of a body, S is the surface area of the body, q is the heat flux per unit area of the body, and r is the heat supplied internally into the body per unit volume. To handle the time integration in an uncoupled analysis. ABAQUS uses a backwards-difference algorithm, which allows the internal energy of the system to be described as the change in system energy between the two increments, and then scaled appropriately in Eq. 2:

$$\dot{U}_{t+\Delta t} = (U_{t+\Delta t} - U_t)\left(\frac{1}{\Delta t}\right) \qquad \text{Eq. 2}$$

For uncoupled heat transfer, ABAQUS assumes that the system's internal energy is only controlled by temperature, but not any mechanical effects. ABAQUS then can describe the internal system energy through specific heat, defined as the change in energy (dU) with respect to the change in temperature (d$\theta$):

$$c_p(\theta) = \frac{dU}{d\theta} \qquad \text{Eq. 3}$$

With the system defined. ABAQUS uses the Galerkin method to discretize the geometry that was specified during the setup of the problem. It then solves the system of equations until the appropriately specified error residual is reached or the maximum number of iterations has been reached for the increment. The time-step is determined by the user through the specification of the maximum allowable temperature increase in the increment. Currently, models are setup to capture frames every 100 ms, while incrementing at approximately 1 ms during deposition events. During cooling events the models report and increment at 500 ms. In ABAQUS, this is controlled by specifying a 300 K maximum increase per increment in the setup of the step.

One caveat of using ABAQUS is that it is not a unit-aware FEA package, so the onus is on the operator to ensure that they are using a self-consistent system of units. In the case of this work, all input values were converted to the SI mks (meter-second-kilogram) system. Although many values will be given in the unit system they were taken in (e.g., beam diameter is reported in inches due to it being recorded in inches), values in the source code and other utilities should be assumed as mks. The only modification to these assumed units is energy, in which the assumed unit should be kilojoule or kilowatt instead of joules or watts, respectively.

Consider the additive process model, where model inputs can include the Goldak heat source. The process model can utilize the Goldak double-ellipsoidal heat source (See J. Goldak. A. Chakravarti and Bibby Malcom, "A New Finite Element Model for Welding Heat Sources," *Metallurgical Transactions B*, vol. 15B, no. June 1984. pp. 299-306, 1984) to model the electron beam as an asymmetric ellipsoid. The Goldak source was initially used for the modeling of electron beam welding, and captures the profile rather well. Other heat source models exist, such as the Rosenthal solution, but was not chosen due to the Rosenthal solution assuming the form of a point source (See A. Lecoanet, D. G. Ivey and H. Henein, "Simulation of the Temperature Profile During Welding," in *COMSOL Conference*, Boston, 2014). Being able to customize the shape of each individual quadrant of the beam intensity distribution makes it a good choice for electron beam based processes that allow for fairly arbitrary distributions. For example, the beam does not need to be symmetric or uniformly distributed. The model can be implemented within the DFLUX subroutine of ABAQUS.

The computation of the heat source can be a two-step process. First, a coordinate transform can be performed to determine the position of the beam origin, as shown in equations 4-6:

$$x' = x_0 + v_x t \qquad \text{Eq. 4}$$

$$y' = y_0 + f(\text{step}) \qquad \text{Eq. 5}$$

$$z' = z_0 + v_z t, \qquad \text{Eq. 6}$$

where x', y', and z' represent the current position of the beam in the global coordinate system as a function of the velocities $v_x$, and $v_z$, which are piece-wise polynomials that represent the motion of the beam. The layer height is controlled by the function $f(\text{step})$, which is coded for each specific geometry. Depending on how the steps within ABAQUS are logically organized and linked to the actual change in layer determines the approach one takes when developing the $f(\text{step})$ equation. Second, the flux field is calculated based on the beam origin. The power densities are given by Equation 16 in J. Goldak, A. Chakravarti and Bibby Malcom, "A New Finite Element Model for Welding Heat Sources." *Metallurgical Transactions B*, vol. 15B, no. June 1984, pp. 299-306, 1984 and is adapted for use in the model as Eq. 7 below. The power distribution function uses the determination of three characteristic length values: a, b, and c, which correspond to the x, y and z axes of the heat source ellipsoid. The layer geometry measured approximately 0.50" in width, and 0.25" in thickness, so these values were used directly, and are shown in Table 2.

Information regarding the suitable front and rear hemisphere characteristic values was not available, so the advice provided by Goldak, et. al. reference above, was followed: "In the absence of better data, the experience of these authors suggests it is reasonable to take the distance in front of the heat source equal to one-half the weld width and the distance behind the heat source equal to twice the weld width." Regarding the front to rear power split, Goldak's approach was similarly taken: "Values of $f_f$=0.6 and $f_r$=1.4 were found to provide the best correspondence between the measured and calculated thermal history results." Shown below in Eq. 7 is the heat flux (q) as a function of the global beam origin position. Q represents the magnitude of the beam, and $f$ is the distribution fraction, which should sum to 2.

$$q(x', y', z') = \frac{6\sqrt{3}\, fQ}{abc\pi\sqrt{\pi}} \exp\left[-\frac{(3x')^2}{a^2}\right] \exp\left[-\frac{3y'^2}{b^2}\right] \exp\left[-\frac{3z'^2}{c^2}\right] \qquad \text{Eq. 7}$$

Table 3 shows typical values used in all process models.

TABLE 3

| Symbol | Measured Value | Calculated Value |
|---|---|---|
| Q | 8200 W | — |
| a/$r_{beam}$ | 0.250 in | — |
| b | 0.125 in | — |
| $c_{front}/c_{rear}$ | — | 0.250"/1.000" |
| $v_{avg}$ | 30 inches/minute | — |

Figure 9:
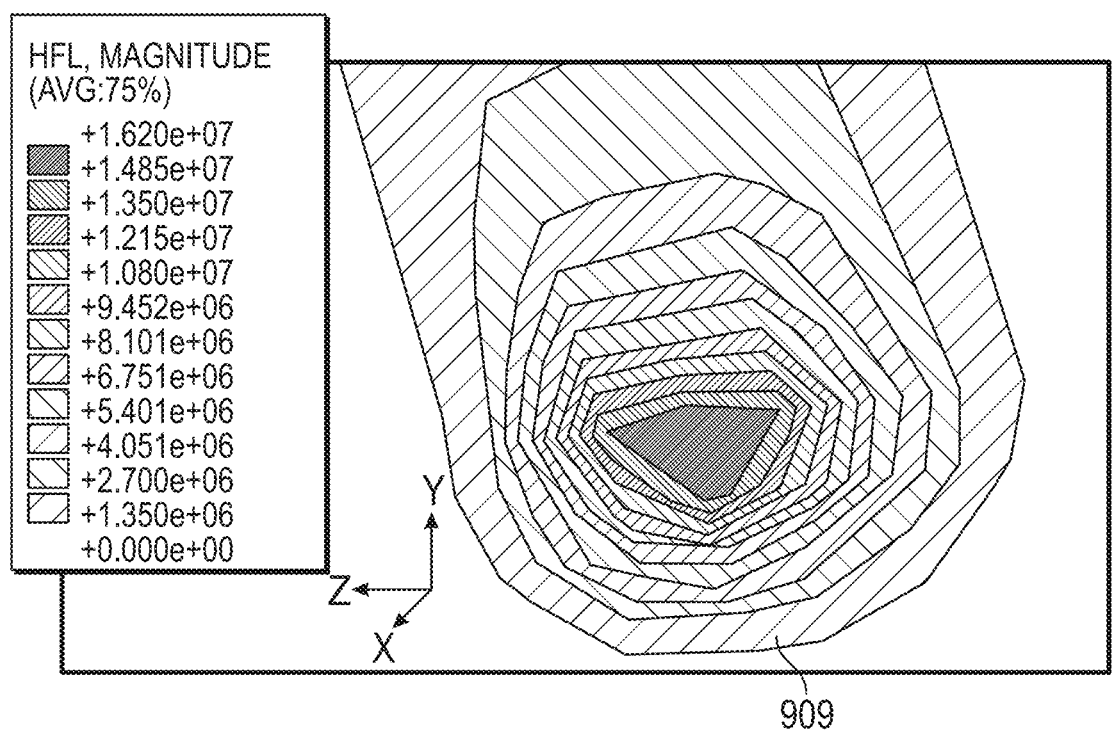
FIG. 9 depicts a simulation that has incorporated a Goldak heat source distribution.

FIG. 9 depicts a simulation showing a Goldak heat source distribution. The simulation is an ABAQUS simulation. The distortion of the zero-flux isosurface on the left side of the image when compared to the right side is due to inactive elements and not the heat source itself. This figure provides a visualization of the heat source in W/m³. The ABAQUS state variable HFL ("Heat FLux") is used to visualize the flux field, where isosurface 909 represents 0 W/m³. As shown in FIG. 9, some of the known issues of using the "quiet element" method, described in P. Michaleris, "Modeling metal deposition in heat transfer analyses of additive manufacturing processes," *Finite Elements in Analysis and Design*, vol. 86, pp. 51-60, 2014, are visible. Because ABAQUS and other FEA packages interpolate between node points, any element that is inactive but immediately adjacent to another element will have a temperature error and also a heat flux error due to the sudden scaling of the specific heat and thermal conductivity. Meshing should be done with care in order to minimize the error zone, but also can be minimized through careful selection of $k_s$ and $C_{p,s}$ as described in the abovementioned article by Michaleris.

The input power (Q) was determined via build telemetry supplied by Sciaky, Inc. and was calculated as the average product of the measured input voltage on the beam and measured current in the workpiece. An average velocity of 30 inches per minute was also observed in the data. However, acceleration and deceleration of the head was not taken into account. Physical dimensions of the layers were measured on a thinwall specimen. Small adjustments were made to the flux distribution functions until the expected peak melt pool temperatures were observed. Using the above guidance provided in J. Goldak, A. Chakravarti and Bibby Malcom. "A New Finite Element Model for Welding Heat Sources," *Metallurgical Transactions B*, vol. 15B, no. June 1984, pp. 299-306, 1984, there was approximately a −400K differential between the simulated and expected peak melt pool temperatures. The distribution was successively shrank, so that the peak temperature would increase. It was found that setting a/$r_{beam}$ equal to 0.200" gave good agreement with the expected peak pool temperature.

The heat source can be realized through the ABAQUS user subroutine DFLUX. DFLUX allows for specification of arbitrary, point, surface and volume fluxes within a simulation domain.

Modeling can include modeling the solid-to-liquid transition. If the value of the latent heat of fusion is known, and the freezing range of the alloy is also known, the calculation of the effective specific heat is a straightforward exercise and computationally efficient, shown in Eq. 8 of D'Assault Systemes. "Abaqus Theory Guide: 2.11.1: Uncoupled heat transfer analysis," D'Assault Systems. For Ti-6Al-4V, values of 330 kJ/kg for $\Delta h_f$ and 10K for $\Delta T_f$ were used from M. Boivineau, C. Cagran, D. Doytier, V. Eyraud and M. Nadal, "Thermophysical Properties of Solid and Liquid Ti-6Al-4V (TA6V) Alloy," *International Journal of Thermophysics*, vol. 27, no. 2. March 2006. This leads to an effective heat capacity of approximately 33 kJ/kgK for the solidification event. With this information, the full thermal profile can be simulated, as shown in FIG. 9 of the above-mentioned article by Boivineau et al. As the point cools from the peak melt temperature, only sensible heat is lost, as the upper end of the freezing range is reached, the effective heat capacity is used to account for the correct amount of latent heat required to solidify the material.

$$c_p^* = \frac{dU}{d\theta} = \frac{\Delta H_f}{\Delta T_f} = 33 \frac{\text{kJ}}{\text{kgK}} \qquad \text{Eq. 8}$$

Table 4 shows typical values used in simulations for modeling the solid-to-liquid transition, taken from M. Boivineau, C. Cagran. D. Doytier, V. Eyraud and M. Nadal, "Thermophysical Properties of Solid and Liquid Ti-6Al-4V (TA6V) Alloy," *International Journal of Thermophysics*, vol. 27, no. 2. March 2006.

TABLE 4

| Symbol | Typical Value |
|---|---|
| $T_{melt}$ | 1933K |
| $\Delta T_f$ | 10K |
| $\Delta h_f$ | 330 kJ/kg |
| $c_{p,s}$: T < $T_{melt}$ | $c_{p,s}(T) = (8 \cdot 10^{-5})T + 0.7019$ |
| $c_p^*$: $T_{melt}$ < T < $T_{melt}$ + $\Delta T_f$ | $c_p^*$ = 33.0 kJ/kgK |
| $c_{p,l}$: $T_{melt}$ + $\Delta T_f$ < T | $c_{p,l}(T) = (-6 \cdot 10^{-6})T + 1.1441$ |

Figure 10:
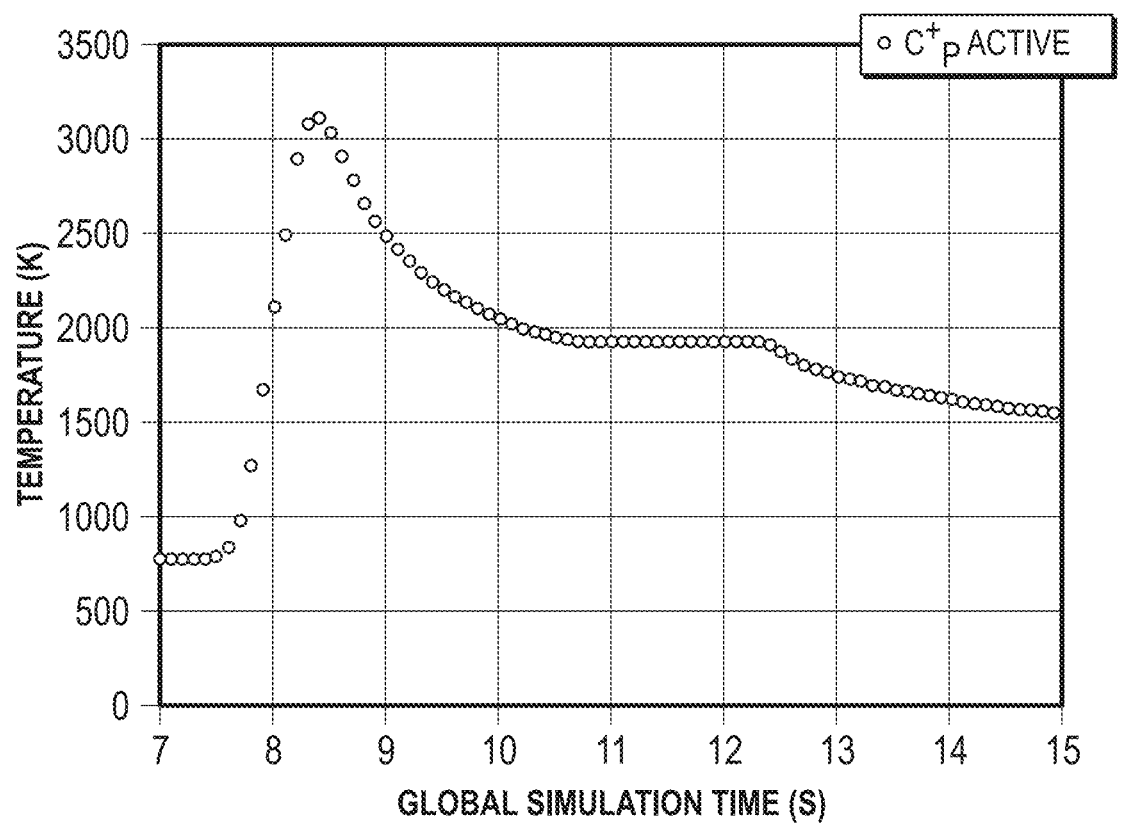
FIG. 10 illustrates a thermal profile showing the effect of effective heat capacity, cp*.

Once through the solidification event, the solid heat capacity equation takes over and resumes modeling the heat capacity. This approach can also be used to take into account any exothermic or endothermic effects from phase changes in other alloys or material systems. FIG. 10 illustrates a thermal profile showing the effect of cp*.

Other thermal boundary conditions can be considered. Another significant contributor to the character of the thermal profile seen in the EBAM process is the loss of heat energy via radiation. In ABAQUS, this is modeled using the Stefan-Boltzmann relationship for radiation loss, shown in Eq. 9. The primary value that controls the loss rate is the emissivity ($\epsilon$), set here to a constant value of 0.77 for titanium. ABAQUS abstracts the contribution from the Stefan-Boltzmann constant and the emissivity value ($\sigma$=5.67·10⁻⁸ W/m²K⁴) into a single constant (A) (See T. J. Quinn and J. E. Martin, "Aradiometric determination of the Stefan-Boltzmann constant and thermodynamic temperatures between −40 C and +100 C," *Philos. Trans. R. Soc. London Ser. A*, vol. 316, no. 1536. pp. 85-189, 1985). $\theta$ is the surface temperature, and $\theta$° is the infinite sink temperature.

$$A = \sigma \in;\ q_r = A(\theta^4 - \theta^{0^4});\ \frac{\delta q}{\delta \theta} = 4A\theta^3 \qquad \text{Eq. 9}$$

Use can be made of the "hybrid quiet inactive element" method. The "hybrid quiet inactive element," method proposed and outlined in E. R. Denlinger, J. Irwin and P. Michaleris. "Thermomechanical modeling of additive manufacturing large parts." *Journal of Manufacturing Science and Engineering*, vol. 136, no. 6, p. 061007, 1 Dec. 2014 is now part of the ABAQUS/2017 core functionality and is handled by the user subroutine UEPACTIVATION-VOL. It is worth going over however at a high level, as the process may not be intuitively obvious at first.

The ABAQUS software package does not allow for the *MODEL CHANGE keyword to be used in steps that have the *PROGRESSIVE ELEMENT ACTIVATION keyword active in the same step. The method in P. Michaleris, "Modeling metal deposition in heat transfer analyses of additive manufacturing processes," *Finite Elements in Analysis and Design*, vol. 86. pp. 51-60, 2014 used inactive elements to speed computational time on initial layers, and quiet elements to efficiently model the deposition of material. An approach used herein only involves the quiet elements, and not any inactive elements. Inactive elements can be removed from the model, which can significantly speed computational time up. The quiet elements are present, but characterized by having significantly lower $c_p$ and k values as compared to a normal finite-element.

$$c_{p,quiet} = s_{c_p} c_p \quad \text{Eq. 10}$$

$$k_{quiet} = s_k k \quad \text{Eq. 11}$$

According to P. Michaleris, "Modeling metal deposition in heat transfer analyses of additive manufacturing processes." *Finite Elements in Analysis and Design*, vol. 86. pp. 51-60, 2014, scaling factors of approximately $s_k = 1 \cdot 10^{-4}$ for the quiet element's thermal conductivity and $s_{cp} = 1 \cdot 10^{-2}$ for the specific heat scaling provided the best balance between activation error and stability of the Jacobian contribution for $s_{cp}$ and $s_k$ respectively, contributing an error of less than 0.25% compared to if the elements were left in the activated state.

Figure 11:
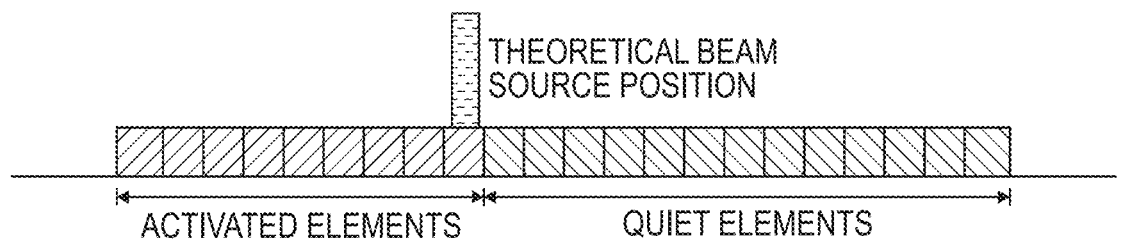
FIG. 11 is a schematic showing how a subroutine models deposition of material.
Figure 12:
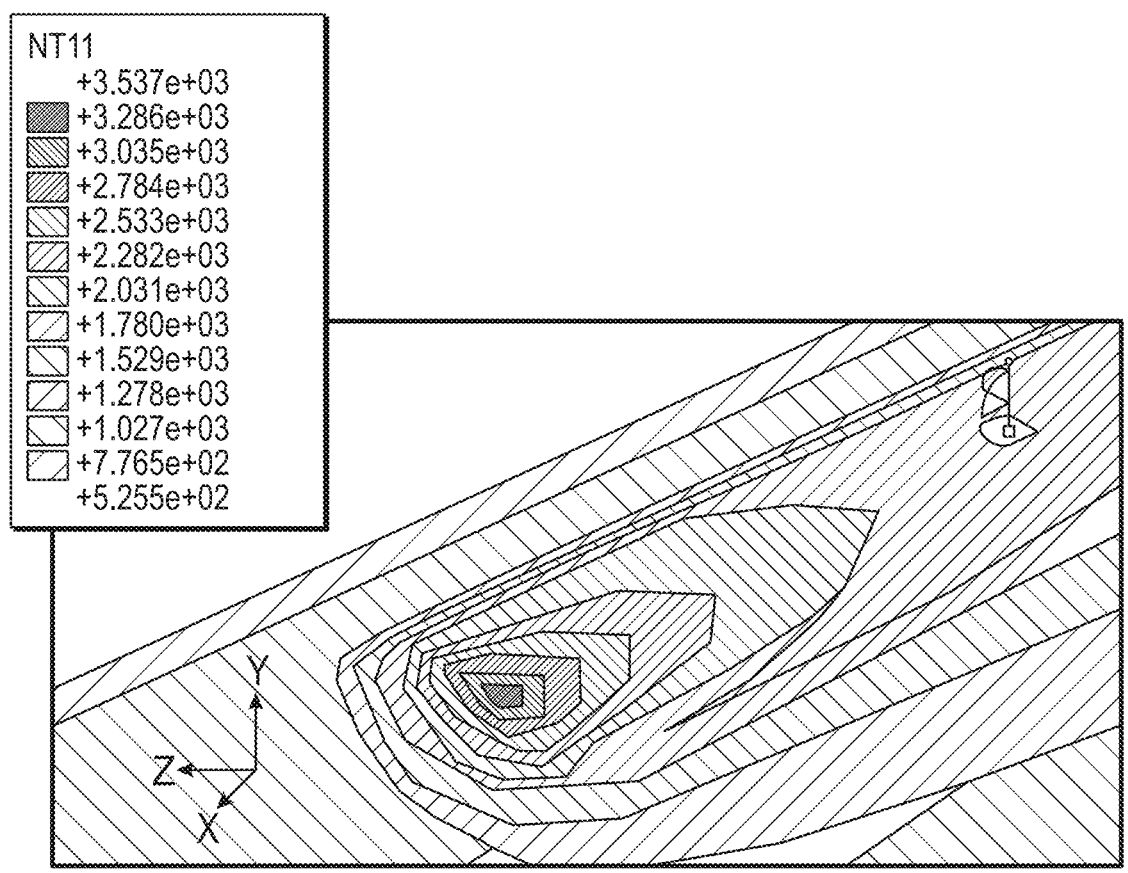
FIG. 12 shows a nodal temperature distribution, as a nodal temperature output, for a thickwall simulation.

The simulation determines which elements to activate by first determining the position of the beam within the current layer, and proceeds to activate all elements that are within the build domain, but behind the current beam position along the build path. FIG. 11 is a schematic showing how the UEPACTIVATIONVOL subroutine models deposition of material. Schematically illustrated in FIG. 11, are activated elements on one side of a theoretical beam source position, while on the other side of the theoretical beam source position are elements have been quieted. Once this is complete, a search for any build elements that are below the current layer plane is performed, and all found elements are activated before running the simulation for that increment. FIG. 12 shows a NT11 (nodal temperature) distribution, as a nodal temperature output, for a thickwall simulation, and shows how the quiet elements prevent any heat transfer into the inactive layer. The isosurfaces show the inactive elements forming a barrier to the beam directly ahead of the beam center, and on the far side of the layer.

Once an element is activated, it is no longer considered by the UEPACTIVATIONVOL subroutine if the element ends up in another search. In ABAQUS, each deposition step and cooling step for the layer is segmented into its own "Step" in the simulation. This provides a logical break using the TIME (2) component of the TIME array. In ABAQUS, TIME (1) is the global simulation time, and TIME (2) is the step simulation time. By allowing each layer to have its own deposition and cooling step, one can infer which step the simulation is on by doing a simple modulo division operation on the step number indicator, KSTEP. If KSTEP is odd, a deposition event is occurring, and the current layer should be activated in a progressive manner. If KSTEP is even, an interlayer cooling event is occurring, and the current layer should be fully activated so it can simulate the cooling that would occur in the actual build process as the deposition head returns to the home position.

Figure 13A:
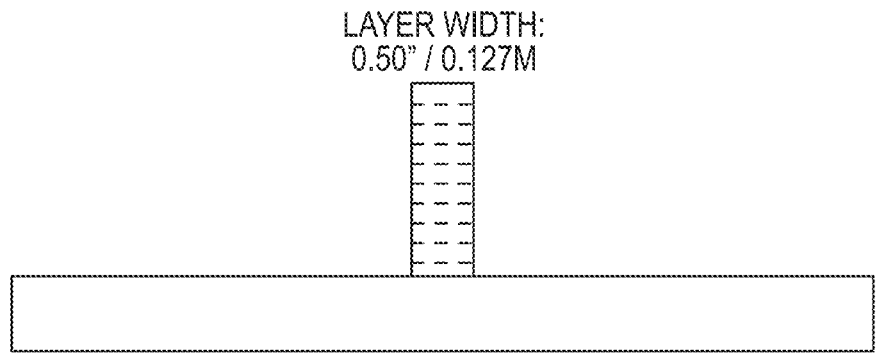
FIGS. 13A-B are schematic representations of the thinwall build geometry.
Figure 13B:
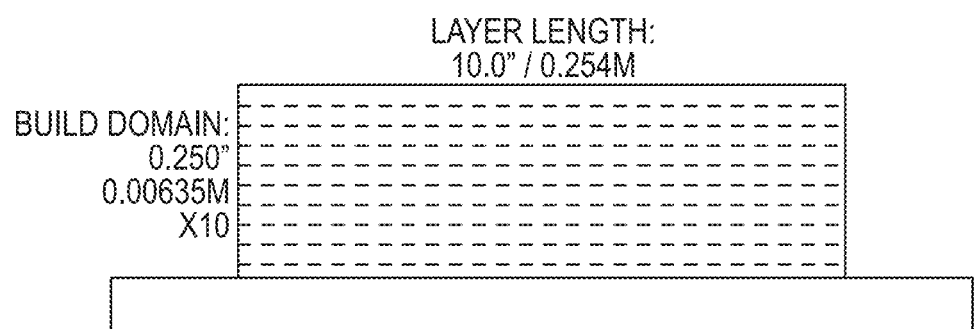

Modeling can include application of a geometric configuration. Two configurations are presented in this work that are relevant to the EBAM process. In an example, the thinwall geometry consists of a 12"×12"×1" plate acting as the substrate. Ten layers with a geometry of 10"×0.50"×0.25" are deposited to the center of the plate as shown in FIGS. 13A-B. FIGS. 13A-B are schematic representations of the thinwall build geometry, with FIG. 13A illustrating layer width and FIG. 13B illustrating layer length. This geometry was chosen due to thinwall structures having a significant presence in additively manufactured components. The thinwall should also exhibit the highest cooling rates that the process should see as the substrate acts like a large thermal reservoir causing the first layer to cool significantly quicker than others. The small thermal mass of the single-pass thinwall structure compared to the volume of the heatsink amplifies this effect.

Figure 14A:
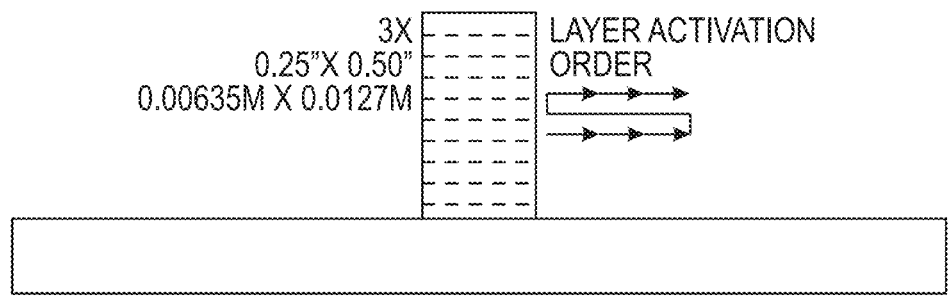
FIGS. 14A-B are schematic representations of the thickwall build geometry.
Figure 14B:
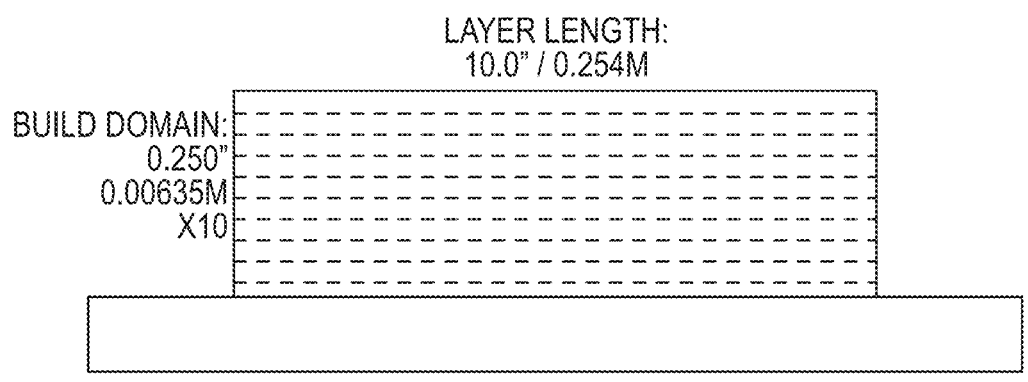

The second geometry presented is what is referred to as a thickwall build section and consists of three layers deposited side by side. This geometry stalls the cooling rates through the microstructurally active regions for longer compared to the thinwall geometry. FIGS. 14A-B are schematic representations of the thickwall build geometry. A schematic representation of the thickwall build domain is shown in FIGS. 14A-B with the individual layers traced out by the dashed lines. FIG. 14A illustrates layer width and FIG. 13B illustrates layer length. The activation order of each layer proceeds from left to right in the schematic side view.

Between each layer, an interlayer cooling time is provided to mimic the return of the head to the home position before deposition of the next layer. In these simulations, the interlayer cooling time has been set equal to that of the layer deposition time. For example, if a deposition takes 20 seconds, the total layer time, with the interlayer cooling time is 40 seconds.

From telemetry supplied by Sciaky. Inc. an average deposition speed of 30 inches per minute has been determined. For the 10" long builds that are modeled in this simulation, this leads to global simulation times of 420 seconds for a thinwall build, and 1,260 seconds for the thickwall build.

Modeling can include a motion control model. The motion controls were coded on a per case basis, but take the same overall modeling approach. In each case, the ABAQUS concept of a "Step" is used to control the current layer deposition. Repetitive motion is then modeled using modulo division in order to allow for arbitrary and infinite periodicity.

There are thinwall build considerations. The thinwall configuration breaks deposition and cooling pass into their own ABAQUS "Step." As previously described, an odd/even test is performed to determine if the step is a deposition or cooling step. The layer position is controlled by a function that takes the current simulation step and calculates the nearest integer layer. This function is given below in Eq. 12, where NINT( ) is a FORTRAN function that returns the nearest integer. KSTEP is the ABAQUS environment variable that indicates the current layer step. This behavior is shown in FIG. 15.

LayerNo=NINT(0.5*REAL(KSTEP)+0.5)   Eq. 12

Figure 15:
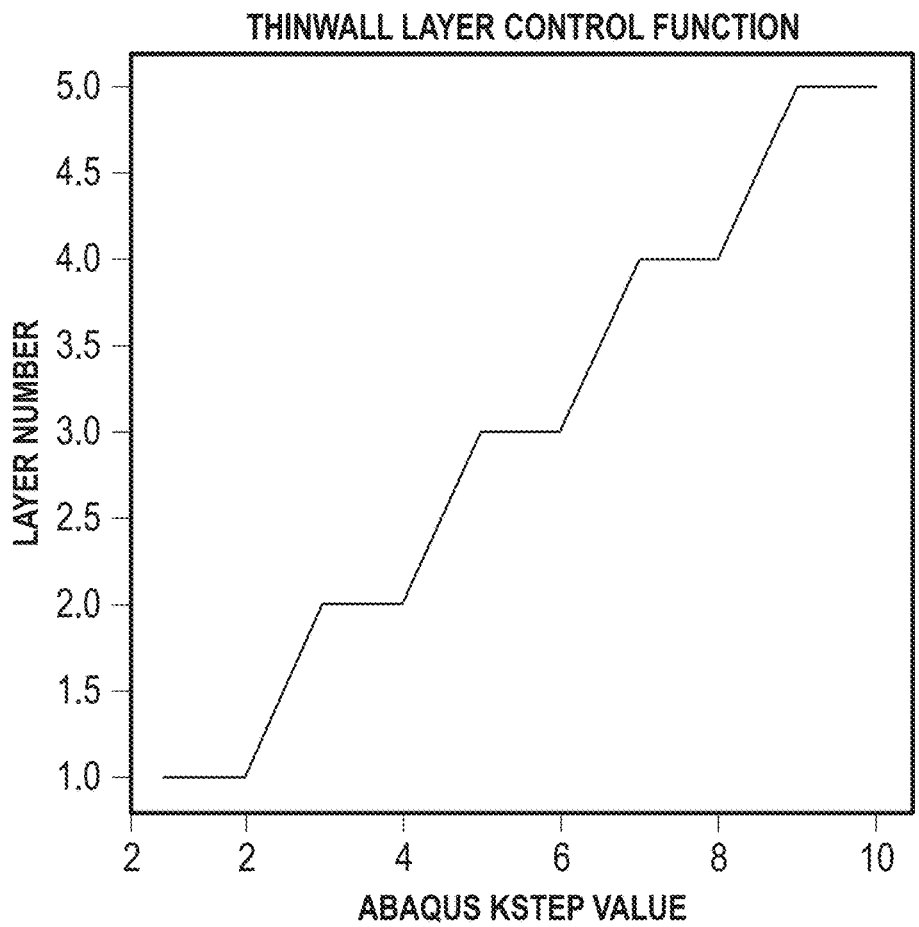
FIG. 15 is a plot showing the implementation of an equation in a simulation of the layer position in thinwall layer control.

FIG. 15 is a plot showing the implementation of Eq. 12.

Because each deposition and cooling stage is broken into its own step, and the only direction of motion is in the global x-direction, the step time, TIME (2) is used to provide the periodicity required by the motion equations. At the end of each step, TIME (2) returns to zero, and the beam position is returned to the home position.

There are thickwall build considerations. The thickwall build has some unique challenges associated with it that use a different approach to how each layer is broken up into steps compared to the thinwall. Taking the same approach as the thinwall geometry would create 60 steps, which then each require their own logic code, boundary conditions, interactions and other specifications to be provided. In order to keep the number of steps for these proof-of-concept models low, an approach that exploits modulo division was taken. In an example, a thickwall layer was taken as 1.5" wide, it can be thought of as three 0.5" thinwall layers placed side by side. Time-wise is also the same as depositing three thinwall layers, which would take 126 seconds if one assumes the same interlayer cooling time as the thinwall. By setting each step in ABAQUS to represent the deposition of an entire thickwall layer means the motion is to be described in two dimensions. The first motion parameter that is determined is the z parameter. The z parameter is a way of describing which of multiple parallel deposition paths is the current one under consideration within the same layer. Multiple parallel "hatches" (or deposition paths) are required to make a "thick part", as opposed to a thin wall (single pass for every layer). Commercial models, such as ABAQUS, typically define their axes such that z is the thickness. By dividing the current step time (2) by the time it takes a thinwall layer to deposit (in this case 42 seconds) and then flooring that value to the nearest integer allows for simple case logic or if logic in the UEPACTIVATIONVOL subroutine. The values are provided in Table 5. Table 5 includes values for a Z-Offset flag and corresponding window dimensions. The Z-offset is effectively the pass with the first pass being zero, the second pass being 1, the third being 2 . . . the N−1 pass being the $N^{th}$. The lower Z bound is one of two bounds to the molten pool in the model in the z direction, which is the thickness direction, and the upper Z bound is the second of two bounds to the molten pool in the model. The difference between the lower Z bound and upper Z bound is the width of the molten pool, or at least the width of the "hatch," as set into the machine code controlling the motion of the deposition system.

TABLE 5

| Z-offset flag | Lower Z bound | Upper Z bound |
| --- | --- | --- |
| 0 | −0.75" | −0.25" |
| 1 | −0.25" | 0.75" |
| 2 | 0.25" | 0.75" |

The next consideration is moving the beam along the x-axis, knowing from the thinwall build that it takes about 21 seconds to traverse the layer, and another 21 seconds to cool. By dividing TIME(2) by modulo 42, the cooling and deposition steps can be handled in one line of code. The first 21 seconds deposit as normal, the next 21 seconds, the beam is outside of the layer domain boundary and is ignored. Although this is not the most efficient method, it is very simple to implement and ABAQUS' temperature driven time-stepping algorithm allows for simulating both the deposition step at 1 ms, then the cooling steps at 500 ms. The computational penalty is acceptable for demonstration purposes, one would want to more efficiently model the cooling steps, and allow ABAQUS to skip calculating the volume flux load.

Presently motion controls are developed on a case by case basis for each geometry one wishes to investigate when using this method. While this is acceptable for research purposes, where the cases are idealized, a g-code translator can be developed that would allow limited investigation of potential hot-spots and 'bad' geometric configurations on a case-by-case basis.

This could be achieved either through the Python or C APIs that ship with ABAQUS. Taylor hardening was recently added to the phenomenological equation in P. C. Collins, C. V. Haden, I. Ghamarian, B. J. Hayes, T. Ales, G. Penso, V. Dixit and G. Harlow, "Progress Toward an Integration of Process-Structure-Property-Performance Models for "Three-Dimensional (3-D) Printing" of Titanium Alloys," *JOM*, vol. 66, no. 7, pp. 1299-1309, July 2014, and was a refinement of what was a somewhat arbitrary basketweave factor in P. C. Collins, C. V. Haden, I. Ghamarian, B. J. Hayes. T. Ales, G. Penso, V. Dixit and G. Harlow, "Progress Toward an Integration of Process-Structure-Property-Performance Models for "Three-Dimensional (3-D) Printing" of Titanium Alloys," *JOM*, vol. 66, no. 7, pp. 1299-1309, July 2014. Taylor hardening is given by Eq. 13, shown below. Presently, it is not well understood when Taylor hardening is present in the model, but is activated for the stress-relieved components in the build. The parameter α is the prefactor term (set to 1 here), M is the Taylor Factor (set to 3.2 here). G is the shear modulus of the material, b is the Burger's vector, and p is the dislocation density.

$$\sigma_{TH} = \alpha M G b \sqrt{\rho}$$   Eq. 13

In various embodiments, the Langmuir model can be applied to additive manufacturing in which Irving Langmuir's model for the vaporization of metallic tungsten is co-opted and adapted for use of modeling the vaporization of aluminum and uptake of oxygen during the AM build process. With respect to Irving Langmuir's model for the vaporization of metallic tungsten, see I. Langmuir. "The Vapor Pressure of Metallic Tungsten," *The Physical Review*, vol. 2, no. 5, pp. 329-342, 1913. Langmuir's primary application of his model was to determine the evaporation rate of tungsten filaments during his work for General Electric. In vacuum, his model can be expressed using Eq. 14:

$$\dot{m} = \sqrt{\frac{M}{2\pi RT}} \cdot p(T).$$   Eq. 14

In this context, M is the molar mass of the species of interest, R is the universal gas constant, T is temperature, and p(T) is the vapor pressure of the species of interest as a function of temperature. In S. L. Semiatin and P. A. Kobryn, "Microstructure and texture evolution during solidification processing of Ti-6Al-4V." *Journal of Materials Processing Technology*, vol. 135. pp. 330-339, 2003, it was shown that the Langmuir equation could be adapted for use in the modeling of vaporization of aluminum for casting of Ti-6Al-4V. In P. C. Collins, D. A. Brice, P. Samimi, I. Ghamarian and H. L. Fraser, "Microstructural Control of Additively Manufactured Metallic Materials," *Annual Review of Material Research*, vol. 46, pp. 63-91, 2016, the model was applied to additive manufacturing, showing how the equation could be used to model both the vaporization rate of aluminum and the absorption rate of oxygen in a "leaky" inert-gas AM system with poor atmospheric controls.

This model can be implemented in Python 3 and can operate on thermal histories supplied by ABAQUS, using a numerical summation method to account for and model the loss of rates of various species of interest.

In the implementation of the Langmuir equation, the loss modeling can be performed as a separate script, once thermal histories have been identified and exported as a comma-separated value (CSV) file. The Langmuir equation assumes there is a boundary that is boiling vapor. A small control volume can be assumed, in this example case, 0.1×0.1×0.1 in, and an emission surface area can be assigned. Comparison with several samples determined that an emission area of 0.08×0.08 m was acceptable and provided good agreement with samples that were used for the calibration step. The element size may seem large, but the surface to volume ratio appears to be the controlling factor rather than element size. Although the surface area to volume ratio was only calibrated against the aluminum, it was assumed that the same ratio should apply for the oxygen uptake in the build.

The CSV file is exported in the format shown below, where a script to automate the export process has been written to work within the Python 2.7 interpreter that ships with ABAQUS:

```
#Path, someAutoGeneratedPath-001
#Sample Location: 0.00m, 0.000m, 0.000m
Output DB: someDatabase-final.odb
TIME, NT11, Z_COORDINATE, NT11, Z_COORDINATE
0.000, 773.15, 0.000, 773.15, 0.000
```

The # at the beginning of the line signifies that the line is header information and is not to be imported. Each file is then imported into a pandas DataFrame, allowing all thermal histories to be indexed along the same timeline. The odd configuration of the CSV is due to the output being adapted from an earlier script that was designed to export multipoint paths over a time-series. The extraction script is incapable of understanding the concept of a point, and it is simply defined as a path with the same start and end point, hence the duplication of the data. If one was concerned about execution efficiency, one would make use of the C bindings that ship with ABAQUS, instead of relying on the Python bindings, which are significantly slower, but also easier to implement than the equivalent C routine.

Once all thermal histories have been assembled into the DataFrame, the time step is calculated using a backwards difference, with a simple piece of code to handle the first-entry edge case, where the script assumes the time step is the reported time. The vapor pressure is then calculated according to the reported temperature if required, and the loss-rate for the reported temperature is calculated. This is then scaled according to the surface area of emission and the time step. In this context, $\dot{m}$ is the output of Equation 16 for the species of interest. If modeling the vaporization of material, the sum should be subtracted from the initial mass, if modeling absorption, the sum should be added. To find the initial masses of the control volume, the density ($\rho$) is multiplied by the control volume (V) and multiplied by the mass fraction (X) of the species in the alloy.

$$m_{initial} = \rho V X \qquad \text{Eq. 15}$$

$$m_{final} = m_{initial} \pm \Sigma_{i=t_0}^{t_f} \dot{m}(t_i - t_{i-1}) \qquad \text{Eq. 16}$$

Implementation can be performed within the integrated computational materials engineering (ICME) model. Aluminum can be modeled as a loss, using the vapor pressure equation provided in C. B. Alcock, V. P. Itkin and M. P. Horrigan. "Vapour Pressure of the Metallic Elements," *Canadian Metallurgical Quarterly*, vol. 23, no. 3, pp. 309-313, 1984 and is given by Eq 17:

$$p_{Al}(T) = 10.917 - 16211/T, \qquad \text{Eq. 17}$$

where T is the temperature in Kelvin. and $p_{Al}$ is the partial pressure of aluminum in Bayres. A Bayre is equal to one tenth of a Pascal. Langmuir's formula was originally developed for the centimeter-gram-second system and has been left unadapted to mks.

Oxygen is modeled similarly, except instead of using the vapor pressure to determine the mass flow rate, the ambient chamber pressure can be used. It was then assumed that this was a standard atmospheric composition of 20% $O_2$. This provided the partial pressure for the oxygen uptake into the material.

There is however a sensitivity due to the modeling technique used. Each point has been assumed to have a finite element and has been modeled independently. The loss-accounting occurs within this element and not within any particular ABAQUS element. Therefore, the ratio of the emitter surface area to the volume of the model element can be calibrated presently against existing data. This procedure can be included as an ABAQUS user element subroutine, which would allow for the assignment of a boundary condition to better reflect the actual influence of geometry on the final chemistry of the build. This would be much more work than is implied, due to the procedure to create a unified "thermal-Langmuir" type element, that both performed the heat transfer functions, and the solute loss and absorption accounting. Otherwise, one would resort to a co-simulation or other technique to capture the data more accurately. Table 6 shows values used in the Langmuir model for specific species.

TABLE 6

| Parameter | Value | Source/Justification |
|---|---|---|
| $M_{Al}$ | 26.981 g/mol | NIST-SP 966 [27] |
| $M_{O2}$ | 31.998 g/mol | NIST-SP 966 [27] |
| R | 8.3145 J/molK | NIST-SP 966 [27] |

It should be evident that the Langmuir model is not a complicated one, but provides sufficiently accurate results. This simplicity is the model's greatest strength in design, as it does not require much computational horsepower, nor does it require a synthetic thermal profile. Implementation can include using this in-line with a thermal camera/pyrometer or through appropriate spectroscopic methods to determine what the aluminum/oxygen content should be within the build and then verify, potentially allowing an operator to stop the build if it was to fall irrecoverably out of a chemical or mechanical specification. The in-line can be implemented to control feed rates in the AM processing.

Another scenario for implementation of this procedure, using appropriate instrumentalities, can be applied during the deposition of the first layer, where the volume of the substrate compared to the volume of the layer is much greater and acts as a thermal reservoir. Currently, high aluminum content wire is used in builds to meet ASTM B348 or an equivalent. If the melt-pool temperatures of the first few layers are too cold, it is possible those layers can be out of chemical specification. This occurrence can be identified in real time and extra pass commands can be issued, where the material is brought just above the melt point to vaporize off extra aluminum and fall back into specification.

Although the model is capable of predicting the yield strength of AM Ti-6Al-4V in a satisfactory manner, the problem of texture remains. Ti-6Al-4V is predominantly the hep α-phase. Being hexagonal, with a c/a ratio of approximately 1.33 leads to significant anisotropy depending on orientation relative to load.

The role of texture in Ti-6Al-4V, especially in the context of additive manufacturing has been examined in previous work in P. C. Collins, D. A. Brice, P. Samimi, I. Ghamarian and H. L. Fraser, "Microstructural Control of Additively Manufactured Metallic Materials," *Annual Review of Material Research*, vol. 46, pp. 63-91, 2016. It is believed that, previously, the only method known in the US for the investigation of texture was Electron Backscattered Diffraction (EBSD) at this length scale or above.

EBSD is known for being unforgiving when it comes to sample preparation. The interaction volume is approximately on the order of 100 nm, and so any surface deviation or imperfection greater than that will cause a loss of signal. In addition, the operator is limited to the acceptable geometry allowed within the scanning electron microscope, keeping in mind that the published microscope space envelope will be severely reduced due to the stage being tilted to 70 degrees for a good front-scattering EBSD detector take-off angle.

Figure 16:
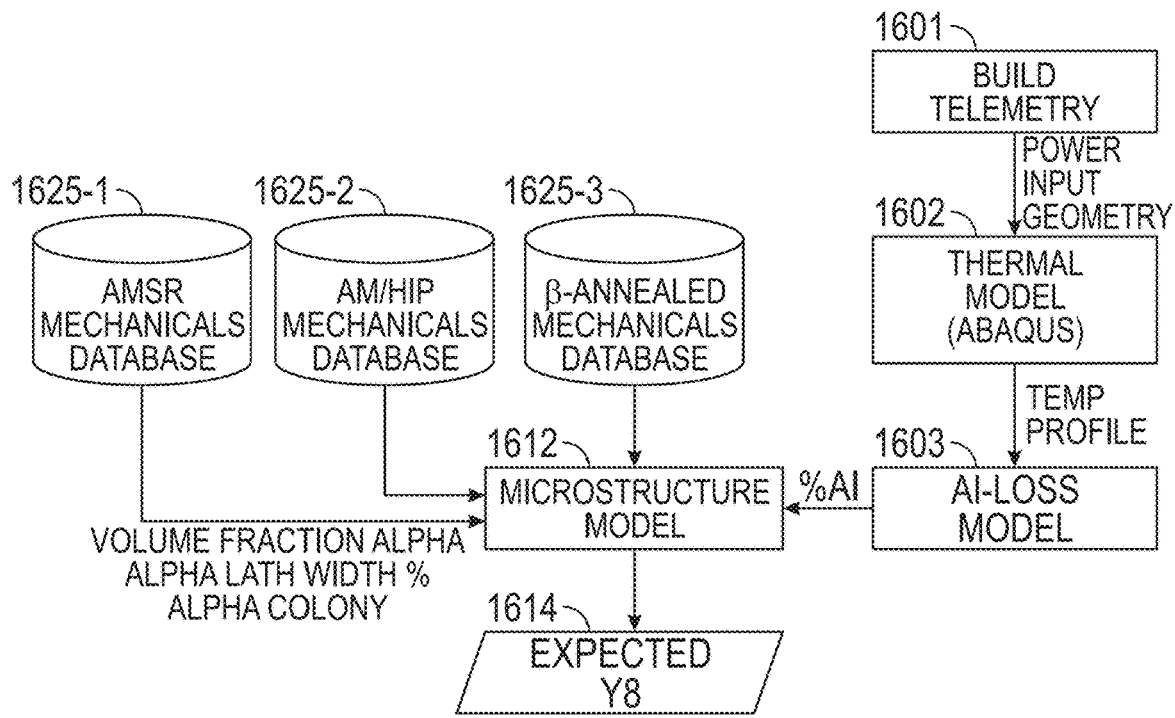
FIG. 16 is a flowchart for how application of a chemical and process model presently fuses the data from various sources.

A number of preliminary results of the application of chemical and process models to probabilistically predict $\sigma_{ys}$ in Ti-6Al-4V are provided. Shown in FIG. 16 is a flowchart for how application of a chemical and process model presently fuses the data from various sources. The flowchart relates to processing aluminum. The work flow begins with a build telemetry at 1601, which inputs a geometry to a thermal model 1602. Thermal model 1602 can provide temperature profiles to a loss model 1603, which can operate with respect aluminum loss as an example. These thermal profiles can be then fed into several Python scripts to determine the aluminum loss. For aluminum, loss model 1603 can output a percentage value for aluminum to a microstructure model 1612. Microstructure model 1612 can also receive inputs from databases 1625-1, 1625-2, and 1625-3. For example, databases 1625-1, 1625-2, and 1625-3 can be additive manufacturing-stress relieved (AM-SR) mechanicals database, additive manufacturing-hot isostatic pressing (AM-HIP) mechanicals database, and β-anneal mechanicals database. Other sources and procedures for data generation can be used. The inputs can include volume fraction α, α lath width, and % α colony. Output from microstructure model 1612 can provide an expected yield at 1614. The ABAQUS model is used to generate the thermal profiles for the virtual tensiles. Oxygen is not included in this model as the agreement between predicted and actual chemistries is currently poor. A hypothesis for this is presented in a later discussion, and oxygen values are presently modeled as a random selection from a normal distribution based on which heat treatment the tensile has been assigned.

The experimental datasets for the thinwall and thickwall geometries have been pulled from a database built for prior research in B. J. Hayes, B. W. Martin, B. Welk, S. J. Kuhr, T. K. Ales, D. A. Brice, I. Ghamarian, A. H. Baker, C. V. Haden, D. G. Harlow. H. L. Fraser and P. C. Collins, "Predicting tensile properties of Ti-6Al-4V produced via directed energy deposition," *Acta Materialia*, vol. 133, pp. 120-133, 31 Jul. 2017. Forty samples were classified as a thinwall geometry, which for this experiment was defined as a rib consisting of a single bead, where unlike the simulation, these samples had different interlayer rest times. The thickwall section consisted of 103 samples across the three heat treatments mentioned earlier. For this purpose, a thickwall geometry was defined as a rib section consisting of at least three bead widths, where these thickwall sections also had varying interlayer rest times. All builds used the same starting stock and roughly the same build process conditions.

For an initial simulated dataset, the initial dataset was built using the equation developed in B. J. Hayes, B. W. Martin. B. Welk, S. J. Kuhr. T. K. Ales. D. A. Brice. I. Ghamarian, A. H. Baker, C. V. Haden, D. G. Harlow. H. L. Fraser and P. C. Collins, "Predicting tensile properties of Ti-6Al-4V produced via directed energy deposition," *Acta Materialia*, vol. 133. pp. 120-133, 31 Jul. 2017, although this is a continuation and refinement of work began in P. C. Collins, C. V. Haden. I. Ghamarian. B. J. Hayes, T. Ales, G. Penso. V. Dixit and G. Harlow, "Progress Toward an Integration of Process-Structure-Property-Performance Models for "Three-Dimensional (3-D) Printing" of Titanium Alloys," *JOM*, vol. 66, no. 7, pp. 1299-1309, July 2014. A schematic form of the equation, with the particular weights for Ti-6Al-4V is given below in Eqs. 20-25 to illustrate each component's contribution to the overall strength of the material system:

$$\sigma_{YS}=(\sigma_0+\sigma_{SSS}+\sigma_{HP(\alpha\text{-}lath)}+\sigma_{HP(\alpha\text{-}colony)}+\sigma_{TH}+\sigma_{axisDebit}) \quad \text{Eq. 20}$$

$$\sigma_0=F_V^\alpha \cdot 89+F_V^\beta \cdot 45 \quad \text{Eq. 21}$$

$$\sigma_{SSS}=F_V^\alpha \cdot (149 \cdot x_{Al}^{0.667}+759 \cdot x_O^{0.667})+F_V^\beta \cdot ((22 \cdot x_V^{0.7})^{0.5}+(235 \cdot x_{Fe}^{0.7})^{0.5})^2 \quad \text{Eq. 22}$$

$$\sigma_{HP(\alpha\text{-}lath)}=F_V^{col} \cdot 150 \cdot (t_{\alpha\text{-}lath})^{0.5} \cdot (t_{\beta\text{-}rib})^{0.5} \quad \text{Eq. 23}$$

$$\sigma_{HP(\alpha\text{-}colony)}=F_V^{col} \cdot 125 \cdot (t_{colony})^{-0.5} \quad \text{Eq. 24}$$

$$\sigma_{TH}=F_V^{BW} \alpha M G b \sqrt{\rho} \quad \text{Eq. 25}$$

$$\sigma_{axisDebit}=\text{axisDebit} \cdot (\sigma_0+\sigma_{SSS}+\sigma_{HP(\alpha\text{-}lath)}+\sigma_{HP(\alpha\text{-}colony)}+\sigma_{TH}) \quad \text{Eq. 26}$$

Several of the inputs were sampled as a normal distribution using typical values from each heat treatment database, those defaults are listed in Table 7. Table 7 includes inputs for the model taken from B. J. Hayes. B. W. Martin, B. Welk, S. J. Kuhr, T. K. Ales, D. A. Brice, I. Ghamarian, A. H. Baker, C. V. Haden, D. G. Harlow, H. L. Fraser and P. C. Collins, "Predicting tensile properties of Ti-6Al-4V produced via directed energy deposition." *Acta Materialia*, vol. 133, pp. 120-133, 31 Jul. 2017, unless noted. Deviation is given as the percentage of the value.

TABLE 7

| | AM-SR | AM-HIP | AM-Beta | $COV_{SR}$ | $COV_{HIP}$ | $COV_{Beta}$ |
|---|---|---|---|---|---|---|
| % wt V | 4.23% | 4.01% | 3.91% | 3.5% | 3.5% | 3.5% |
| % wt Fe | 0.171% | 0.172% | 0.171% | 3.5% | 3.5% | 3.5% |
| % wt O | 0.166% | 0.167% | 0.166% | 3.5% | 3.5% | 3.5% |
| $F_v$ α | 90.08% | 92.60% | 90.96% | 3.0% | 3.0% | 3.0% |
| α-lath thickness | 1.099 μm | 3.533 μm | 0.998 μm | 12.5% | 17.5% | 17.5% |
| CSF | 7.11 μm | 12.41 μm | 240 μm | N/A | N/A | N/A |
| $F_v$ Colony | 17.80% | 19.37% | 100% | 10.0% | 10.0% | 0.0% |
| AxisDebit [35] | x: −4% y: −3% z: −8% | x: −1% z: −2% z: −4% | x: −3.5% y: −2% z: −3.5% | N/A | N/A | N/A |

In order to generate probability curves, the Monte Carlo method can be used. By creating normal distributions of what the possible predicted outputs could be depending on test error and uncertainty, an amplification effect can be used to determine what the population distribution might look like compared to the sample distribution. These distributions were used to generate 10,000 permutations of each datapoint based on observed uncertainties when doing the initial characterization work. Vanadium, oxygen and iron were varied within the known uncertainty of the EDS spectra that were acquired and were set to the averages for each heat treatment as reported in B. J. Hayes. B. W. Martin, B. Welk, S. J. Kuhr, T. K. Ales, D. A. Brice, I. Ghamarian, A. H. Baker, C. V. Haden, D. G. Harlow, H. L. Fraser and P. C. Collins, "Predicting tensile properties of Ti-6Al-4V produced via directed energy deposition," *Acta Materialia*, vol. 133, pp. 120-133, 31 Jul. 2017. Similarly, the microstructural features present in each heat treatment such as the alpha lath thickness, volume fraction of the alpha phase, volume fraction of the alpha colonies, were varied according to the observed uncertainties and average values. With these, the probability distributions can be computed and assessed.

Figure 17A:
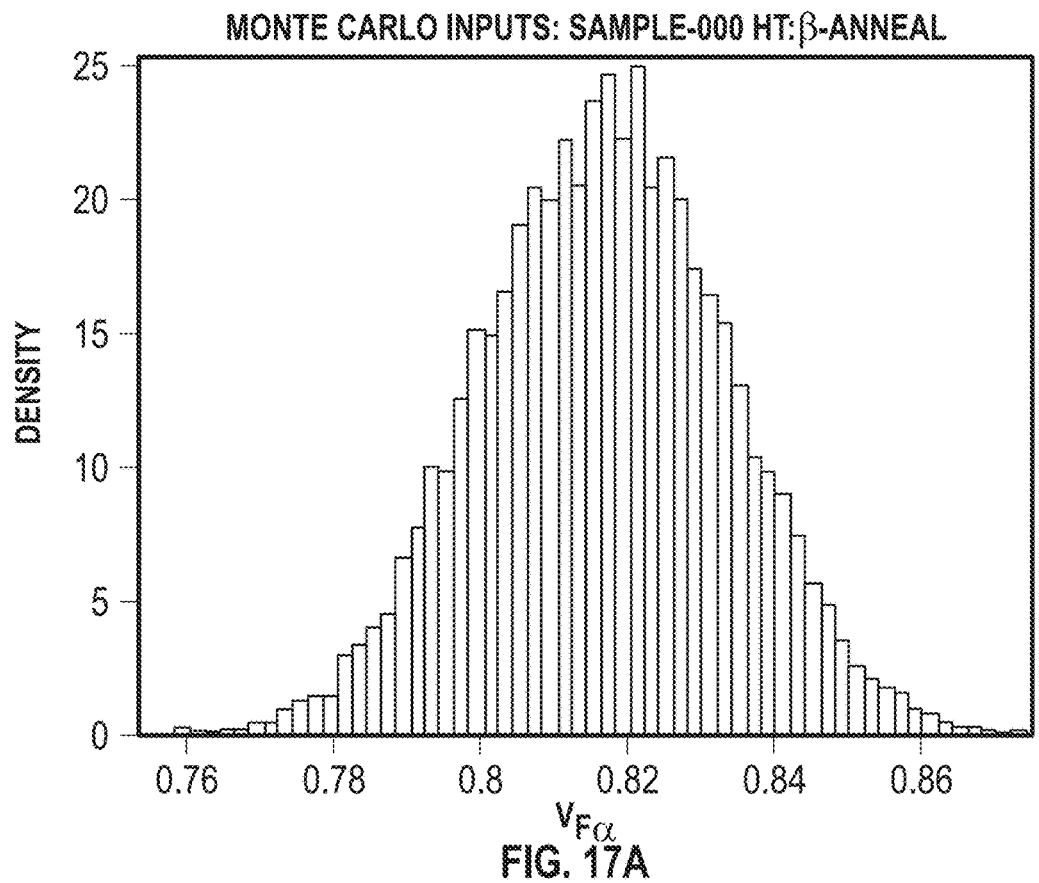
FIGS. 17A-E show probability density distributions for a sample assigned to β-anneal heat treatment.
Figure 17B:
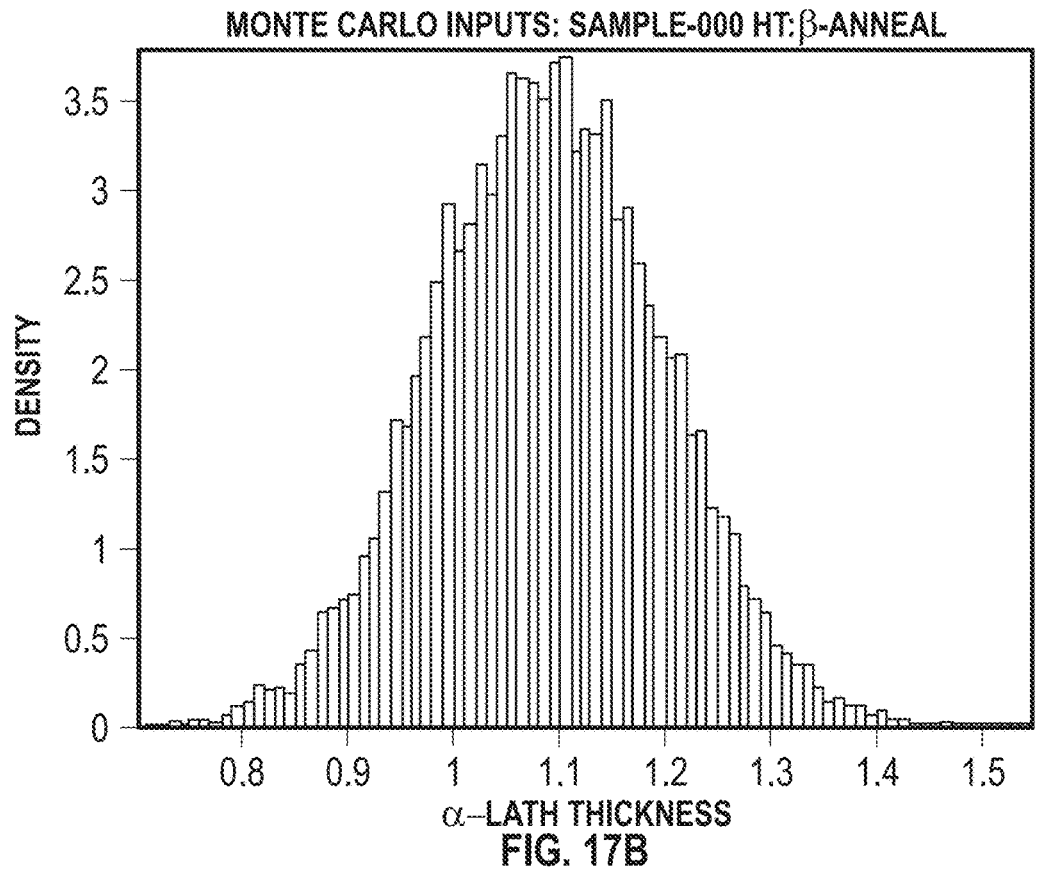
Figure 17C:
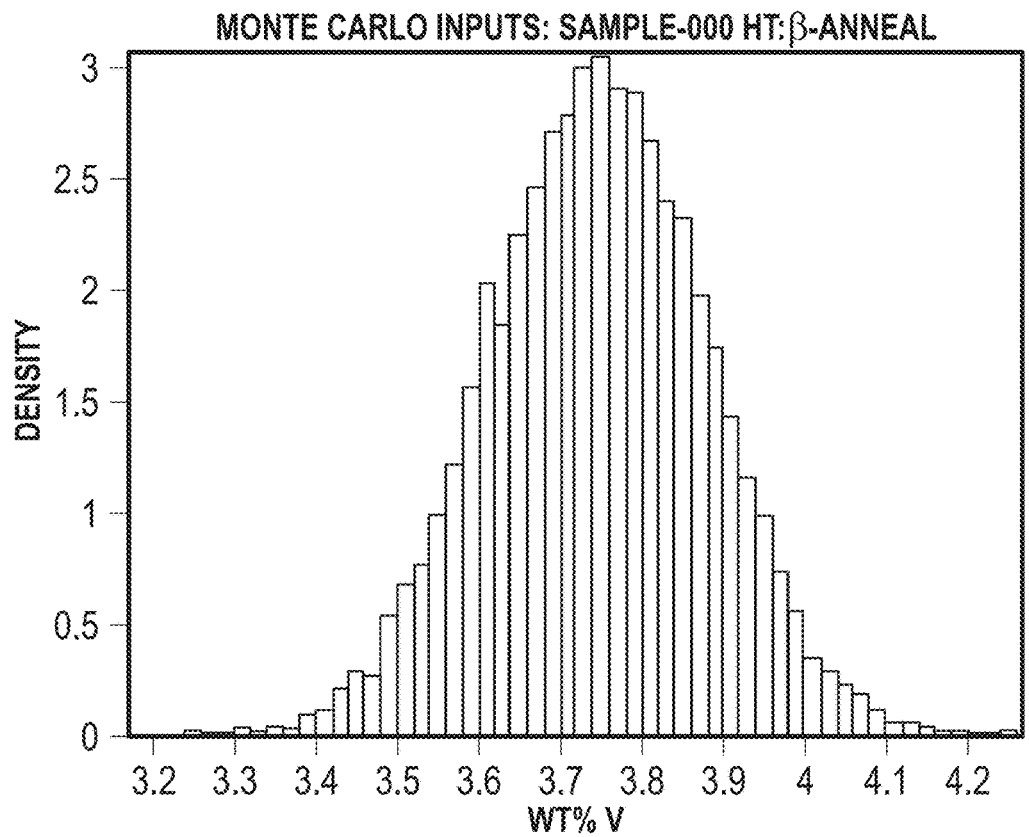
Figure 17D:
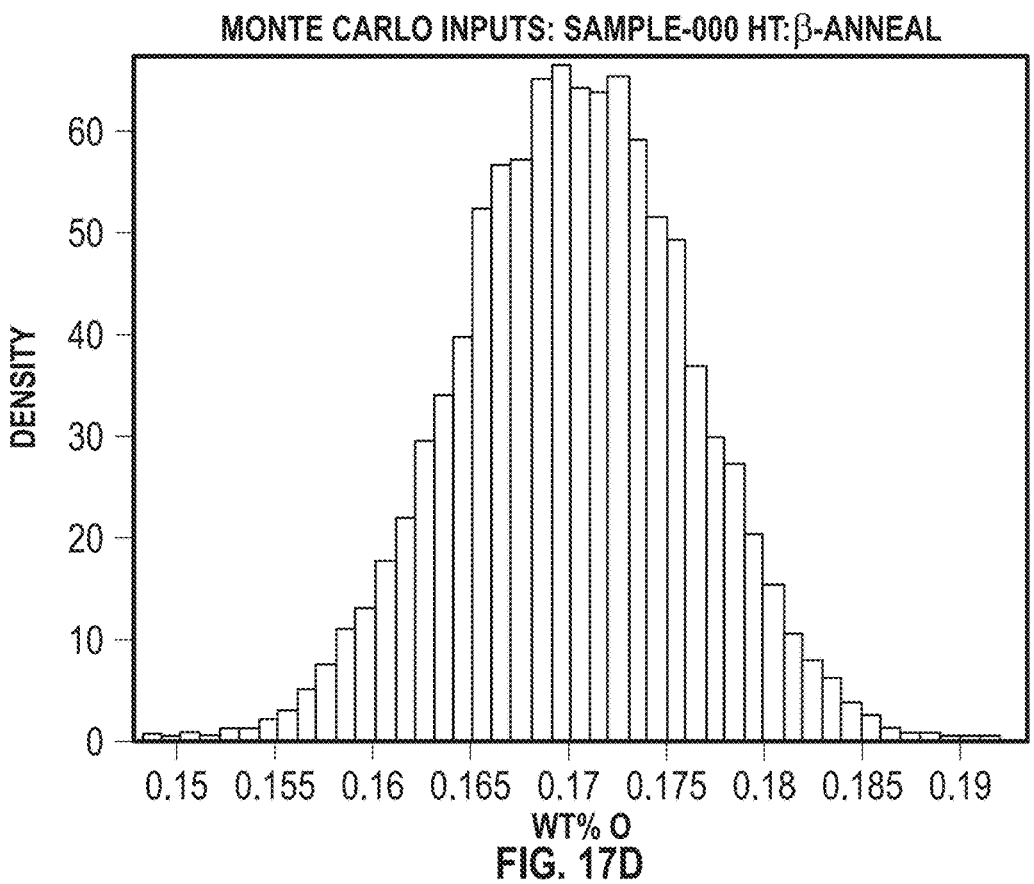
Figure 17E:
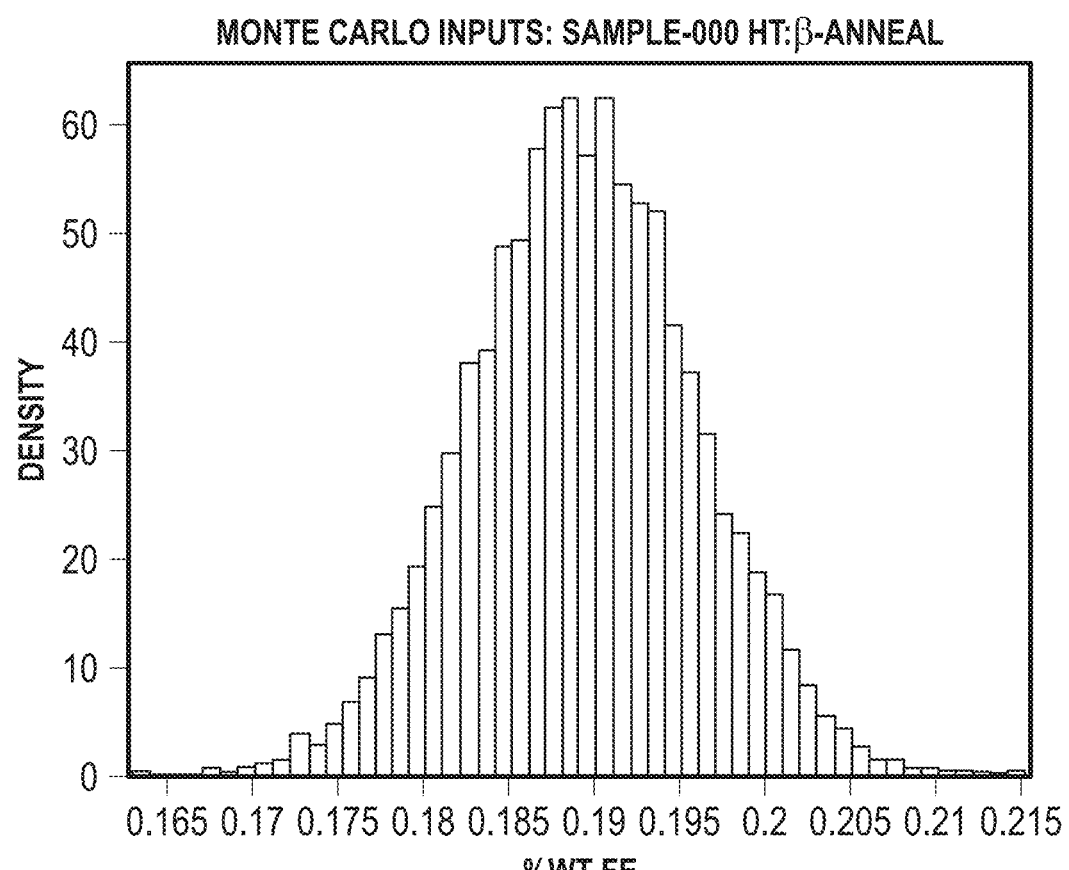

FIGS. 17A-E show probability density distributions (PDPs) for sample-000 assigned to the β-anneal heat treatment. FIG. 17A is a plot of probability density as a function of $V_{F\alpha}$. FIG. 17B is a plot of probability density as a function of α-lath thickness. FIG. 17C is a plot of probability density as a function of percent weight of vanadium. FIG. 17D is a plot of probability density as a function of percent weight of oxygen. FIG. 17E is a plot of probability density as a function of percent weight of iron.

Figure 18:
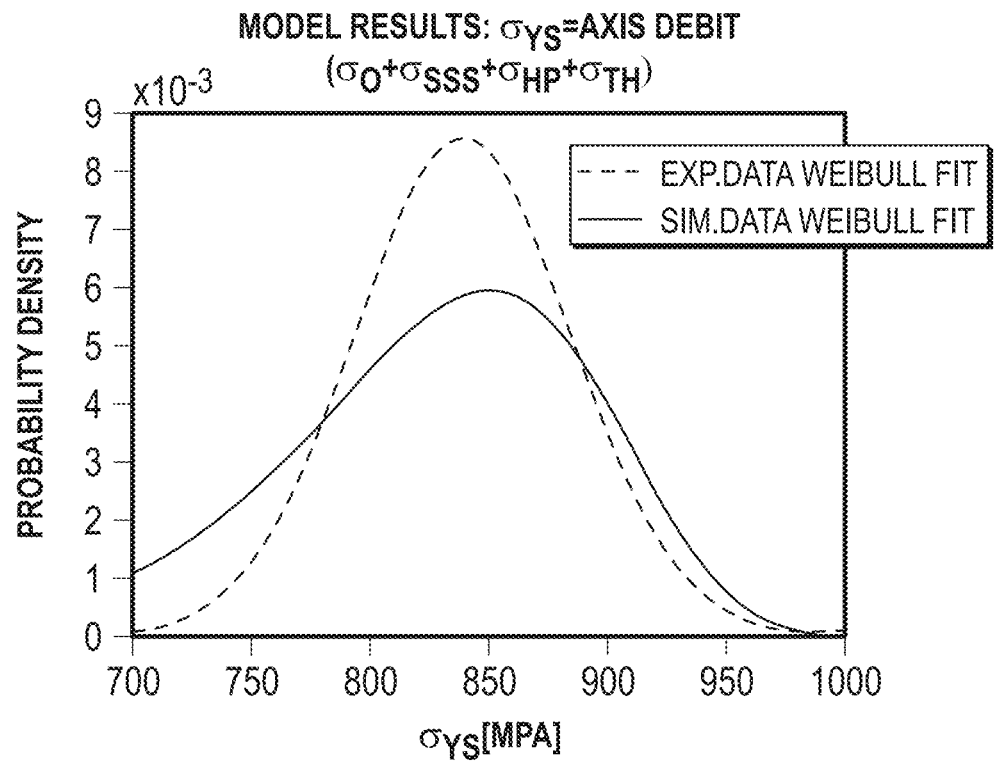
FIG. 18 shows a probability density fit for the thinwall after calibration.
Figure 19:
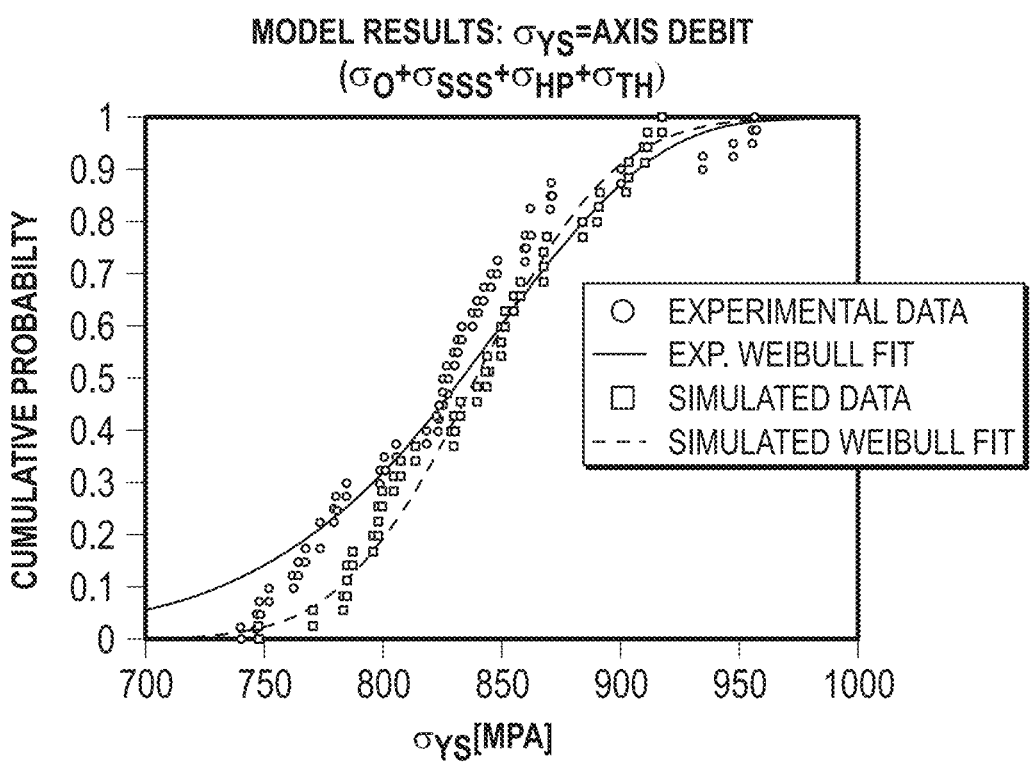
FIG. 19 shows a cumulative distribution plot for the thinwall dataset, post-calibration.
Figure 20:
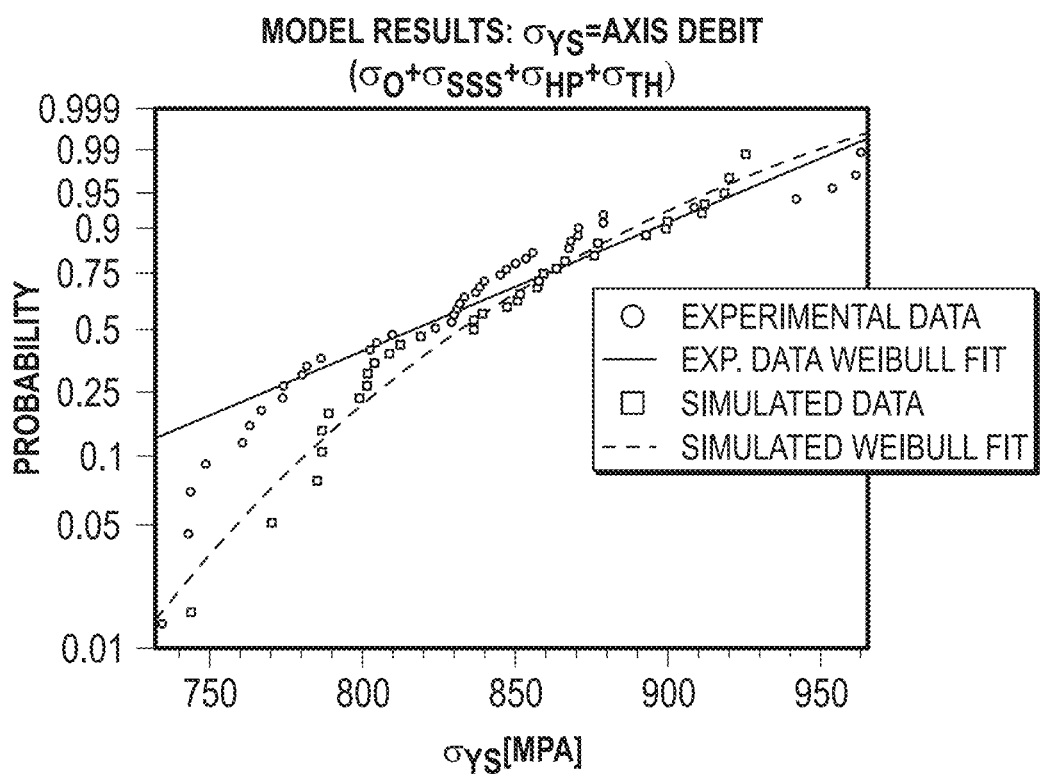
FIG. 20 shows a Weibull probability plot for thinwall model, post-calibration.

The thinwall section was used to calibrate the Langmuir model surface area to volume ratio for the finite element. The probability density function fits are shown in FIG. 18. FIG. 18 shows a probability density fit for the thinwall after calibration. After calibration, the model has an average yield strength of 818 MPa, with a standard deviation of 75 MPa, the experimental dataset reports an average yield strength of 854 MPa and standard deviation of 24 MPa. There is a 4.2% disagreement in mean values between the experimental and computational datasets. FIG. 19 shows a cumulative distribution plot for the thinwall dataset, post-calibration. FIG. 20 shows a Weibull probability plot for thinwall model, post-calibration. Table 8 shows thinwall experimental dataset statistics, separated by heat treatment. Table 8 shows the thinwall results by individual heat treatment, along with the percentage of the dataset the heat treatment makes up.

TABLE 8

| Heat Treatment | $\overline{\sigma_{YS}}$ | $\sigma_{\sigma YS}$ | Percentage of Dataset |
|---|---|---|---|
| AM-SR | 805.4 | 47.5 | 50% |
| AM-β-Anneal | 768.9 | 19.4 | 16.6% |
| AM-HIP | 760.7 | 20.1 | 33.3% |

After the thinwall results had been calibrated to satisfaction, verification was performed against the portions of the database that would classify as "thickwall" section. The larger number of samples in this portion of the database allowed for separation of the heat treatments and the results are presented as such. First, the AM-SR model is presented, followed by the AM-β-Anneal and AM-HIP models. The other difference between these results and the results of the previous section is the Monte Carlo procedures have been added to generate a larger sampling distribution. While matching the average yield strength for a thickwall component well, the distributions are not an ideal match, as discussed latter.

Table 9 is a comparison of average $\sigma_{YS}$ between model and experimental results.

TABLE 9

| Treatment | Sim. YS Average | Sim. YS Std. Deviation | Exp. YS Average | Exp. YS Std. Deviation | Error in Avg YS |
|---|---|---|---|---|---|
| AM-SR | 886 | 31 | 856 | 57 | 3.5% |
| AM-HIP | 802 | 28 | 775 | 24 | 3.4% |
| AM-β-Anneal | 780 | 31 | 801 | 27 | 2.6% |

Compared to the experimental results, the model tends to over predict the stress relieved and HIP condition heat treatments, while under predicting the β-Anneal treatment in the current parameter configuration.

Figure 21A:
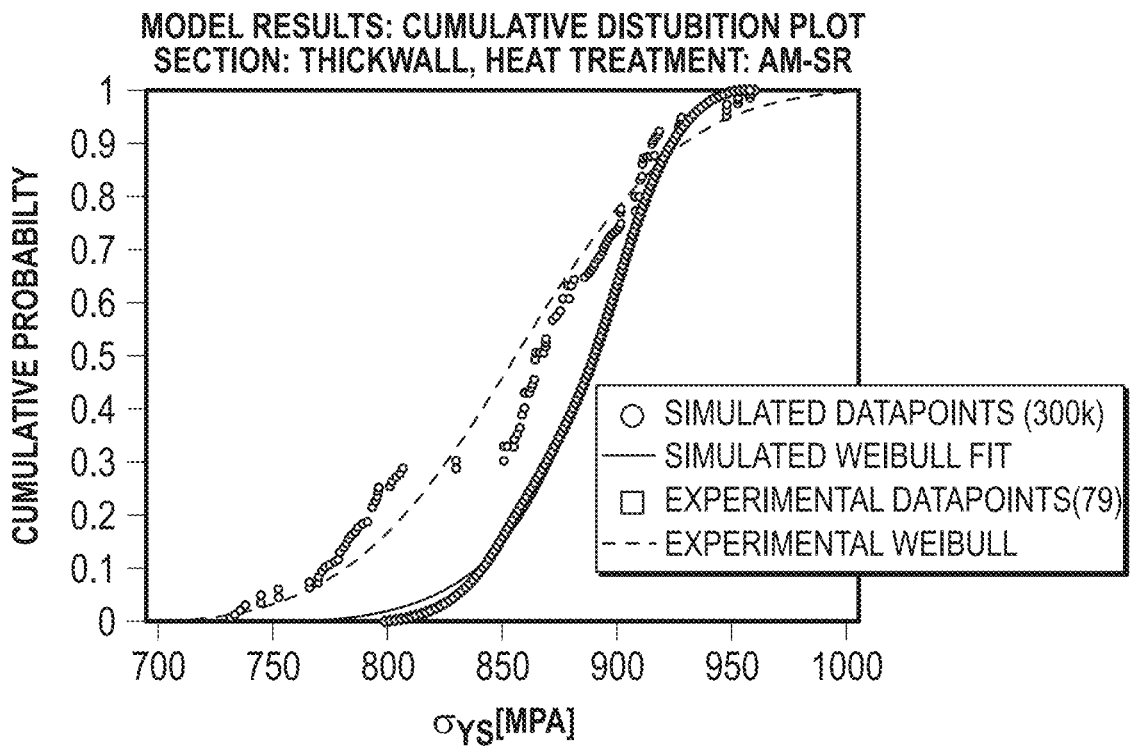
FIGS. 21A-C show results for an additive manufacturing-stress relieved heat treat condition.
Figure 21B:
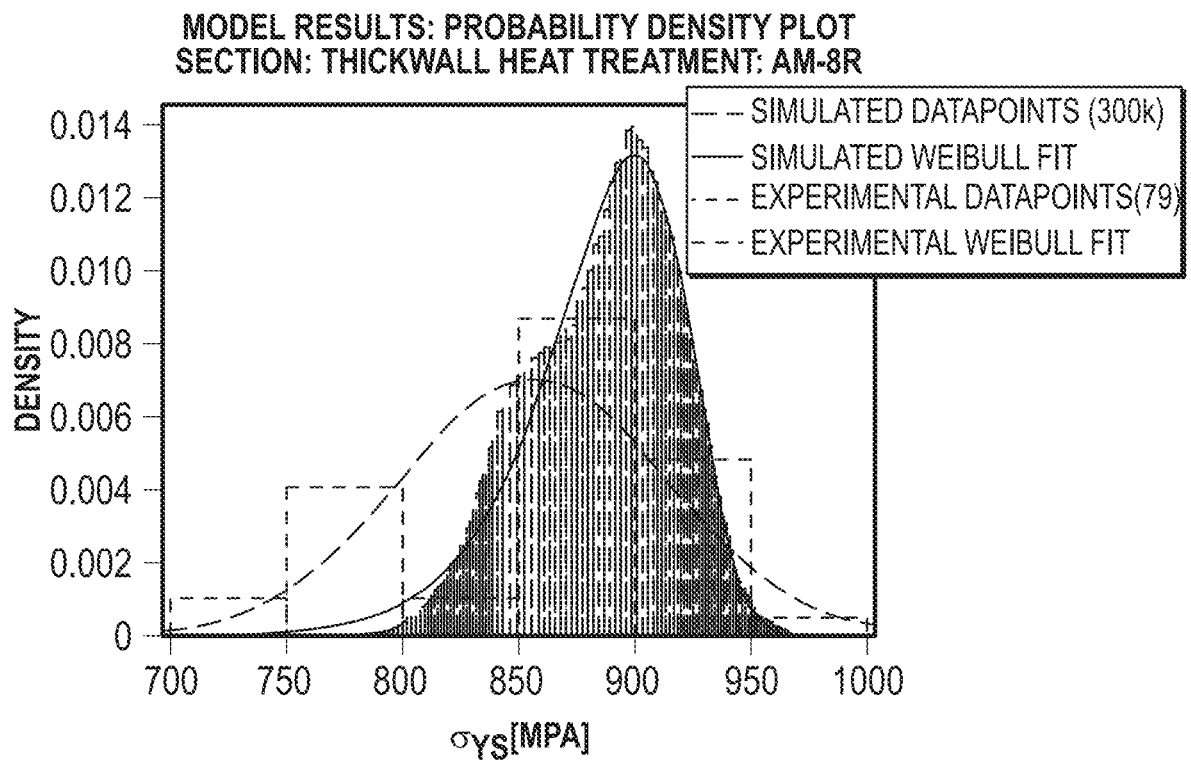
Figure 21C:
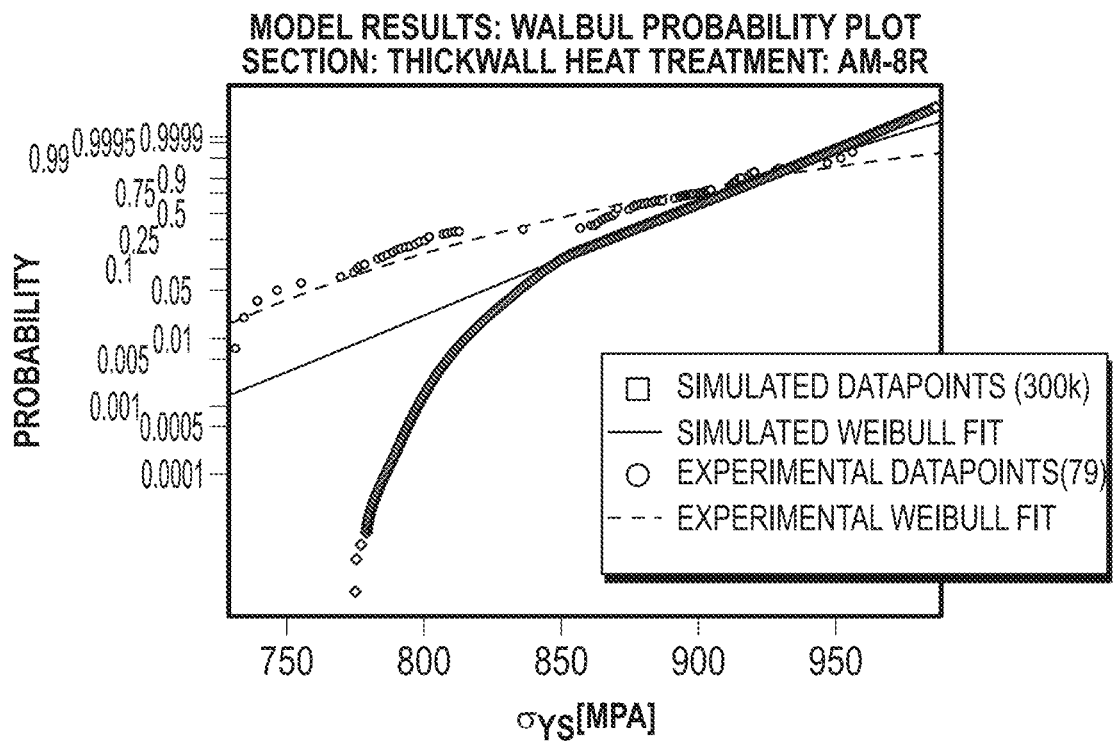

FIGS. 21A-C show results for the AM-SR heat treat condition. FIG. 21A is a cumulative distribution plot. FIG. 21B is a probability density plot. FIG. 21C is a Weibull probability plot.

Figure 22A:
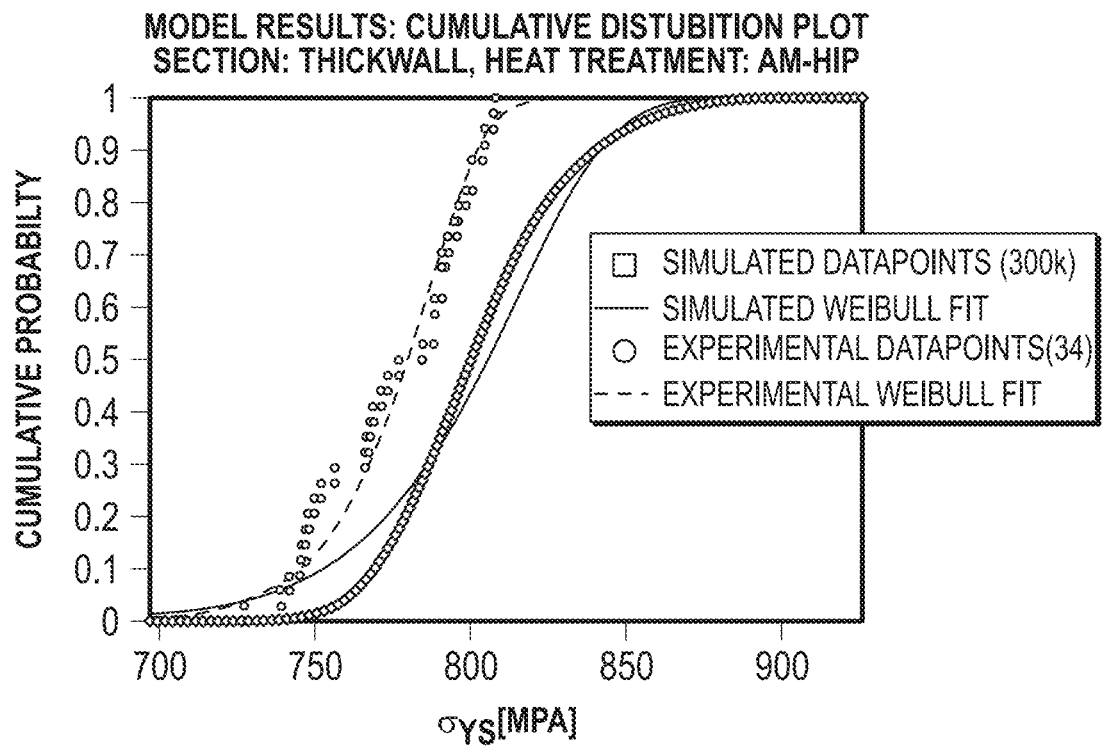
FIGS. 22A-C show results for a hot isostatic press heat treat condition.
Figure 22B:
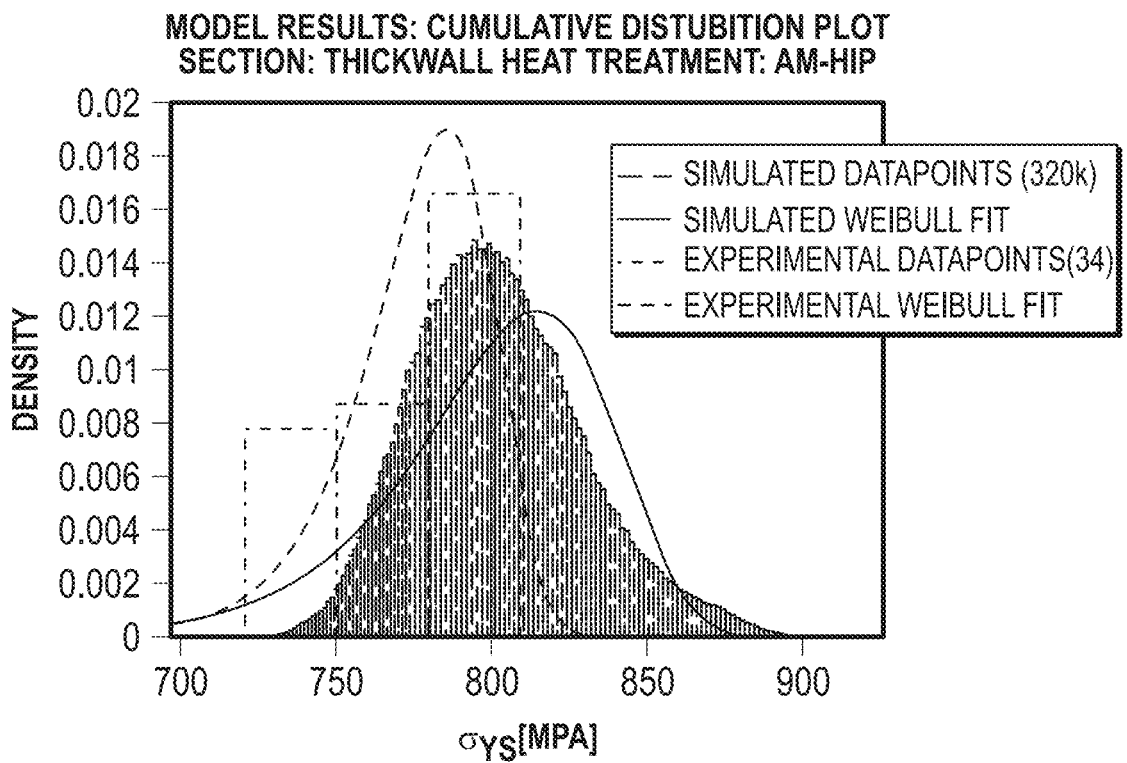
Figure 22C:
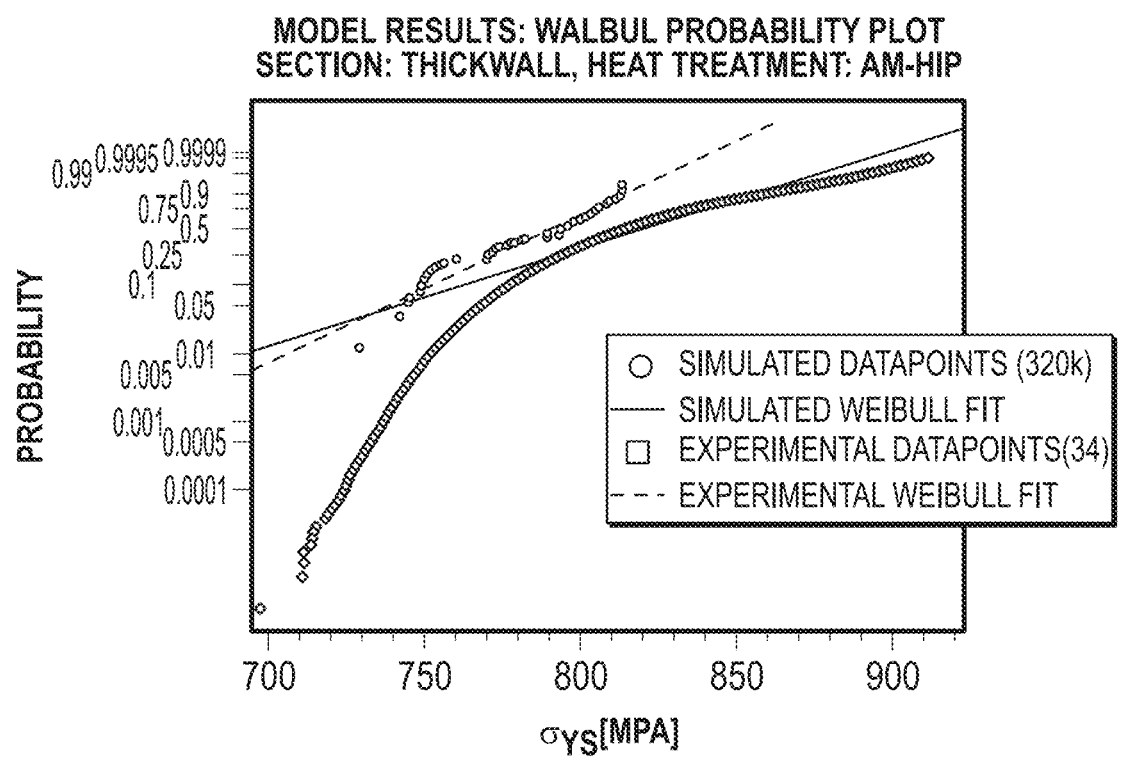

FIGS. 22A-C show results for the HIP heat treat condition. FIG. 22A is a cumulative distribution plot. FIG. 22B is a probability density plot. FIG. 22C is a Weibull probability plot.

Figure 23A:
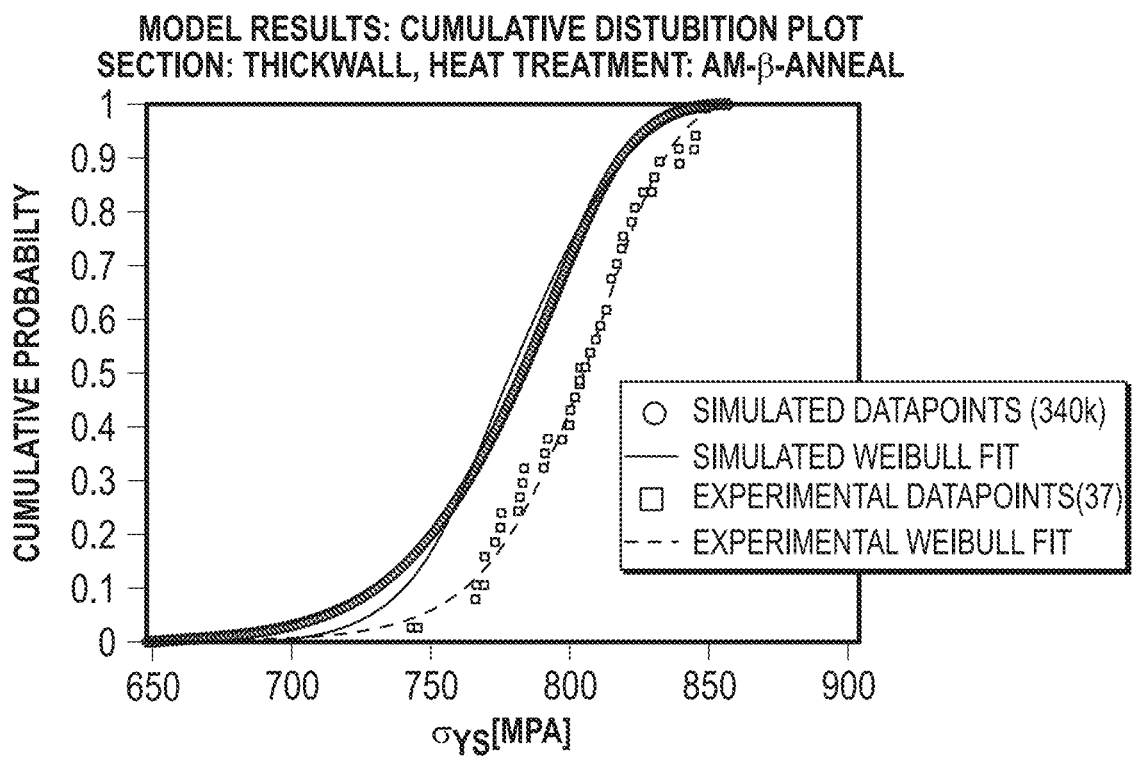
FIGS. 23A-C show results for an additive manufacturing-beta-anneal heat treat condition.
Figure 23B:
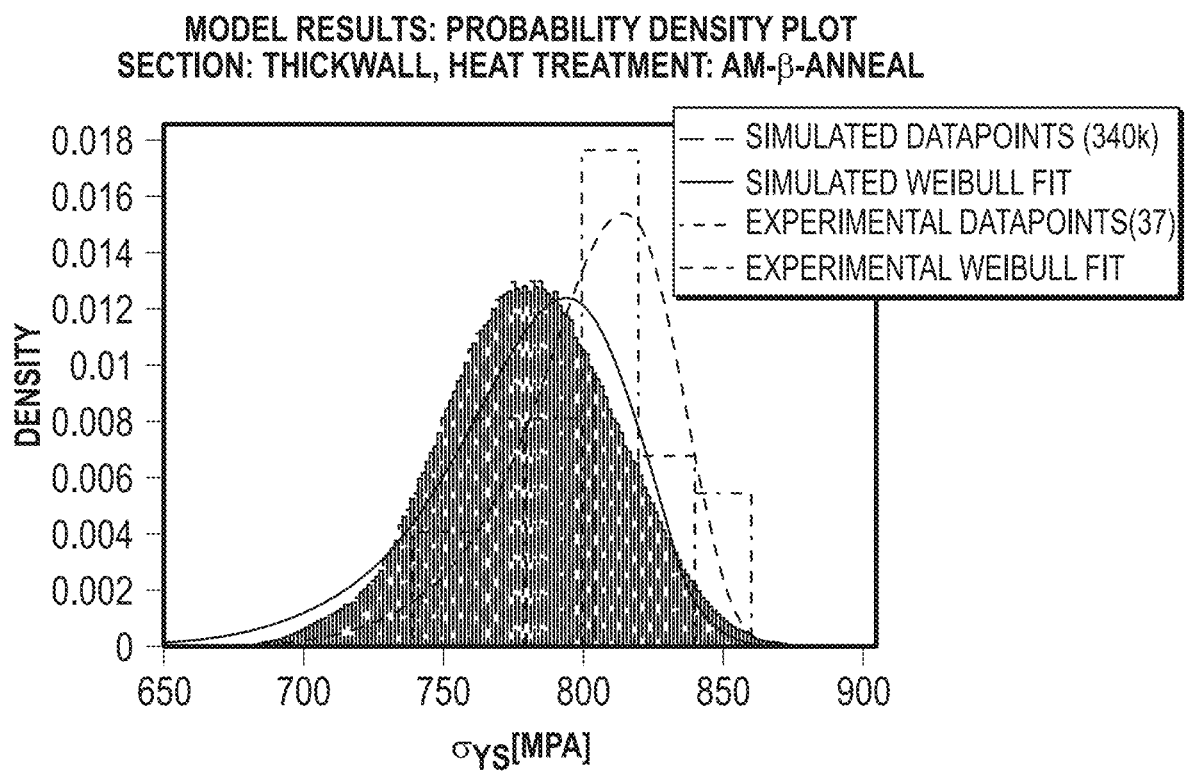
Figure 23C:
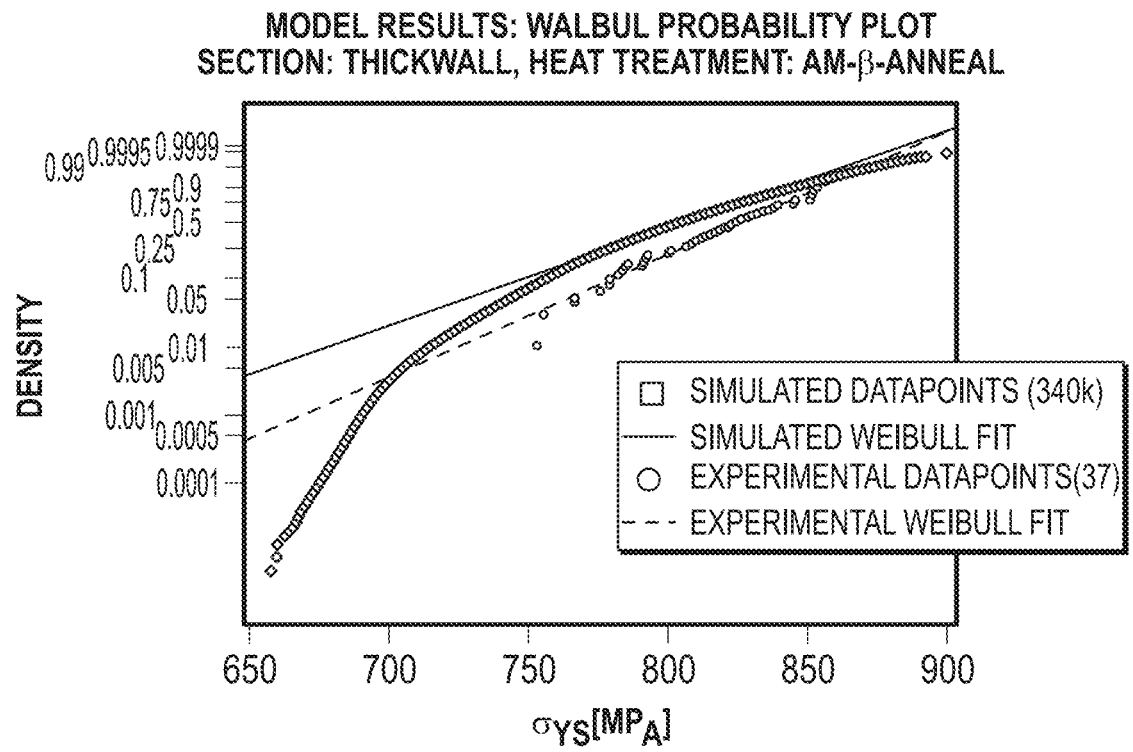

FIGS. 23A-C show results for the AM-beta-anneal heat treat condition. FIG. 23A is a cumulative distribution plot. FIG. 23B is a probability density plot. FIG. 23C is a Weibull probability plot.

The teachings herein have shown that it is possible to perform probabilistic modeling of mechanical properties in Ti-6Al-4V, which presents a framework or philosophy that can be used outside of any particular FEA package or with any particular language. The model does not attempt to show itself as an optimized solution, and in fact is a sub-optimized one at best, but presents an approach that could be applied to any material system or manufacturing process, provided the groundwork of developing the material databases and/or other procedures to generate data of respective elements of the process is performed, or if models presently exist that sufficiently describe the process-structure-property-performance relationships. In various embodiments, a database of thermodynamics data can be implemented as any summary of thermodynamics data.

Figure 24:
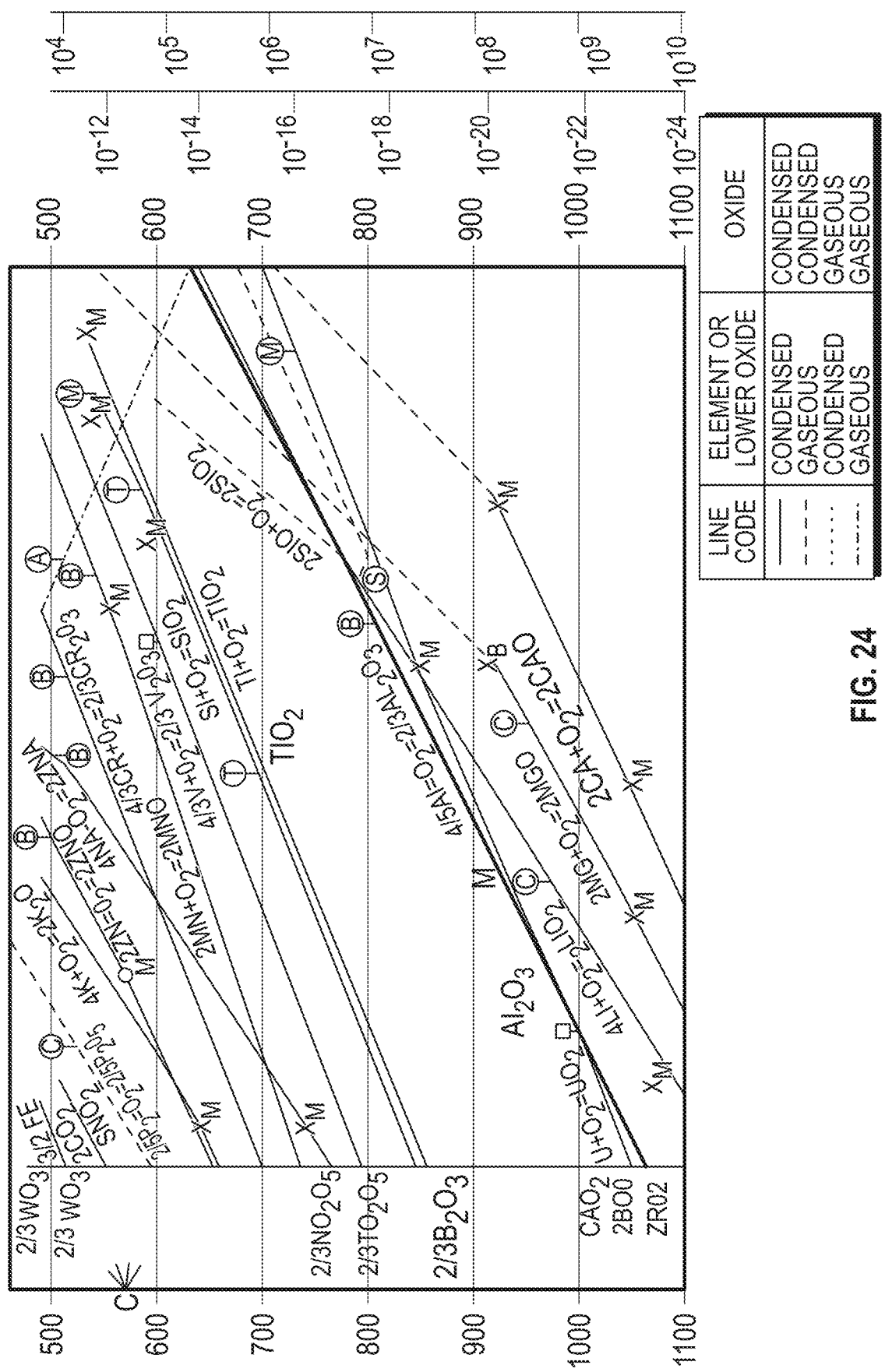
FIG. 24 is a portion of an Ellingham Diagram showing titanium oxide and aluminum oxide.

It is noted that several important variables, not discussed herein, can be modeled in sufficient detail, for example, notably oxygen content and the volume fraction of the α-phase. It was decided that for the testing in this work, oxygen modeling would not be used due to seeing far higher predicted oxygen content in the material than what was experimentally observed. It was hypothesized that if there is an aluminum vapor plume it may be acting like a shield gas. On a portion of an Ellingham diagram showing $TiO_2$ and $Al_2O_3$ (See T. Gutowski. "Lecture Notes: MIT 2.813: Energy. Materials and Manufacturing." MIT, 2015) in FIG. 24, it is shown that the $Al_2O_3$ free energy is much lower than the $TiO_2$ free energy, which may explain the severe discrepancy between the modeled and observed information.

Figure 25A:
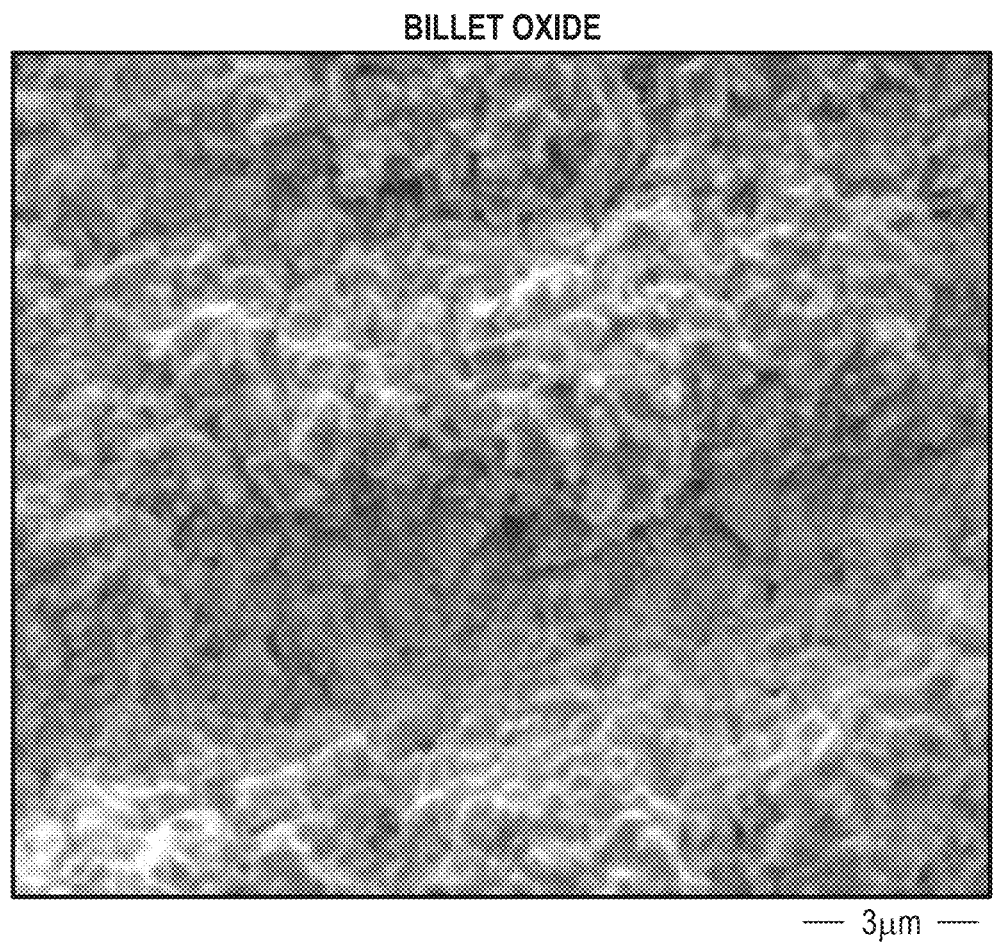
FIGS. 25A-B provide a comparison of a small portion of billet oxidized in atmosphere versus the oxide layer on a build by an electron beam additive manufacturing.
Figure 25B:

There is circumstantial evidence for this phenomenon both in morphology, and chemistry. The surface of a build was inspected under secondary mode along with a sample that was quickly oxidized in a box furnace at 800 C for 1 hour and allowed to air cool. The two surfaces are shown in FIGS. 25A-B. FIGS. 25A-B provide a comparison of a small portion of billet oxidized in atmosphere versus the oxide layer on an EBAM build. The sample in FIG. 25A has a typical morphology that would be expected of the native oxide during forging or similar thermomechanical process. However, the sample in FIG. 25B, which is from an EBAM build, has a very smooth, almost glass-like surface that does not have much deviation. Raman spectroscopy was used to investigate the properties of the oxide layer on the build and shows a mode corresponding to $Al_2O_3$ bonding, showing that there is a presence of corundum. Although further work is required for confirmation of the formation of corundum, it is a plausible explanation of the discrepancy between the simulated and observed oxygen levels. An in-situ Laser-Induced Breakdown Spectroscopy (LIBS) system or a similar technique may have the capability to be used to directly characterize the chemical nature of the vapor plume.

Figure 26:
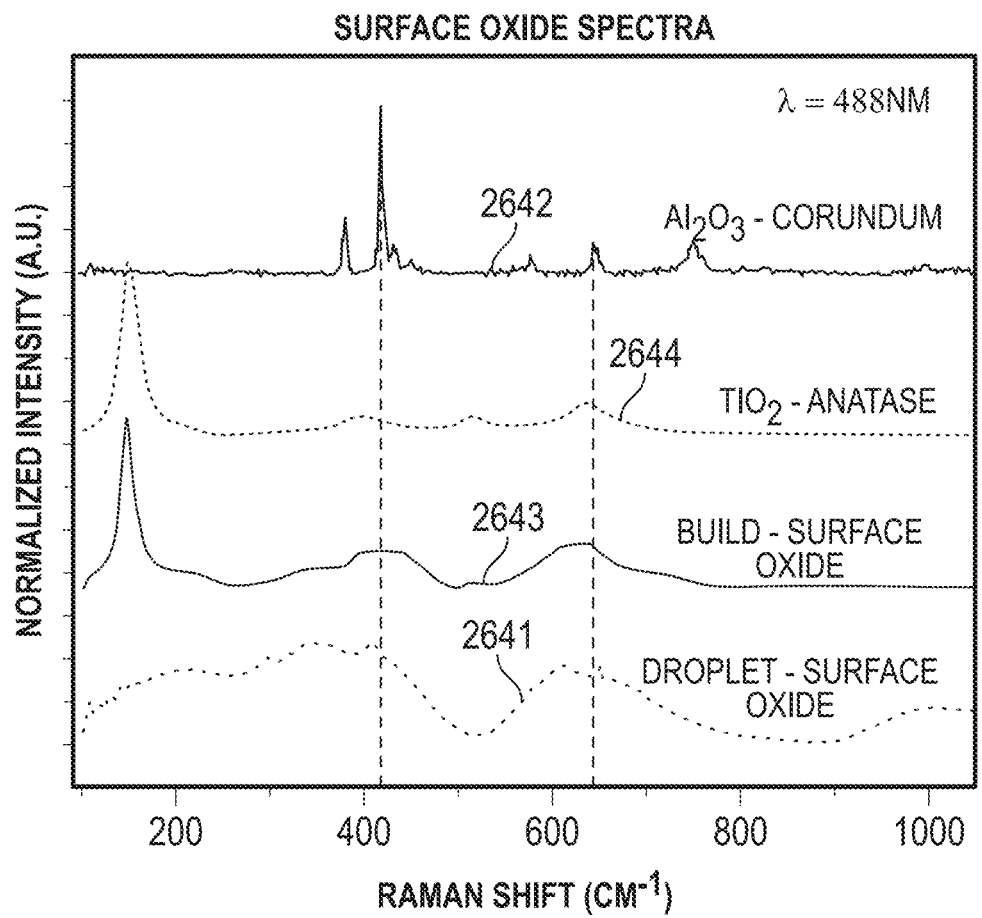
FIG. 26 illustrates Raman spectra captured of a small portion of build.

Raman spectroscopy was an ideal candidate for a quick investigation of the oxide surface character, as metals are invisible to the technique. FIG. 26 illustrates Raman spectra captured of a small portion of build. The sample is given in curve 2641, while two standards used for comparison are given in curve 2642 ($Al_2O_3$-corundum) and curve 2644 ($Ti_2$-anatase). Curve 2643 is the response of the surface oxide from the sample that was exposed to a 'typical' forging preheat cycle, and the curve 2641 is the surface oxide of a droplet that was deposited on the substrate near the build. The surface oxide contains modes centered around 148, 399.515, and 636 $cm^{-1}$, corresponding to $TiO_2$ low-temperature Anatase phase. The primary mode of $Al_2O_3$ lies at 420 $cm^1$, which corresponds to the discrepancy observed in the droplet, along with the falloff of response between 430-500 $cm^{-1}$, which would imply Anatase is not as present, suggesting higher cooling rates compared to the oxidized sample.

The microstructural characteristics are currently generated through the use of known typical distributions. In C. C. Murgau. R. Pederson and L. E. Lindgren. "A model for Ti-6Al-4V microstructure evolution for arbitrary temperature changes," *Modeling Simul. Mater. Sci. Eng.*, vol. 20, 2012, it has been shown that the Johnson-Mehl, Avrami, & Kolmogorov model can be adapted for the cyclic and varied temperature changes that are seen in the AM build process. This can help provide better and more accurate predictions for the α-fraction as a function of location within the model. Presently in the dataset, the Colony Scale Factor uncertainty is not characterized, leading to assumptions about what distribution and deviation parameters to use.

Many typical AM processes begin with acquisition of a product having preset chemistries and compositions, which may be typically obtained as a certified product. Then, the product is subjected to AM processes, corresponding to the desired final product, where the product, at least in part, becomes molten prior to solidification that includes additive material from the AM processes. However, in such typical fabrication processes, because the AM processes are typically very high energy processes, certain elements of the product, to which one starts a selected AM process, can be preferentially lost to the atmosphere. The loss depends upon the precise nature of the process, but sometimes the chemistries that are part of the final end product can be modified by a significant percent from the starting material, such as for example fifteen, twenty, or thirty percent from the starting material, which may not be acceptable. In certain alloys, that bound can be tighter. This can lead to trial and error procedures, which can reduce efficiency of the manufacturing process.

In various embodiments, control of the chemistry of a final product from AM processes can be accomplished by prediction and engineering of the starting chemistry of the material that is entered into the process. In such embodiments, systems and methods of operating such systems can include predictably accounting for the loss of certain species for certain AM platforms. For example, in aerospace applications, systems and methods can be implemented in producing alloys to account quite accurately for the loss of material from the alloy, for instance the loss of aluminum from a titanium alloy. The approaches of these systems and methods can also be used to account for the uptick of certain gases species into the product form being manufactured. For example, such systems and methods can be implemented to predict an amount of oxygen that enters the molten material during the AM process. The approaches of these systems and methods can be implemented to control the loss of element A from the molten material being processed to prevent the uptick of element B into the molten pool. For example, an amount of oxygen in a titanium alloy may be acceptable up to a certain concentration, but additional amounts of oxygen added to the titanium alloy may make the titanium alloy crack and fall apart, which is not acceptable. To avoid such occurrences, a sacrificial element can be included in the material used in the AM process such that the element is lost from the molten pool but combines with the oxygen, or other detrimental elements in the environment in which the workpiece of the AM process is being fabricated, to prevent the oxygen or other detrimental elements from entering into the molten pools of molten metal and solidifying with the metal.

An element can be inserted into the AM process, either as additional element or as an additional amount of the element, to selectively volatilize in the feedstock for the AM process and combine with one or more unwanted elements with the combined materials carried away from the molten material being processed to prevent inclusion of the unwanted element in the end product of the AM process. For example, in a particular case, the loss of aluminum under some conditions prevents the absorption of oxygen and other gases species. Consider a situation in which a desired alloy, as an end product of an AM process, is to have an end objective aluminum concentration of, for example, 6%, the process could start with a material that had 7.5% aluminum, knowing that a fraction of the aluminum will be lost. The excess aluminum would then act as a scavenger immediately above the molten pool, and take the rest of the elements above the molten pool away from the molten pool, while the aluminum itself was being volatilized.

Depending on the workpiece and the AM process being used, other elemental species can be input to provide a scavenging function. For example, in some applications, magnesium may be used as a scavenger. All the magnesium, or other scavenger element, may be volatilized with none of the magnesium or other scavenger element being included into the build. However, by it being volatilized, the magnesium or other scavenger element would sweep away unwanted elements and clean up the atmosphere immediately above the molten pool. The scavenger element may be introduced in a solid, a gas, a liquid, or combinations thereof. The scavenger element may be implemented as one or more scavenger elements. In various embodiments, an amount of the scavenger element or amounts of scavenger elements can be included in the build at levels that are less than or equal to or less than a threshold amount for inclusion in the build.

To incorporate control of material lost or added in a given AM process, the target of interest can be identified with a design process implemented working back from the target. The effect of working condition, for example especially the temperature on the relevant chemical potentials, can be tracked to be able to predict a composition with which to begin the AM process so that the target, at least within a selected range of material composition, can be fabricated as the end product. Based on chemistry that is occurring during the melting and coding process from the tracking and modeling, as taught herein, the proportional composition of material that is used to start the AM process can be determined that would result in the end product having a composition of the target of interest or being within an acceptable range of the concentration of the elements of the target and/or inclusion of trace by product elements at an acceptable level. This approach avoids the trial and error sort of approach used in conventional AM processes.

In various embodiments, features of methods to conduct an AM process can be implemented using one or more processors. A determination can be made as to what element or elements will react with gaseous species with removal away from molten material formed in the AM process to fabricate a target end product. The determination can include accessing one or more databases having thermodynamic databases and other data, providing knowledge regarding possible elements and compounds that can be used in the AM process to produce the target end product; calculating data for the element, applying different conditions to generate data regarding the element, or performing combinations thereof. Using one or more processors, the databases can be accessed remotely over a communications network. The target end product can be defined by a composition within a range of a target composition. For a simple example, available thermodynamic data can contain data that aluminum volatilizes and takes away oxygen. However, a task of AM methods, as taught herein, can include a determination of the conditions under which the AM process can be implemented to preferentially lose aluminum to remove oxygen. The preferentially lost can be determined relative to a desired amount of aluminum to be retained. The Langmuir equation can be applied to parameters of the elements determined for possible use. The parameters can include thermodynamic data. It noted that the Langmuir equation is a diffusion equation that can be used to determine evaporation rate. It can be used to analyze how much material is lost per unit time.

The Langmuir equation and thermodynamic data of one or more elements in the AM processing can be tied into a finite element model of thermal processes of an additive manufacturing build. This build can be directed to the target end product. In tying the Langmuir equation and thermodynamic data into the finite element model, one or more data inputs can be provided to a system storing and/or executing a processing model or simulation model that includes the finite element model of thermal processes with the Langmuir equation integrated to conduct an additive manufacturing build. The input can include one or more of identifications for a target end product or target composition, thermodynamic parameters relevant to the elements associated with the target end product or the target composition, allowable variances for a particular additive manufacturing build and/or target end product, or other data to execute the finite element model. Features of methods that tie the Langmuir equation to a finite element can include determining or knowing how hot the molten pool of the molten material in the AM processing gets and how long the molten pool is in its molten state, such that there is a temperature component as well as a time component in the analysis. Methods to improve AM processes, as taught herein, can include three significant components: thermodynamic databases and/or knowledge of elements for use in the AM process; the Langmuir equation, and the Langmuir equation tied into a finite element model of the thermal history of each location in an additive manufacturing build.

Results from execution of the finite element model can be generated in which the results specify composition of starting materials for the additive manufacturing build to fabricate the target end product. The starting materials can be specified as the identification of elements of the starting materials and concentration ranges of the elements of the starting materials within a specified range of composition that can be used to fabricate the target end product. The starting materials can include the starting chemistry that one would use in an incoming wire in the AM process. The specified range of composition can include ranges of concentration of elements in the target end product. The specified range of composition can also include identification of trace elements, where trace elements are unwanted elements with respect to a pure target composition, and thresholds for acceptable levels of the trace elements.

The Langmuir model can deal with each element type separately. A method can use the Langmuir model to track competing losses or gains of any element in the simulation. Not all of the elements in the identified process are going to be reactive. Some elements may be reactive with certain species, and not with other species. These reactions can occur as metered activities in a stepwise manner. With chemical kinetics modeled, the processing system can use redox potentials. The element that has the lowest redox potential dominates in an oxidizing environment. In a reducing environment to remove an element or compound, for example hydrogen, the material with the highest redox potential dominates. The environment for methods, as taught herein, can be a vacuum environment and a non-vacuum environment.

Figure 27:
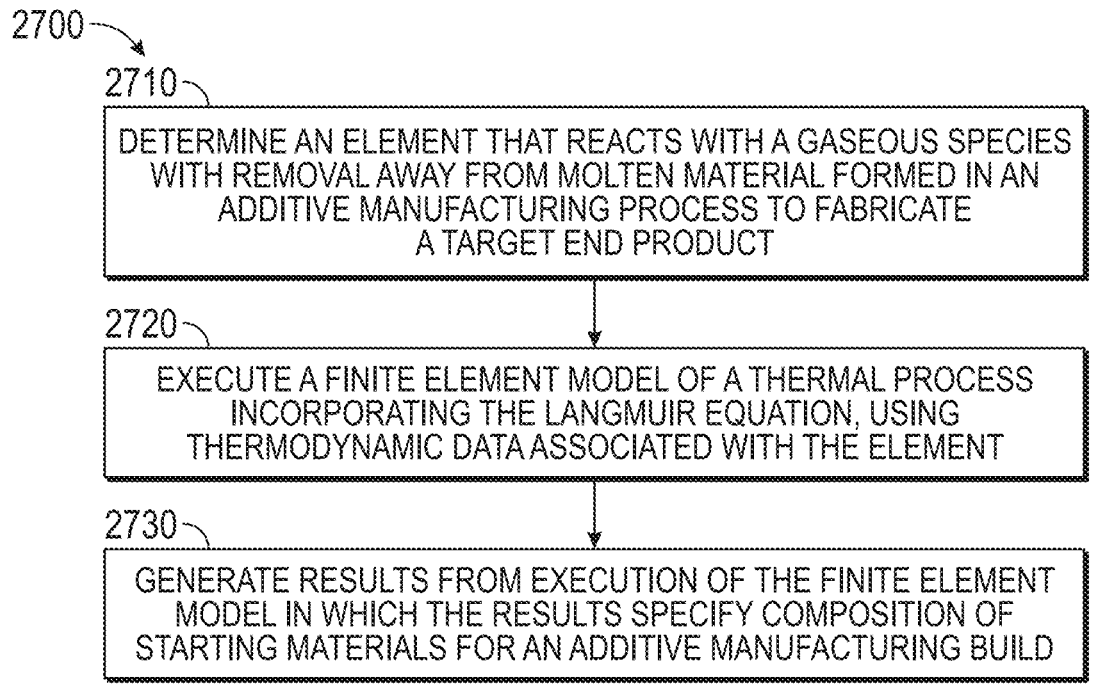
FIG. 27 is a flow diagram of features of an example method to conduct an additive manufacturing process.

FIG. 27 is a flow diagram of features of an embodiment of an example method 2700 to conduct an AM process. Method 2700 can be implemented using one or more processors. At 2710, a determination is made as to what element or elements will react with gaseous species with removal away from molten material formed in the AM process to fabricate a target end product. The determination can include accessing one or more databases having thermodynamic databases and other data, providing knowledge regarding possible elements and compounds that can be used in the AM process to produce the target end product, calculating data for the element, applying different conditions to generate data regarding the element, or performing combinations thereof. The databases can be accessed remotely over a communications network. The target end product can be defined to include a composition within a range of a target composition.

At 2720, a finite element model of a thermal process incorporating a Langmuir equation can be executed using thermodynamic data associated with the element or the elements. As noted, the Langmuir equation can be used to analyze how much material is lost per unit time. In executing the finite element model with the Langmuir equation and thermodynamic data, one or more data inputs can be provided to a system storing and/or executing a processing model or simulation model that includes the finite element model of thermal processes with the Langmuir equation integrated to conduct an additive manufacturing build. The input can include one or more of identifications for a target end product or target composition, thermodynamic parameters relevant to the elements associated with the target end product or the target composition, allowable variances for a particular additive manufacturing build and/or target end product, or other data to execute the finite element model. Method 2700 can include determining or knowing how hot the molten pool of the molten material gets and how long the molten pool is in its molten state, such that there is a temperature component as well as a time component in the analysis.

At 2730, results from execution of the finite element model can be generated in which the results specify composition of starting materials for an additive manufacturing build. The starting materials can be specified as the identification of elements of the starting materials and concentration ranges of the elements of the starting materials within a specified range of composition that can be used to fabricate the target end product. The starting materials can include the starting chemistry that one would use in an incoming wire in the AM process. The specified range of composition can include ranges of concentration of elements in the target end product. The specified range of composition can also include identification of trace elements, where trace elements are unwanted elements with respect to a pure target composition, and thresholds for acceptable levels of the trace elements.

Variations of method 2700 or methods similar to method 2700 can include a number of different embodiments that may be combined depending on the application of such methods and/or the architecture of systems in which such methods are implemented. Such methods can include after generating the results that specify composition of starting materials: processing material of the starting materials including the element, by additive manufacturing processing in which a molten pool is formed in a processing structure; providing the element into an environment of the processing structure, with the element provided in controlled concentrations to preferentially volatilize and remove material species other than the element above the molten pool; monitoring temperature of the molten pool and/or monitoring a location within a simulation corresponding to position in the molten pool being processed; and adjusting the providing of the element and/or the controlled concentrations using an output from a model tied to the Langmuir equation based on data from the monitoring. Providing the element into an environment of the processing structure can include introducing the element into a powder bed system or a powder blown system, with the element included in a sacrificial powder provided and distributed in a controlled manner.

Figure 28:
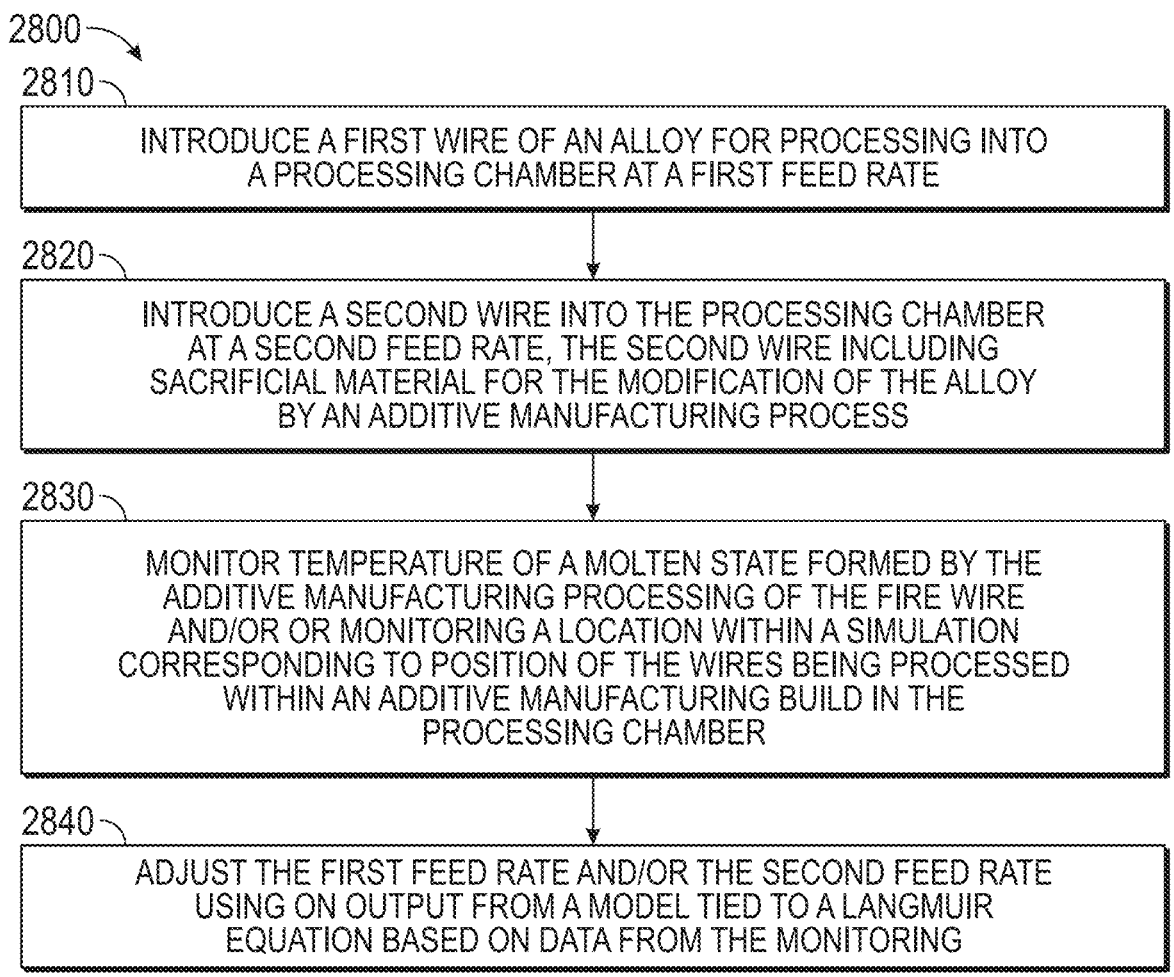
FIG. 28 is a flow diagram of features of an example method of providing interstitial control during an additive manufacturing process.

FIG. 28 is a flow diagram of features of an embodiment of an example method 2800 of providing interstitial control during AM processes. Method 2800 can be implemented using one or more processors to control a number of functions in the AM processes. At 2810, a first wire of an alloy for processing is introduced into a processing chamber at a first feed rate. At 2820, a second wire is introduced into the processing chamber at a second feed rate. The second wire can include sacrificial material for the modification of the alloy by an AM process. At 2830, temperature of a molten state formed by the AM processes of the first wire is monitored or a location within a simulation corresponding to position of the wires being processed within an AM build in the processing chamber is monitored.

At 2840, the first feed rate and/or the second feed rate are adjusted by use of output from a model tied to a Langmuir equation based on data from the monitoring. The model can be a finite element model. The data form the monitoring can include a temperature component and a time component in the model tied to the Langmuir equation. Adjusting the first feed rate and/or the second feed rate can include halting the feeding of the first wire and the second wire for a period of time in a processing cycle. The adjustment of the first feed rate and/or the second feed rate can be accomplished by causing the mechanical speed of a spindle, or other drive device, associated with the first feed rate and/or the mechanical speed of a spindle, or other drive device, associated with the first feed rate to change.

Method 2800 or similar methods can provide for real time processing that provides interstitial control during AM processing of an AM build in the processing chamber. The control of an AM build by a system using thermodynamic data of elements in the build and tying the Langmuir equation to a model, such as a finite element model, provides a cyber physical implementation that permits chemically hybrid structures in which the chemistry can be intentionally varied through the part.

Figure 29:
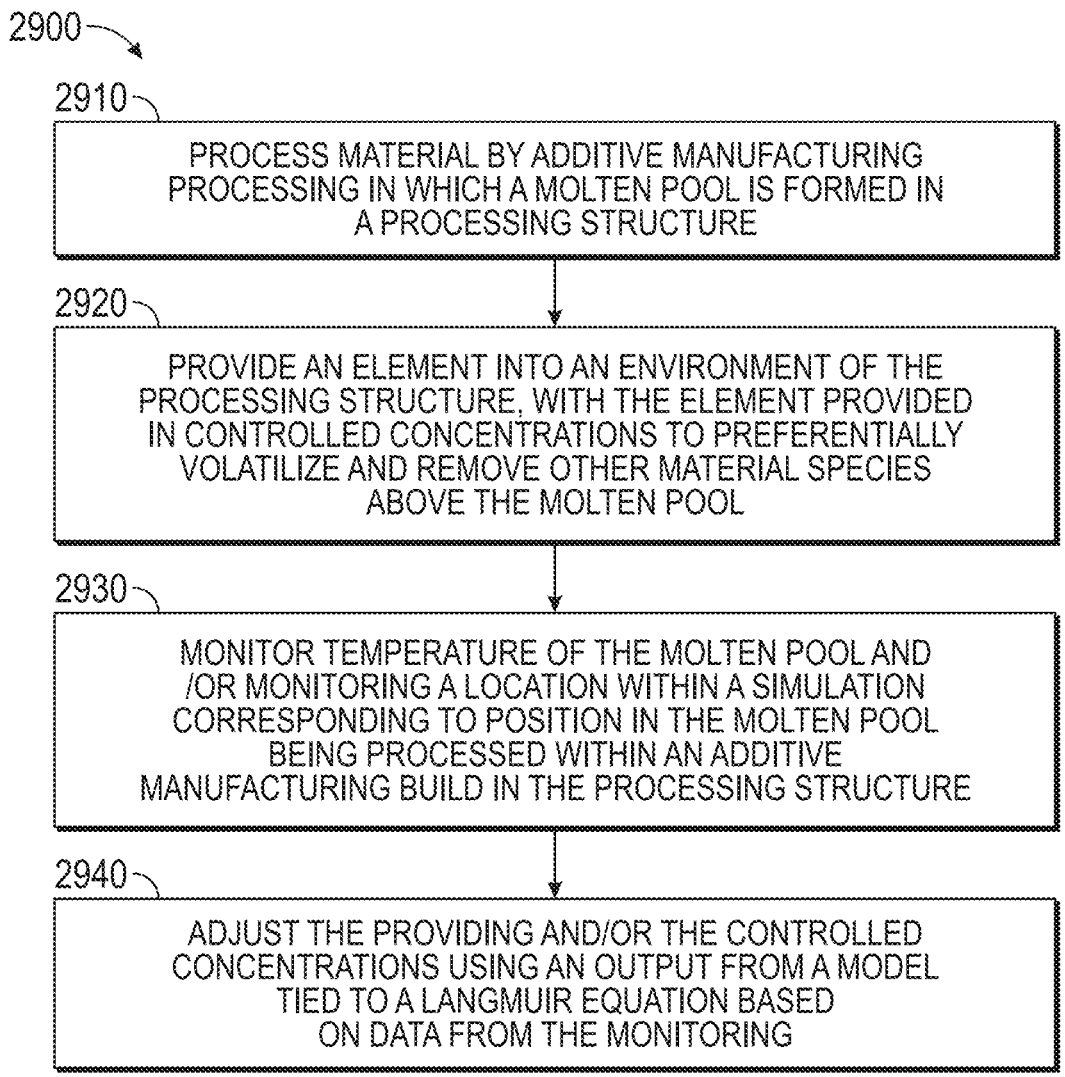
FIG. 29 is a flow diagram of features of an example method of providing interstitial control during an additive manufacturing process.

FIG. 29 is a flow diagram of features of an embodiment of an example method 2900 of providing interstitial control during AM processes. Method 2900 can be implemented using one or more processors to control a number of functions in the AM processes. At 2910, material is processed by additive manufacturing processing in which a molten pool is formed in a processing structure. At 2920, an element is provided into an environment of the processing structure, with the element is provided in controlled concentrations to preferentially volatilize and remove material species other than the element above the molten pool. Providing the element into an environment of the processing structure can include introducing the element into a powder bed system or a powder blown system. The element can be included in a sacrificial powder provided and distributed in a controlled manner.

At 2930, temperature of the molten pool is monitored and/or a location within a simulation is monitored, where the location corresponds to position in the molten pool being processed within an additive manufacturing build in the processing structure. At 2940, the providing of the element and/or the controlled concentrations is adjusted using an output from a model tied to a Langmuir equation based on data from the monitoring. Adjusting the providing of the element can include adjusting a feed rate for providing the element. The data from the monitoring can include a temperature component and a time component in the model tied to the Langmuir equation. The model tied to the Langmuir equation can be a finite element model. Data from one or more databases having the thermodynamics data, calculation of data for elements, or application of different conditions to generate data can be used to generate a margin of error to modify one or more co-feed wires or one or more powders.

Variations of method 2700, method 2800, method 2900, combinations of method 2700, method 2800, and method 2900, or methods similar to method 2700, method 2800, method 2900, combinations of method 2700, method 2800, and method 2900, or other methods taught herein can include a number of different embodiments that can be combined depending on the application of such methods and/or the architecture of systems in which such methods are implemented. In addition, systems can comprise instrumentalities to perform the functions of method 2700, method 2800, method 2900, variations of method 2700, method 2800, method 2900, combinations of method 2700, method 2800, and method 2900, or methods similar to method 2700, method 2800, method 2900, combinations of method 2700, method 2800, and method 2900, or other methods taught herein In various embodiments, a machine-readable storage device, such as computer-readable medium, can comprise instructions stored thereon, which, when performed by a machine, cause the machine to perform operations, where the operations comprise one or more features similar to or identical to features of methods and techniques described with respect to method 2700, method 2800, method 2900, and combinations of method 2700, method 2800, and method 2900, variations thereof, and/or features of other methods taught herein. A machine-readable storage device is a non-transitory device. The physical structures of such instructions may be operated on by one or more processors.

A machine-readable storage device can comprise instructions, which when executed by a one or more processors, cause a system to perform operations, the operations comprising operations to determine an element that reacts with a gaseous species with removal away from molten material formed in an additive manufacturing process to fabricate a target end product; apply a Langmuir equation to parameters of the element, the parameters including thermodynamic data; tie the Langmuir equation and the thermodynamic data into a finite element model of a thermal process of an additive manufacturing build of the target end product; and generate results from execution of the finite element model in which the results specify composition of starting materials for the additive manufacturing build. The instructions can include a number of operations and/or variations of operations.

The operations can include operations to determine the element that can include operations to access one or more databases having the thermodynamic data of the element to produce the target end product; to calculate data for the element, to apply different conditions to generate data regarding the element, or to perform combinations thereof. The target end product can be defined by a composition within a range of a target composition. The operations to tie the Langmuir equation and the thermodynamic data into the finite element model can include operations to provide a temperature component and a time component. The operations to generate the results can include operations to specify identification of elements of the starting materials and concentration ranges of the elements of the starting materials within a specified range of composition.

A machine-readable storage device can comprise instructions, which when executed by a one or more processors, cause a system to perform operations, the operations comprising operations to determine an element that reacts with a gaseous species with removal away from molten material formed in an additive manufacturing process to fabricate a target end product; execute a finite element model of a thermal process incorporating the Langmuir equation, using thermodynamic data associated with the element; and generate results from execution of the finite element model in which the results specify composition of starting materials for an additive manufacturing build. The instructions can include a number of operations and/or variations of operations.

The operations can include operations to determine the element that can include operations to access one or more databases having the thermodynamic data of the element to produce the target end product; to calculate data for the element, to apply different conditions to generate data regarding the element, or to perform combinations thereof. The target end product can be defined to include a composition within a range of a target composition. The operations to execute the finite element model can include operations to provide a temperature component and a time component. The operations to generate the results can include operations to specify identification of one or more elements of the starting materials and concentration ranges of the one or more elements of the starting materials within a specified range of composition.

A machine-readable storage device comprising instructions, which when executed by a one or more processors, cause a system to perform operations, the operations comprising operations to: introduce a first wire of an alloy for processing into a processing chamber at a first feed rate; introduce a second wire into the processing chamber at a second feed rate, the second wire including sacrificial material for the modification of the alloy by an additive manufacturing process; monitor temperature of a molten state formed by the additive manufacturing processing of the first wire and/or or monitor a location of a stored simulation corresponding to position of the wires being processed within an additive manufacturing build in the processing chamber; and adjust the first feed rate and/or the second feed rate by use of output from a model tied to a Langmuir equation based on data from the monitoring.

The instructions can include a number of operations and/or variations of operations. The model tied to the Langmuir equation can be a finite element model. The data from the monitoring can include a temperature component and a time component in the model tied to the Langmuir equation. The operations to adjust the first feed rate and/or the second feed rate includes operations to halt the feeding of the first wire and the second wire for a period of time in a processing cycle.

A machine-readable storage device comprising instructions, which when executed by a one or more processors, cause a system to perform operations, the operations comprising operations to: process material by additive manufacturing processing in which a molten pool is formed in a processing structure; provide an element into an environment of the processing structure, with the element provided in controlled concentrations to preferentially volatilize and remove material species other than the element above the molten pool; monitor temperature of the molten pool and/or monitoring a location within a simulation corresponding to position in the molten pool being processed within an additive manufacturing build in the processing structure; and adjust the providing of the element and/or the controlled concentrations using an output from a model tied to a Langmuir equation based on data from the monitoring.

The instructions can include a number of operations and/or variations of operations. The model tied to the Langmuir equation can be a finite element model. The data from the monitoring can include a temperature component and a time component in the model tied to the Langmuir equation. The operations to adjust the providing of the element can include adjusting a feed rate for providing the element. The operations to provide the element into an environment of the processing structure can include introducing the element into a powder bed system or a powder blown system. The element can be included in a sacrificial powder provided and distributed in a controlled manner.

Further, machine-readable storage devices, such as computer-readable media, herein, are physical devices that store data represented by physical structure within the respective device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices. The machine-readable device may be a machine-readable medium such as a memory. While a memory may be a single component unit, terms such as "memory," "memory module," "machine-readable medium," "machine-readable storage device," and similar terms should be taken to include all forms of storage media, either in the form of a single medium (or device) or multiple media (or devices), in all forms. For example, such structures can be realized as centralized database(s), distributed database(s), associated caches, and servers; one or more storage devices, such as storage drives (including but not limited to electronic, magnetic, and optical drives and storage mechanisms), and one or more instances of memory devices or modules (whether main memory; cache storage, either internal or external to a processor; or buffers). The term "non-transitory" used in reference to a "machine-readable device," "medium," "storage medium," "device," or "storage device" expressly includes all forms of storage drives (optical, magnetic, electrical, etc.) and all forms of memory devices (e.g., DRAM, Flash (of all storage designs), SRAM, MRAM, phase change, etc., as well as all other structures designed to store data of any type for later retrieval.

Variations of machine-readable storage devices and/or instructions to execute features of methods taught herein including but not limited to method 2700, method 2800, method 2900, combinations of method 2700, method 2800, and method 2900, methods similar to method 2700, method 2800, method 2900, or combinations of method 2700, method 2800, and method 2900 can include a number of different embodiments that can be combined depending on the application of such machine-readable storage devices and/or the architecture of systems in which such machine-readable storage devices are implemented.

In various embodiments, a system comprises a set of processors and a storage device comprising instructions, which when executed by the set of processors, cause the system to perform operations directed to additive manufacturing process. The system can be arranged as a system to identify materials and conditions for producing a target end product using one or more additive manufacturing processes. The operations can include operations to determine an element that reacts with a gaseous species with removal away from molten material formed in an additive manufacturing process to fabricate a target end product; apply a Langmuir equation to parameters of the element, the parameters including thermodynamic data; tie the Langmuir equation and the thermodynamic data into a finite element model of an thermal process of an additive manufacturing build of the target end product; and generate results from execution of the finite element model in which the results specify composition of starting materials for the additive manufacturing build. Identification of the target end product or target composition can be an input to the system. The set of processors and the storage device can be arranged to perform operations of method 2700, methods similar to method 2700, simulations to generate results for use in conducting an additive manufacturing build for a specified end product, the system, which identifies materials and conditions for producing a target end product using one or more additive manufacturing processes, can be incorporated in or with a system that controls the physical processing for the target end product, using one or more AM processes.

Variations of the system, which identifies materials and conditions for producing a target end product using one or more additive manufacturing processes, or similar systems can include a number of different embodiments that can be combined depending on the application of such systems and/or the architecture in which such systems are implemented. The system can include a number of different features. The set of processors of the system can be arranged to determine the reactive element or reactive elements by use of one or more databases having thermodynamic data of the reactive element or reactive elements to produce the target end product; to calculate data for the element, to apply different conditions to generate data regarding the element, or to perform combinations thereof. The one or more databases can be accessed locally or remotely over a communications network. The one or more databases can be incorporated into the system. The set of processors of the system can be arranged to provide a temperature component and a time component to tie the Langmuir equation and the thermodynamic data into the finite element model. The set of processors of the system can be arranged to generate the results that include specification of an identification of elements of the starting materials and concentration ranges of the elements of the starting materials within a specified range of composition. The target end product can be defined to include a composition within a range of a target composition.

In various embodiments, a system comprises a set of processors and a storage device comprising instructions, which when executed by the set of processors, cause the system to perform operations directed to additive manufacturing process. The system can be arranged as a system operable to identify materials and conditions for producing a target end product using one or more additive manufacturing processes. The operations can include operations to determine an element that reacts with a gaseous species with removal away from molten material formed in an additive manufacturing process to fabricate a target end product; execute a finite element model of a thermal process incorporating the Langmuir equation, using thermodynamic data associated with the element; and generate results from execution of the finite element model in which the results specify composition of starting materials for an additive manufacturing build.

Identification of the target end product or target composition can be an input to the system. The set of processors and the storage device can be arranged to perform operations of method 2700, methods similar to method 2700, simulations to generate results for use in conducting an additive manufacturing build for a specified end product, the system, which identifies materials and conditions for producing a target end product using one or more additive manufacturing processes, can be incorporated in or with a system that controls the physical processing for the target end product, using one or more AM processes.

Variations of the system, which identifies materials and conditions for producing a target end product using one or more additive manufacturing processes, or similar systems can include a number of different embodiments that can be combined depending on the application of such systems and/or the architecture in which such systems are implemented. The system can include a number of different features. The set of processors of the system can be arranged to determine the reactive element or reactive elements by use of one or more databases having thermodynamic data of the reactive element or reactive elements to produce the target end product; to calculate data for the element, to apply different conditions to generate data regarding the element, or to perform combinations thereof. The one or more databases can be accessed locally or remotely over a communications network. The one or more databases can be incorporated into the system. The set of processors of the system can be arranged to provide a temperature component and a time component to the finite element model. The set of processors of the system can be arranged to generate the results that include specification of an identification of elements of the starting materials and concentration ranges of the elements of the starting materials within a specified range of composition. The target end product can be defined to include a composition within a range of a target composition.

In various embodiments, a system comprises a set of processors and a storage device comprising instructions, which when executed by the set of processors, cause the system to perform operations directed to additive manufacturing process. The system directed to additive manufacturing process can be arranged to include as a system operable to identify materials and conditions for producing a target end product using one or more additive manufacturing processes. The operations of the system directed to additive manufacturing process can include operations to process material by additive manufacturing processing in which a molten pool is formed in a processing structure; provide an element into an environment of the processing structure, with the element provided in controlled concentrations to preferentially volatilize and remove material species other than the element above the molten pool; monitor temperature of the molten pool and/or monitor a location within a simulation corresponding to position in the molten pool being processed within an additive manufacturing build in the processing structure; and adjust the providing of the element and/or the controlled concentrations using an output from a model tied to a Langmuir equation based on data from the monitoring. The model tied to the Langmuir equation can be a finite element model.

Such a system directed to additive manufacturing process can include a number of features. The data from the monitoring can include a temperature component and a time component in the model tied to the Langmuir equation. Operations to adjust the providing of the element can include adjustment of a feed rate for providing the element. Operations to the element into an environment of the processing structure can include introducing the element into a powder bed system or a powder blown system. In such powder systems, the element can be included in a sacrificial powder provided and distributed in a controlled manner.

Identification of a target end product or target composition can be an input to the system. The set of processors and the storage device can be arranged to also perform operations of method 2700, methods similar to method 2700, simulations to generate results for use in conducting an additive manufacturing build for a specified end product. A system which identifies materials and conditions for producing a target end product using one or more additive manufacturing processes, can be incorporated in or with a system that controls the physical processing for the target end product, using one or more AM processes.

Figure 30:
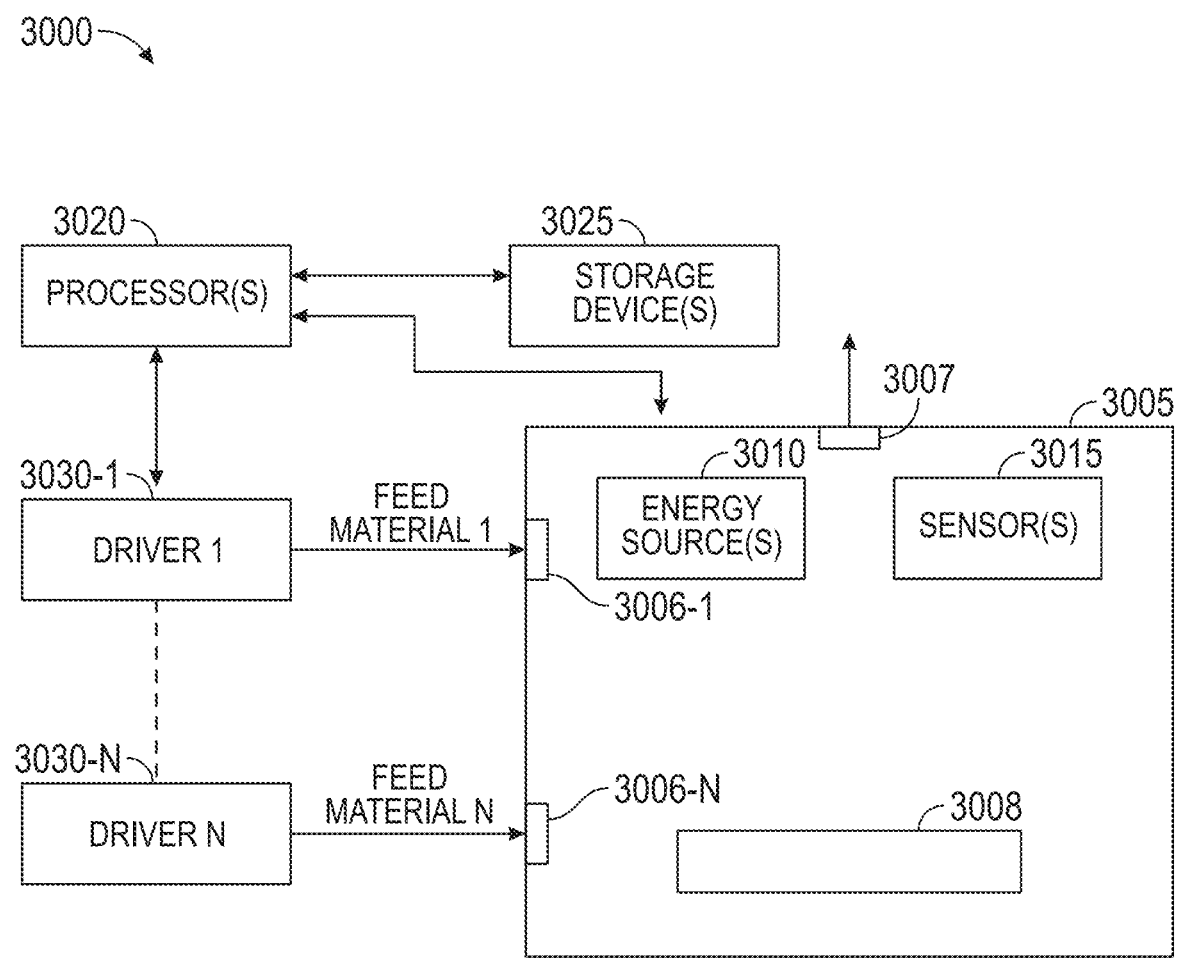
FIG. 30 is a block diagram of a system in which one or more additive manufacturing processes can be used during the fabrication of an end product.

FIG. 30 is a block diagram of a system 3000 in which one or more AM processes can be used during the fabrication of an end product. System 3000 can include a processing chamber 3005 or processing structure, which chamber or structure be configured as a vacuum processing chamber or a non-vacuum processing. For ease of discussion, environmental control equipment, such as but not limited to pumps, are not shown. Processing chamber 3005 can include one or more input ports 3006-1 . . . 3006-N for receiving one or more of feed material 1 . . . feed material N, respectively, and an exit port 3007 to remove gases from processing chamber 3005. Exit port 3007 can be realized as one more exit ports.

Processing chamber 3005 can include one or more energy sources 3010 to provide appropriate stimulus to one or more of feed material 1 . . . feed material N provided to a workpiece platform 3008 to preform one or more AM processes. Feed material 1 . . . feed material N can be input to processing chamber 3005 by driver 3030-1 . . . driver 3030-N, respectively. One or more of driver 3030-1 . . . driver 3030-N can include a mechanical spindle to input the appropriate feed material. The temperature and atmospheric conditions in processing chamber 3005 can be monitored using one or more sensors 3015.

System 3000 can comprise a set of one or more processors 3020 and one or more storage devices 3025, where storage devices 3015 can comprise instructions, which when executed by the set of processors, cause the system to perform operations to control instrumentalities associated with preforming AM processes in processing chamber 3005. The one or more storage devices 3025 can be realized as one or more memory devices, one or more databases, or other instrumentality that stores information. In the AM processing the one or more processors 3020 can be arranged to control driver 3030-1 . . . driver 3030-N, energy sources 3010, sensors 3015, and other instruments in the performance of AM processing such as but not limited to environmental control equipment. The operations executed by the set of one or more processors 3020 can include operations to: introduce a first wire of an alloy for processing into processing chamber 3005 at a first feed rate; introduce a second wire into the processing chamber at a second feed rate, the second wire including sacrificial material for the modification of the alloy by an additive manufacturing process; monitor temperature of a molten state formed by the additive manufacturing processing of the first wire and/or or monitor a location of a stored simulation corresponding to position of the wires being processed within an additive manufacturing build in processing chamber 3005; and adjust the first feed rate and/or the second feed rate by use of output from a model tied to a Langmuir equation based on data from the monitoring. The model tied to the Langmuir equation can be a finite element model. The set of one or more processors 3020 and one or more storage devices 3025 can be arranged to generate the model, such as but not to a finite element model, incorporating the Langmuir equation.

Data from monitoring can include a temperature component and a time component in the model tied to the Langmuir equation. Sensors 3015 of system 3000 can include a temperature sensor to monitor the temperature of the molten state formed by the additive manufacturing processing. The set of processors 3020 can be arranged to halt the feeding of the first wire and the second wire for a period of time in a processing cycle to adjust the first feed rate and/or the second feed rate. Control of different rates of introducing feed material 1 . . . feed material N can allow for the AM production of a target end product and/or target composition in which the elements of the target end product and/or target composition are within specified ranges of concentration within the target end product and/or target composition. The specification can also include threshold levels of concentration below which undesired elements are acceptable.

Systems for AM processing that provide interstitial control during the AM processing are not limited to wire fed systems. The approach as taught herein can also be achieved on powder bed and powder blown systems. In powder bed systems, an energy source, such as a laser, selectively melts a bed of metallic powder in a layer-by-layer process to build up a physical product, where the physical product is formed in the processing within a powder that is subsequently removed to expose the physical product. In blown powder systems, the process is controlled to continuously blow powder into the melt pool, and the energy source, such as a laser, builds up the part in a layer by layer manner that is not buried within powder. In such instantiations, sacrificial powder is brought into the system and distributed in a controlled manner. In powder bed and powder blown systems, the application of a Langmuir equation via real time digital processing or via a simulation is the same as or similar to the wire fed systems, but the form of the material changes. In powder bed or powder blown systems, a powder of element A can be added in controlled concentrations to preferentially volatilize and remove oxygen, or other species, above a molten pool. Similar methods of rate of material addition can be achieved through physical mechanisms on those systems.

Variations of system 3000 can include a number of different embodiments that can be combined depending on the application of system 3000 or similar systems and/or the architecture in which such systems are implemented. System 3000 can also include, as a sub-system, a system that identifies materials and conditions for producing a target end product using one or more additive manufacturing processes, as discussed above. System 3000 can also include, as a sub-system, a system that ties the Langmuir equation to a model of thermal processes such as, but not limited to, a finite element model. System 3000, systems similar to system 3000, and variations of system 3000 or similar system can include instrumentalities to execute features of method 2700, method 2800, combinations of method 2700 and method 2800, methods similar to method 2700, method 2800, or combinations of method 2700 and method 2800, or other functions as taught herein.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description.

What is claimed is:

1. A computer-implemented method of operating an additive manufacturing system, the computer-implemented method comprising:
    fabricating a target end product in an additive manufacturing process using one or more processors executing stored instructions to perform operations including:
        accessing, via a communication network, one or more databases having thermodynamic data associated with a composition of the target end product and thermodynamic data of candidates to react with a gaseous species in an environment in which the target end product is fabricated;
        determining a sacrificial element, from among the candidates, to react with and remove the gaseous species away from molten material formed in the additive manufacturing process to fabricate the target end product;
        executing a finite element model of a thermal process incorporating a Langmuir equation, using the thermodynamic data associated with the composition of the target end product and the sacrificial element;
        generating results from execution of the finite element model in which the results specify composition of starting materials for an additive manufacturing build, the starting materials including the sacrificial element with the sacrificial element to combine with the gaseous species in the processing environment to prevent the gaseous species from entering into the molten material such that one or more components of the gaseous species are included in the target end product at a level below a threshold for acceptable levels of the one or more components of the gaseous species in the target end product; and
        transmitting the results to control instruments associated with preforming the additive manufacturing process to fabricate the target end product.

2. The computer-implemented method of claim 1, wherein determining the sacrificial element includes calculating data for the sacrificial element or applying different conditions to generate data regarding the sacrificial element.

3. The computer-implemented method of claim 1, wherein executing the finite element model includes providing a temperature component and a time component.

4. The computer-implemented method of claim 1, wherein the target end product is defined to include a composition within a range of a target composition.

5. The computer-implemented method of claim 1, wherein generating the results includes specifying identification of elements of the starting materials and concentration ranges of the elements of the starting materials within a specified range of composition.

6. The computer-implemented method of claim 1, wherein the method includes, after generating the results that specify composition of starting materials:
    processing material of the starting materials including the sacrificial element, by additive manufacturing processing in which a molten pool is formed in a processing structure;
    providing the sacrificial element into the environment of the processing structure, with the sacrificial element provided in controlled concentrations to preferentially volatilize and remove material species other than the sacrificial element above the molten pool;
    monitoring temperature of the molten pool and/or monitoring a location within a simulation corresponding to position in the molten pool being processed; and
    adjusting the providing of the sacrificial element and/or the controlled concentrations using an output from the finite element model tied to the Langmuir equation based on data from the monitoring.

7. The computer-implemented method of claim 6, wherein providing the sacrificial element into the environment of the processing structure includes introducing the sacrificial element into a powder bed system or a powder blown system, with the sacrificial element included in a sacrificial powder provided and distributed in a controlled manner.

8. A non-transitory machine-readable storage device comprising instructions, which when executed by a one or more processors, cause a system to perform operations to operate an additive manufacturing system, the operations comprising operations to fabricate a target end product in an additive manufacturing process including operations to:
    access, via a communication network, one or more databases having thermodynamic data associated with composition of the target end product and thermodynamic data of candidates to react with a gaseous species in an environment in which the target end product is fabricated;

determine a sacrificial element, from among the candidates, to react with and remove the gaseous species away from molten material formed in the additive manufacturing process to fabricate the target end product;

execute a finite element model of a thermal process incorporating a Langmuir equation, using the thermodynamic data associated with the composition of the target end product and the sacrificial element;

generate results from execution of the finite element model in which the results specify composition of starting materials for an additive manufacturing build, the starting materials including the sacrificial element with the sacrificial element to combine with the gaseous species in the processing environment to prevent the gaseous species from entering into the molten material such that one or more components of the gaseous species are included in the target end product at a level below a threshold for acceptable levels of the one or more components of the gaseous species in the target end product; and transmit the results to control instruments associated with preforming the additive manufacturing process to fabricate the target end product.

9. The non-transitory machine-readable storage device of claim 8, wherein operations to determine the element includes operations to access one or more databases having the thermodynamic data of the element to produce the target end product; to calculate data for the element, or to apply different conditions to generate data regarding the element.

10. The non-transitory machine-readable storage device of claim 8, wherein operations to execute the finite element model include operations to provide a temperature component and a time component.

11. The non-transitory machine-readable storage device of claim 8, wherein the target end product is defined to include a composition within a range of a target composition.

12. The non-transitory machine-readable storage device of claim 8, wherein operations to generate the results include operations to specify identification of elements of the starting materials and concentration ranges of the elements of the starting materials within a specified range of composition.

13. A method comprising:
introducing a first wire of an alloy for processing into a processing chamber at a first feed rate, the processing chamber having a processing environment;
introducing a second wire into the processing chamber at a second feed rate, the second wire including sacrificial material for modification of the alloy by an additive manufacturing process;
monitoring temperature of a molten state formed by the additive manufacturing processing of the first wire and/or or monitoring a location within a simulation corresponding to position of the wires being processed within an additive manufacturing build in the processing chamber; and
adjusting, based on data from the monitoring, the first feed rate and/or the second feed rate using on output from a model tied to a Langmuir equation and thermodynamic data of the sacrificial material and a target composition of the additive manufacturing build, the model including the composition of the sacrificial material during the additive manufacturing build to produce a target composition with the sacrificial material combining with one or more elements in the processing environment to prevent the one or more elements from entering into the molten state such that the one or more elements are included in the target composition at a level below one or more thresholds for acceptable levels of the one or more elements in the target composition.

14. The method of claim 13, wherein the model tied to the Langmuir equation is a finite element model.

15. The method of claim 14, wherein the data from the monitoring includes a temperature component and a time component in the model tied to the Langmuir equation.

16. The method of claim 13, wherein adjusting the first feed rate and/or the second feed rate includes halting the feeding of the first wire and the second wire for a period of time in a processing cycle.

17. A non-transitory machine-readable storage device comprising instructions, which when executed by a one or more processors, cause a system to perform operations, the operations comprising operations to:
introduce a first wire of an alloy for processing into a processing chamber at a first feed rate, the processing chamber having a processing environment;
introduce a second wire into the processing chamber at a second feed rate, the second wire including sacrificial material for modification of the alloy by an additive manufacturing process;
monitor temperature of a molten state formed by the additive manufacturing processing of the first wire and/or or monitor a location of a stored simulation corresponding to position of the wires being processed within an additive manufacturing build in the processing chamber; and
adjust, based on data from the monitoring, the first feed rate and/or the second feed rate by use of output from a model tied to a Langmuir equation and thermodynamic data of the sacrificial material and a target composition of the additive manufacturing build, the model including the composition of the sacrificial material during the additive manufacturing build to produce a target composition with the sacrificial material combining with one or more elements in the processing environment to prevent the one or more elements from entering into the molten state such that the one or more elements are included in the target composition at a level below one or more thresholds for acceptable levels of the one or more elements in the target composition.

18. The non-transitory machine-readable storage device of claim 17, wherein the model tied to the Langmuir equation is a finite element model.

19. The non-transitory machine-readable storage device of claim 18, wherein the data from the monitoring includes a temperature component and a time component in the model tied to the Langmuir equation.

20. The non-transitory machine-readable storage device of claim 17, wherein operations to adjust the first feed rate and/or the second feed rate includes operations to halt the feeding of the first wire and the second wire for a period of time in a processing cycle.

* * * * *

UNITED STATES PATENT AND TRADEMARK OFFICE
CERTIFICATE OF CORRECTION

PATENT NO. : 11,379,637 B2
APPLICATION NO. : 16/787973
DATED : July 5, 2022
INVENTOR(S) : Collins et al.

It is certified that error appears in the above-identified patent and that said Letters Patent is hereby corrected as shown below:

On the Title Page

On page 2, in Column 2, under "Other Publications", Line 5, delete "a + β-processed a/β" and insert --α + β-processed α/β-- therefor In the Specification In Column 4, Line 44, delete "Gound" and insert --Gouné-- therefor In Column 9, Line 62, delete "a" and insert --α-- therefor In Column 14, Line 57, delete ""Aradiometric" and insert --"A radiometric-- therefor In Column 36, Line 14, delete "3015" and insert --3025-- therefor Signed and Sealed this
Twenty-third Day of May, 2023

Katherine Kelly Vidal
*Director of the United States Patent and Trademark Office*